US008168653B2

(12) United States Patent
Guicherit et al.

(10) Patent No.: US 8,168,653 B2
(45) Date of Patent: May 1, 2012

(54) MEDIATORS OF HEDGEHOG SIGNALING PATHWAYS, COMPOSITIONS AND USES RELATED THERETO

(75) Inventors: Oivin M. Guicherit, San Diego, CA (US); Edward Andrew Boyd, Henfield (GB); Shirley Ann Brunton, Berkshire (GB); Stephen Price, Hertford (GB); John Harry Alexander Stibbard, Oxfordshire (GB); Colin H. Mackinnon, Oxfordshire (GB)

(73) Assignees: Curis, Inc., Lexington, MA (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/848,466

(22) Filed: Aug. 2, 2010

(65) Prior Publication Data

US 2010/0317660 A1    Dec. 16, 2010

Related U.S. Application Data

(63) Continuation of application No. 11/718,470, filed as application No. PCT/US2005/040054 on Nov. 3, 2005, now Pat. No. 7,816,369.

(60) Provisional application No. 60/624,536, filed on Nov. 3, 2004.

(51) Int. Cl.
*A61K 31/4427* (2006.01)
*C07D 471/04* (2006.01)
*C07D 413/02* (2006.01)
*C07D 401/02* (2006.01)

(52) U.S. Cl. ..... 514/303; 514/321; 546/118; 546/271.7; 546/273.4

(58) Field of Classification Search ................ 514/303, 514/321; 546/118, 271.7, 273.4
See application file for complete search history.

(56) References Cited

U.S. PATENT DOCUMENTS 6,897,208 B2    5/2005   Edwards

FOREIGN PATENT DOCUMENTS

| WO | WO 03/011219 | 2/2003 |
| WO | WO 03/082186 | 10/2003 |
| WO | WO 2005/002552 | 1/2005 |

OTHER PUBLICATIONS

Golub et al. Science (1999), vol. 286 531-537.*
Lala et al. Cancer and Metastasis Reviews (1998), 17(1), 91-106.*

* cited by examiner

*Primary Examiner* — Rebecca Anderson
*Assistant Examiner* — Samantha Shterengarts
(74) *Attorney, Agent, or Firm* — Millen, White, Zelano & Branigan, P.C.

(57) ABSTRACT

The present invention makes available methods and reagents for inhibiting aberrant growth states resulting from hedgehog gain-of-function, ptc loss-of-function or smoothened gain-of-function comprising contacting the cell with a hedgehog antagonist of formula (I) in a sufficient amount to aberrant growth state, e.g., to agonize a normal ptc pathway or antagonize smoothened or hedgehog activity.

14 Claims, No Drawings

MEDIATORS OF HEDGEHOG SIGNALING PATHWAYS, COMPOSITIONS AND USES RELATED THERETO

This application is a continuation of U.S. Ser. No. 11/718, 470, filed Mar. 31, 2008 now U.S. Pat. No. 7,816,369. U.S. Ser. No. 11/718,470 is a national stage entry of PCT/US05/40054, filed Nov. 3, 2005. PCT/US05/40054 claims priority to U.S. Provisional application No. 60/624,536, filed Nov. 3, 2004, the specification of which is hereby incorporated herein by reference in its entirety.

BACKGROUND OF THE INVENTION

Hedgehog (Hh) protein was first identified in *Drosophila melanogaster* as a segment-polarity gene involved in embryo patterning (Nusslein-Volhard et al., Roux. Arch. Dev. Biol. 193:267-282 (1984)). Three orthologs of *Drosophila* hedgehog (Sonic, Desert and Indian) were later identified to occur in all vertebrates including fish, birds and mammals. Desert hedgehog (DHh) is expressed principally in the testes, both in mouse embryonic development and in the adult rodent and human; Indian hedgehog (IHh) is involved in bone development during embryogenesis and in bone formation in the adult; and, Sonic hedgehog (SHh) is expressed at high levels in the notochord and floor plate of developing vertebrate embryos. In vitro explant assays as well as ectopic expression of SHh in transgenic animals have shown that SHh plays a key role in neuronal tube patterning (Echelard et al., supra; Ericson et al., Cell 81:747-56 (1995); Marti et al., Nature 375: 322-5 (1995); Krauss et al., Cell 75, 1432-44 (1993); Riddle et al., Cell 75:1401-16 (1993); Roelink et al, Cell 81:445-55 (1995); Hynes et al., Neuron 19:15-26 (1997)). Hh also plays a role in the development of limbs (Krauss et al, Cell 75:1431-44 (1993); Laufer et al., Cell 79, 993-1003 (1994)), somites (Fan and Tessier-Lavigne, Cell 79, 1175-86 (1994); Johnson et al., Cell 79:1165-73 (1994)), lungs (Bellusci et ah, Develop. 124:53-63 (1997) and skin (Oro et al., Science 276:817-21 (1997)). Likewise, IHh and DHh are involved in bone, gut and germinal cell development (Apelqvist et al., Curr. Biol. 7:801-4 (1997); Bellusci et al., Dev. Suppl. 124: 53-63 (1997); Bitgood et al, Curr. Biol. 6:298-304 (1996); Roberts et al., Development 121:31.63-74 (1995)).

Human SHh is synthesized as a 45 kDa precursor protein that upon autocatalytic cleavage yields a 20 kDa N-terminal fragment that, is responsible for normal hedgehog signaling activity; and a 25 kDa C-terminal fragment that is responsible for autoprocessing activity in which the N-terminal fragment is conjugated to a cholesterol moiety (Lee, J. J., et al, (1994) Science 266, 1528-1536; Bumcrot, D. A., et al. (1995), Mol. Cell Biol. 15, 2294-2303; Porter, J. A., et al. (1995) Nature 374, 363-366). The N-terminal fragment consists of amino acid residues 24-197 of the full-length precursor sequence which remains membrane-associated through the cholesterol at its C-terminus (Porter, J. A., et al. (1996) Science 274, 255-258; Porter, J. A., et al. (1995) Cell 86, 21-34). Cholesterol conjugation is responsible for the tissue localization of the hedgehog signal.

At the cell surface, the Hh signal is thought to be relayed by the 12 transmembrane domain protein Patched (Ptc) (Hooper and Scott, Cell 59:751-65 (1989); Nakano et al., Nature 341: 508-13 (1989)) and the G-protein-coupled-like receptor Smoothened (Smo) (Alcedo et al., Cell 86:221-232 (1996); van den Heuvel and Ingham, Nature 382:547-551 (1996)). Both genetic and biochemical evidence support a receptor model where Ptc and Smo are part of a multicomponent receptor complex (Chen and Struhl, Cell 87:553-63 (1996); Marigo et al., Nature 384:176-9 (1996); Stone et al., Nature 384:129-34 (1996)). Upon binding of Hh to Ptc, the normal inhibitory effect of Ptc on Smo is relieved, allowing Smo to transduce the Hh signal across the plasma membrane. However, the exact mechanism by which Ptc controls Smo activity still has yet to be clarified.

The signaling cascade initiated by Smo results in activation of Gli transcription factors that translocate into the nucleus where they control transcription of target genes. Gli has been shown to influence transcription of Hh pathway inhibitors such as Ptc and Hip1 in a negative feedback loop indicating that tight control the Hh pathway activity is required for proper cellular differentiation and organ formation. Uncontrolled activation of Hh signaling pathway are associated with malignancies in particular those of the brain, skin and muscle as well as angiogenesis. An explanation for this is that Hh pathway has been shown to regulate cell proliferation in adults by activation of genes involved in cell cycle progression such as cyclin D which is involved in G1-S transition. Also, SHh blocks cell-cycle arrest mediated by p21, an inhibitor of cyclin dependent kinases. Hh signaling is further implicated in cancer by inducing components in the EGFR pathway (EGF, Her2) involved in proliferation as well as components in the PDGF (PDGFα) and VEGF pathways involved in angiogenesis. Loss of function mutations in the Ptc gene have been identified in patients with the basal cell nevus syndrome (BCNS), a hereditary disease characterized by multiple basal cell carcinomas (BCCs). Dysfunctional Ptc gene mutations have also been associated with a large percentage of sporadic basal cell carcinoma tumors (Chidambaram et al., Cancer Research 56: 4599-601 (1996); Gailani et al., Nature Genet. 14:78-81 (1996); Hahn et al., Cell 85:841-51 (1996); Johnson et al., Science 272:1668-71 (1996); Unden et al., Cancer Res. 56:4562-5; Wicking et al., Am. J. Hum. Genet. 60:21-6 (1997)). Loss of Ptc function is thought to cause an uncontrolled Smo signaling in basal cell carcinoma. Similarly, activating Smo mutations have been identified in sporadic BCC tumors (Xie et al., Nature 391: 90-2 (1998)), emphasizing the role of Smo as the signaling subunit in the receptor complex for SHh.

Various inhibitors of hedgehog signaling have been investigated such as cyclopamine, a natural alkaloid that has been shown to arrest cell cycle at G0-G1 and to induce apoptosis in SCLC. Cyclopamine is believed to inhibit Smo by binding to its heptahelical bundle. Forskolin has been shown to inhibit the Hh pathway downstream from Smo by activating protein kinase A (PICA) which maintains Gli transcription factors inactive. Despite advances with these and other compounds, there remains a need for potent inhibitors of the hedgehog signaling pathway.

SUMMARY OF THE INVENTION

The present invention makes available methods and reagents for inhibiting activation of the hedgehog signaling pathway, e.g., to inhibit aberrant growth states resulting from phenotypes such as pic loss-of-function, hedgehog gain-of-function, or smoothened gain-of-function, comprising contacting the cell with an agent, such as a small molecule, in a sufficient amount to agonize a normal ptc activity, antagonize a normal hedgehog activity, or antagonize smoothened activity, e.g., to reverse or control the aberrant growth state.

One embodiment of the present invention provides a compound represented in the general formula (I):

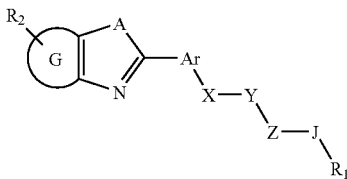

Formula I wherein, as valence and stability permit,

X and Z, independently, represent —N($R_7$)—, —O—, —S—, ($R_7$)N—N($R_7$)—, —ON($R_7$)—, or a direct bond;

Y represents —C(=O)—, —C(=S)—, —C(=N$R_7$)—, $SO_2$, or SO;

A represents O, S, or N$R_7$;

G represents a cycloalkyl, heterocyclyl, aryl, or heteroaryl ring fused to the ring to which it is attached;

Ar represents a substituted or unsubstituted aryl or heteroaryl ring;

$R_1$ represents a disubstituted pyridine ring;

$R_2$ represents from 0-4 substituents on the ring to which it is attached;

$R_7$, independently for each occurrence, represents H, lower alkyl, J-cycloalkyl, J-heterocyclyl, J-aryl, J-heteroaryl;

$R_8$, independently for each occurrence, represents H, lower alkyl, cycloalkyl, heterocyclyl, aryl, or heteroaryl; and J represents, independently for each occurrence, a chain having from 0-8 units selected from $CK_2$, NK, O, and S, wherein K represents, independently for each occurrence, H or lower alkyl.

In certain embodiments, at least one of Z and X is not a direct bond.

In certain embodiments, X—Y—Z includes an amide, urea, or sulfonamide.

In certain embodiments, X is selected from —N($R_8$)—, —O—, —S—, and preferably represents NH.

In certain embodiments, $R_1$ is substituted with a methyl or trifluoromethyl group, e.g., 6-(trifluoromethyl)-2-methylpyridin-3-yl.

In certain embodiments, X and the ring comprising A are disposed on Ar in a meta relationship.

In certain embodiments, $R_2$ represents from 1-4 substituents selected from halogen, lower alkyl, lower alkenyl, aryl, heteroaryl, carbonyl group, thiocarbonyl, ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, J-$R_8$, J-OH, J-lower alkyl, J-lower alkenyl, J-$R_8$, J-SH, J-$NH_2$, protected forms of the above, or any two $R_2$, when occurring more than once in a cyclic or polycyclic structure, can be taken together form a 4- to 8-membered cycloalkyl, aryl, or heteroaryl.

In certain embodiments, $R_2$ represents from 1-4 substituents selected from halogen, cyano, nitro, alkoxy, amino, acylamino (e.g., $R_8$—C(=O)NH—), a substituted or unsubstituted cycloalkyl, heterocyclyl, aryl, or heteroaryl fused to G, and substituted or unsubstituted lower alkyl.

Another embodiment of the present invention provides a method for inhibiting activation of a hedgehog pathway in a cell, comprising contacting the cell with a compound as described above in a sufficient amount to inhibit hedgehog signalling.

In certain such embodiments, the cell has a phenotype of ptc loss-of-function, hedgehog gain-of-function, or smoothened gain-of-function.

In certain such embodiments, the compound inhibits ptc loss-of-function, hedgehog gain-of-function, or smoothened gain-of-function mediated signal transduction with an $ED_{50}$ of 1 μM or less, or even 1 nM or less.

In certain embodiments, the cell is contacted with the hedgehog antagonist in vitro or in vivo.

In certain embodiments, the compound is administered as part of a therapeutic or cosmetic application, such as regulation of neural tissues, bone and cartilage formation and repair, regulation of spermatogenesis, regulation of smooth muscle, regulation of lung, liver and other organs arising from the primative gut, regulation of hematopoietic function, and regulation of skin and hair growth.

Another embodiment of the invention provides et pharmaceutical preparation comprising a sterile pharmaceutical excipient and a compound as described above.

Another embodiment of the invention provides a method for treating or preventing basal cell carcinoma, comprising administering a compound or pharmaceutical preparation as described above to a patient in an amount sufficient to inhibit progression of basal cell carcinoma.

Another embodiment of the invention provides a compound represented in the general formula (I):

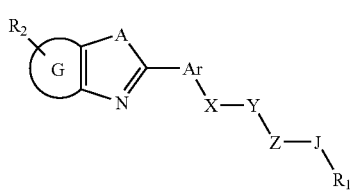

Formula I wherein, as valence and stability permit,

X and Z, independently, represent —N($R_7$)—, —O—, —S—, —($R_7$)N—N($R_7$)—, —ON($R_7$)—, or a direct bond;

Y represents —C(O)—, C(=S)—, —C(=N$R_7$)—, $SO_2$, or SO;

A represents O, S, or N$R_7$;

G represents a cycloalkyl, heterocyclyl, aryl, or heteroaryl ring fused to the ring to which it is attached;

Ar represents a substituted or unsubstituted aryl or heteroaryl ring;

$R_1$ represents a pyridine ring substituted with one or more substituents, wherein at least one of the substituents is selected from the group nitro, cyano, lower alkyl, halogenated lower alkyl, alkenyl, alkynyl, amino, alkylamino, acylamino, amido, hydroxyl, alkoxy, acyloxy, carbonyl, sulfhydryl, or sulfonyl;

$R_2$ represents from 0-4 substituents on the ring to which it is attached;

$R_7$, independently for each occurrence, represents H, lower alkyl, J-cycloalkyl, J-heterocyclyl, J-aryl, J-heteroaryl;

$R_8$, independently for each occurrence, represents H, lower alkyl, cycloalkyl, heterocyclyl, aryl, or heteroaryl; and J represents, independently for each occurrence, a chain having from 0-8 units selected from $CK_2$, NK, O, and S, wherein K represents, independently for each occurrence, H or lower alkyl.

In certain embodiments, at least one of Z and X is not a direct bond.

In certain embodiments, X—Y—Z includes an amide, urea, or sulfonamide.

In certain embodiments, X is selected from —N($R_8$)—, —O—, —S—, and preferably represents NH.

In certain embodiments, $R_1$ is substituted with a methyl or trifluoromethyl group, e.g., $R_1$ is 6-(trifluoromethyl)-2-methylpyridin-3-yl.

In certain embodiments, X and the ring comprising A are disposed on Ar in a meta relationship.

In certain embodiments, $R_2$ represents from 1-4 substituents selected from halogen, lower alkyl, lower alkenyl, aryl, heteroaryl, carbonyl group, thiocarbonyl, ketone, aldehyde, amino, acylamino, amido, amidino, cyano, nitro, azido, sulfonyl, sulfoxide, sulfate, sulfonate, sulfamoyl, sulfonamido, phosphoryl, phosphonate, phosphinate, J-$R_8$, J-OH, J-lower alkyl, J-lower alkenyl, J-$R_8$, J-SH, J-$NH_2$, protected forms of tire above, or any two $R_2$, when occurring more than once in a cyclic or polycyclic structure, can be taken together form a 4- to 8-membered cycloalkyl, aryl, or heteroaryl.

In certain embodiments, $R_2$ represents from 1-4 substituents selected from halogen, cyano, nitro, alkoxy, amino, acylamino (e.g., $R_8$—C(=O)NH—), a substituted or unsubstituted cycloalkyl, heterocyclyl, aryl, or heteroaryl fused to G, and substituted or unsubstituted lower alkyl.

Another embodiment of the present invention provides a method for inhibiting activation of a hedgehog pathway in et cell, comprising contacting the cell with a compound as described above in a sufficient amount to inhibit hedgehog signalling, In certain such embodiments, the cell has a phenotype of ptc loss-of-function, hedgehog gam-of-function, or smoothened gain-of-function.

In certain such embodiments, the compound inhibits ptc loss-of-function, hedgehog gain-of-function, or smoothened gain-of-function mediated signal transduction with an $ED_{50}$ of 1 µM or less, or even 1 nM or less.

In certain embodiments, the cell is contacted with the hedgehog antagonist in vitro or in vivo.

In certain embodiments, the compound is administered as part of a therapeutic or cosmetic application, such as regulation of neural tissues, bone and cartilage formation and repair, regulation of spermatogenesis, regulation of smooth muscle, regulation of lung, liver and other organs arising from the primative gut, regulation of hematopoietic function, and regulation of skin and hair growth.

Another embodiment of the present invention provides a pharmaceutical preparation comprising a sterile pharmaceutical excipient and a compound as described above.

Another embodiment of the present invention provides a method for treating or preventing basal cell carcinoma, comprising administering a compound or pharmaceutical preparation as described above to a patient in an amount sufficient to inhibit progression of basal cell carcinoma.

Another embodiment of the present invention provides a compound represented in the general formula (I):

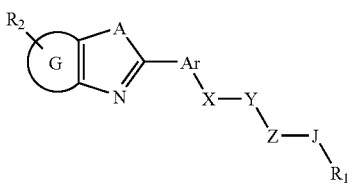

Formula I wherein, as valence and stability permit,

X and Z, independently, represent —N($R_7$)—, —O—, —S—, —($R_7$)N—N($R_7$)—, —ON($R_7$)—, or a direct bond;

Y represents —C(=O)—, —C(=S), —C(=N$R_7$)—, $SO_2$, or SO;

A represents O, S, or $NR_7$;

G represents a cycloalkyl, heterocyclyl, aryl, or heteroaryl ring fused to the ring to which it is attached;

Ar represents a substituted or unsubstituted aryl or heteroaryl ring;

$R_1$ represents a substituted pyridine ring attached to J at a position meta to the nitrogen atom;

$R_2$ represents from 0-4 substituents on the ring to which it is attached;

$R_7$, independently for each occurrence, represents H, lower alkyl, J-cycloalkyl, J-heterocyclyl, J-aryl, J-heteroaryl;

$R_8$, independently for each occurrence, represents H, lower alkyl, cycloalkyl, heterocyclyl, aryl, or heteroaryl; and J represents, independently for each occurrence, a chain having from 0-8 units selected from $CK_2$, NK, O, and S, wherein K represents, independently for each occurrence, H or lower alkyl.

In certain embodiments, at least one of Z and X is not a direct bond.

In certain embodiments, X—Y—Z includes an amide, urea, or sulfonamide.

In certain embodiments, X is selected from —N($R_8$)—, —O—, —S—, and preferably represents NH.

In certain embodiments, $R_1$ is substituted with a methyl or trifluoromethyl group.

In certain embodiments, $R_1$ is 6-(trifluoromethyl)-2-methylpyridin-3-yl.

In certain embodiments, X and the ring comprising A are disposed on Ar in a meta relationship.

In certain embodiments, $R_2$ represents from 1-4 substituents selected from halogen, lower alkyl, lower alkenyl, aryl, heteroaryl, carbonyl group, thiocarbonyl, ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, J-$R_8$, J-OH, J-lower alkyl, J-lower alkenyl, J-$R_8$, J-SH, J-$NH_2$, protected forms of the above, or any two $R_2$, when occurring more than once in a cyclic or polycyclic structure, can be taken together form a 4- to 8-membered cycloalkyl, aryl, or heteroaryl.

In certain embodiments, $R_2$ represents from 1-4 substituents selected from halogen, cyano, nitro, alkoxy, amino, acylamino (e.g., $R_8$—C(=O)NH—), a substituted or unsubstituted cycloalkyl, heterocyclyl, aryl, or heteroaryl fused to G, and substituted or unsubstituted lower alkyl.

Another embodiment of the present invention provides a method for inhibiting activation of a hedgehog pathway in a cell, comprising contacting the cell with a compound as described above in a sufficient amount to inhibit hedgehog signalling.

In certain such embodiments, the cell has a phenotype of ptc loss-of-function, hedgehog gain-of-function, or smoothened gain-of-function.

In certain such embodiments, the compound inhibits ptc loss-of-function, hedgehog gain-of-function, or smoothened gain-of-function mediated signal transduction with an $ED_{50}$ of 1 µM or less, or even 1 nM or less.

In certain embodiments, the cell is contacted with the hedgehog antagonist in vitro or in vivo.

In certain embodiments, the compound is administered as part of a therapeutic or cosmetic application, such as regulation of neural tissues, bone and cartilage formation and repair, regulation of spermatogenesis, regulation of smooth muscle, regulation of lung, liver and other organs arising from the primative gut, regulation of hematopoietic function, and regulation of skin and hair growth.

Another embodiment of the present invention provides a pharmaceutical preparation comprising a sterile pharmaceutical excipient and the compound above.

Another embodiment of the present invention provides a method for treating or preventing basal cell carcinoma, comprising administering a compound or pharmaceutical preparation as described above to a patient in an amount sufficient to inhibit progression of basal cell carcinoma.

DETAINED DESCRIPTION OF THE INVENTION

I. Overview

The present invention relates to the discovery that signal transduction pathways regulated by hedgehog, patched (ptc), gli and/or smoothened can be inhibited, at least in part, by small molecules. While not wishing to be bound by any particular theory, the activation of a receptor may be the mechanism by which these agents act. For example, the ability of these agents to inhibit proliferation of patched loss-of-function ($ptc^{lof}$) cells maybe due to the ability of such molecules to interact with hedgehog, patched, or smoothened, or at least to interfere with the ability of those proteins to activate a hedgehog, ptc, and/or smoothened-mediated signal transduction pathway.

It is, therefore, specifically contemplated that these small molecules which interfere with aspects of hedgehog, ptc, or smoothened signal transduction activity will likewise be capable of inhibiting proliferation (or other biological consequences) in normal cells and/or cells having a patched loss-of-function phenotype, a hedgehog gain-of-function phenotype, or a smoothened gain-of-function phenotype. Thus, it is contemplated that in certain embodiments, these compounds may be useful for inhibiting hedgehog activity in normal cells, e.g., which do not have a genetic mutation that activates the hedgehog pathway. In preferred embodiments, the subject inhibitors are organic molecules having a molecular weight less than 2500 amu, more preferably less than 1500 amu, and even more preferably less than 750 amu, and are capable of inhibiting at least some of the biological activities of hedgehog proteins, preferably specifically in target cells.

Thus, the methods of the present invention include the use of small molecules which agonize ptc inhibition of hedgehog signalling, such as by inhibiting activation of smoothened or downstream components of the signal pathway, in the regulation of repair and/or functional performance of a wide range of cells, tissues and organs, including normal cells, tissues, and organs, as well as those having the phenotype of ptc loss-of-function, hedgehog gain-of-function, or smoothened gain-of-function. For instance, the subject method has therapeutic and cosmetic applications ranging from regulation of neural tissues, bone and cartilage formation and repair, regulation of spermatogenesis, regulation of smooth muscle, regulation of lung, liver and other organs arising from the primative gut, regulation of hematopoietic function, regulation of skin and hair growth, etc. Moreover, the subject methods can be performed on cells that are provided in culture (in vitro), or on cells in a whole animal (in vivo). See, for example, PCT publications WO 95/18856 and WO 96/17924 (the specifications of which are expressly incorporated by reference herein).

In a preferred embodiment, the subject method can be to treat epithelial cells having a phenotype of ptc loss-of-function, hedgehog gain-of-function, or smoothened gain-of-function. For instance, the subject method can be used in treating or preventing basal cell carcinoma or other hedgehog pathway-related disorders.

In certain embodiments, a subject antagonist may inhibit activation of a hedgehog pathway by binding to smoothened. In certain embodiments, a subject antagonist may inhibit activation of a hedgehog pathway by binding to patched.

In another preferred embodiment, the subject method can be used as part of a treatment regimen for malignant medulloblastoma and other primary CNS malignant neuroectodermal tumors.

In another aspect, the present invention provides pharmaceutical preparations comprising, as an active ingredient, a hedgehog antagonist, ptc agonist, or smoothened antagonist such as described herein, formulated in an amount sufficient to inhibit, in vivo, proliferation or other biological consequences of ptc loss-of-function, hedgehog gain-of-function, or smoothened gain-of-function.

The subject treatments using hedgehog antagonists, patched agonists, or smoothened antagonists can be effective for both human and animal subjects. Animal subjects to which the invention is applicable extend to both domestic animals and livestock, raised either as pets or for commercial purposes. Examples are dogs, cats, cattle, horses, sheep, hogs, and goats.

II. Definitions

For convience, certain terms employed in the specification, examples, and appended claims are collected here.

The phrase "aberrant modification or mutation" of a gene refers to such genetic lesions as, for example, deletions, substitution or addition of nucleotides to a gene, as well as gross chromosomal rearrangements of the gene and/or abnormal methylation of the gene. Likewise, mis-expression of a gene refers to aberrant levels of transcription of the gene relative to those levels in a normal cell under similar conditions, as well as non-wild-type splicing of mRNA transcribed from the gene.

"Basal cell carcinomas" exist in a variety of clinical and histological forms such as nodular-ulcerative, superficial, pigmented, morphealike, fibroepithelioma and nevoid syndrome. Basal cell carcinomas are the most common cutaneous neoplasms found in humans. The majority of new cases of nonmelanoma skin cancers fall into this category.

"Burn wounds" refer to cases where large surface areas of skin have been removed or lost from an individual due to heat and/or chemical agents.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Other carcinomatous epithelial growths are "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

The "corium" or "dermis" refers to the layer of the skin deep to the epidermis, consisting of a dense bed of vascular connective tissue, and containing the nerves and terminal organs of sensation. The hair roots, and sebaceous and sweat glands are structures of the epidermis which are deeply embedded in the dermis.

"Dental tissue" refers to tissue in the mouth that is similar to epithelial tissue, for example gum tissue. The method of the present invention is useful for treating periodontal disease.

"Dermal skin ulcers" refer to lesions on the skin caused by superficial loss of tissue, usually with inflammation. Dermal skin ulcers that can be treated by the method of the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

The term "$ED_{50}$" means the dose of a drug that produces 50% of its maximum response or effect.

An "effective amount" of, e.g., a hedgehog antagonist, with respect to the subject method of treatment, refers to an amount of the antagonist in a preparation which, when applied as part of a desired dosage regimen brings about, e.g., a change in the rate of cell proliferation and/or the state of differentiation of a cell and/or rate of survival of a cell according to clinically acceptable standards for the disorder to be treated or the cosmetic purpose.

The terms "epithelia", "epithelial" and "epithelium" refer to the cellular covering of internal and external body surfaces (cutaneous, mucous and serous), including the glands and other structures derived therefrom, e.g., corneal, esophageal, epidermal, and hair follicle epithelial cells. Other exemplary epithlelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, like that which is characteristically found lining hollow organs that are subject to great mechanical change due to contraction and distention, e.g., tissue which represents a transition between stratified squamous and columnar epithelium.

The term "epithelialization" refers to healing by the growth of epithelial tissue over a denuded surface.

The term "epidermal gland" refers to an aggregation of cells associated with the epidermis and specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface.

The term "epidermis" refers to the outermost and nonvascular layer of the skin, derived from the embryonic ectoderm, varying in thickness from 0.07-1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent.

"Excisional wounds" include tears, abrasions, cuts, punctures or lacerations in the epithelial layer of the skin and may extend into the dermal layer and even into subcutaneous fat and beyond. Excisional wounds can result from surgical procedures or from accidental penetration of the skin.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "hair" refers to a threadlike structure, especially the specialized epidermal structure composed of keratin and developing from a papilla sunk in the corium, produced only by mammals and characteristic of that group of animals. Also, "hair" may refer to the aggregate of such hairs. A "hair follicle" refers to one of the tubular-invaginations of the epidermis enclosing the hairs, and from which the hairs grow. "Hair follicle epithelial cells" refers to epithelial cells that surround the dermal papilla in the hair follicle, e.g., stem cells, outer root sheath cells, matrix cells, and inner root sheath cells. Such cells may be normal non-malignant cells, or transformed/immortalized cells.

The term "hedgehog antagonist" refers to an agent that potentiates or recapitulates the bioactivity of patched, such as to repress transcription of target genes. Preferred hedgehog antagonists can be used to overcome a ptc loss-of-function and/or a smoothened gain-of-function, the latter also being referred to as smoothened antagonists. The term "hedgehog antagonist" as used herein refers not only to any agent that may act by directly inhibiting the normal function of the hedgehog protein, but also to any agent that inhibits the hedgehog signalling pathway, and thus recapitulates the function of ptc.

The term "hedgehog gain-of-function" refers to an aberrant modification or mutation of a ptc gene, hedgehog gene, or smoothened gene, or a decrease (or loss) in the level of expression of such a gene, which results in a phenotype which resembles contacting a cell with a hedgehog protein, e.g., aberrant activation of a hedgehog pathway. The gain-of-function may include a loss of the ability of the ptc gene product to regulate the level of expression of Ci genes, e.g., Gli1, Gli2, and Gli3. The term 'gain-of-function' is also used herein to refer to any similar cellular phenotype (e.g., exhibiting excess proliferation) that occurs due to an alteration anywhere in the hedgehog signal transduction pathway, including, but not limited to, a modification or mutation of hedgehog itself. For example, a tumor cell with an abnormally high proliferation rate due to activation of the hedgehog signalling pathway would have a 'hedgehog gain-of-function' phenotype, even if hedgehog is not mutated in that cell.

As used herein, "immortalized cells" refers to cells that have been altered via chemical and/or recombinant means such that the cells have the ability to grow through an indefinite number of divisions in culture.

"Internal epithelial tissue" refers to tissue inside the body that has characteristics similar to the epidermal layer in the skin. Examples include the lining of the intestine. The method of the present invention is useful for promoting the healing of certain internal wounds, for example wounds resulting from surgery.

The term "keratosis" refers to proliferative skin disorder characterized by hyperplasia of the horny layer of the epidermis. Exemplary keratotic disorders include keratosis follicularis, keratosis palmaris et plantaris, keratosis pharyngea, keratosis pilaris, and actinic keratosis.

The term "$LD_{50}$" means the dose of a drug that is lethal in 50% of test subjects.

The term "nail" refers to the horny cutaneous plate on the dorsal surface of the distal end of a finger or toe.

The term "patched loss-of-function" refers to an aberrant modification or mutation of a ptc gene, or a decreased level of expression of the gene, which results in a phenotype which resembles contacting a cell with a hedgehog protein, e.g., aberrant activation of a hedgehog pathway. The loss-of-function may include a loss of the ability of the ptc gene product to regulate the level of expression of Ci genes, e.g., Gli1, Gli2 and Gli3. The term 'ptc loss-of-function' is also used herein to refer to any similar cellular phenotype (e.g., exhibiting excess proliferation) that occurs due to an alteration anywhere in the hedgehog signal transduction pathway, including, but not limited, to, a modification or mutation of ptc itself. For example, a tumor cell with an abnormally high proliferation rate due to activation of the hedgehog signalling path-way would have a 'ptc loss-of-function' phenotype, even if ptc is not mutated in that cell.

A "patient" or "subject" to be treated by the subject method can mean either a human or non-human animal.

The term "preventing" is art-recognized, and when used in relation to a condition, such as a local recurrence (e.g., pain), a disease such as cancer, a syndrome complex such as heart failure or any other medical condition, is well understood in the art, and includes administering, prior to onset of the condition, a composition that reduces the frequency of, reduces the severity of, or delays the onset of symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the frequency of, reducing the severity of, or alternatively delaying, pain sensations experienced by subjects in a treated population versus an untreated control population.

The phrase "pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

The phrase "pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

As used herein, "proliferating" and "proliferation" refer to cells undergoing mitosis.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis. Another example is "epidermolysis", which refers to a loosened state of the epidermis with formation of blebs and bullae either spontaneously or at the site of trauma.

As used herein, the term "psoriasis" refers to a hyperproliferative skin disorder that alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The phrase "and salts and solvates thereof" as used herein means that compounds of the inventions may exist in one or a mixture of salts and solvate forms. For example a compound of the invention may be substantially pure in one particular salt or solvate form or else may be mixtures of two or more salt or solvate forms.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "smoothened gain-of-function" refers to an aberrant modification or mutation of a smo gene, or an increased level of expression of the gene, which results in a phenotype that resembles contacting a cell with a hedgehog protein, e.g., aberrant activation of a hedgehog pathway. While not wishing to be bound by any particular theory, it is noted that ptc may not signal directly into the cell, but rather interact with smoothened, another membrane-bound protein located downstream of ptc in hedgehog signaling (Marigo et al, (1996) Nature 384:177-179). The gene smo is a segment-polarity gene required for the correct patterning of every segment in Drosophila (Alcedo et al, (1996) Cell 86:221-232). Human homologs of smo have been identified. See, for example, Stone et al. (1996) Nature 384:129-134, and Gen-Bank accession U84401. The smoothened gene encodes an integral membrane protein with characteristics of heterotrimeric G-protein-coupled receptors; i.e., 7-transmembrane regions. This protein shows homology to the Drosophila Frizzled (Fz) protein, a member of the wingless pathway. It was originally thought that smo encodes a receptor of the Hh signal. However, this suggestion was subsequently disproved, as evidence for ptc being the Hh receptor was obtained. Cells that express Smo fail to bind Hh, indicating that smo does not interact directly with Hh (Nusse, (1996) Nature 384:119-120). Rather, the binding of Sonic hedgehog (SHH) to its receptor, PTCH, is thought to prevent normal inhibition by PTCH of smoothened (SMO), a seven-span transmembrane protein.

Recently, it has been reported that activating smoothened mutations occur in sporadic basal cell carcinoma, Xie et al. (1998) Nature 391:90-2, and primitive neuroectodermal tumors of the central nervous system, Reifenberger et al. (1998) Cancer Res 58:1798-803.

The term "therapeutic index" refers to the therapeutic index of a drag defined as $LD_{50}/ED_{50}$.

As used herein, "transformed cells" refers to cells that have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

The term "treating" as used herein includes prophylaxis of the named condition or amelioration or elimination of the condition once it has been established.

The term "acyl" means a carbonyl containing substituent represented by the formula —C(O)—R in which R is alkyl, a carbocycle, a heterocycle, carbocycle-substituted alkyl or heterocycle-substituted alkyl wherein alkyl, carbocycle and heterocycle are as herein defined. Acyl groups include alkanoyl (e.g. acetyl), aroyl (e.g. benzoyl), and heteroaroyl.

The term "acylamino" is art-recognized and refers to a moiety that can be represented by the general formula:

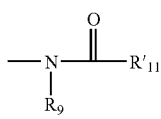

wherein $R_9$ is as defined above, and $R'_{11}$ represents a hydrogen, an alkyl, an alkenyl or —$(CH_2)_m$—$R_8$, where m and $R_8$ are as defined above.

The term "acyloxy" is art-recognized and refers to a moiety that can be represented by the general formula:

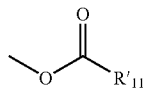

wherein $R'_{11}$ represents a hydrogen, an alkyl, an alkenyl or —$(CH_2)_m$—$R_8$, where m and $R_8$ are as defined above.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamide, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethylthio, and the like.

The terms "amine" and "amino" are art-recognized and refer to both unsubstituted and substituted amines, e.g., a moiety that can be represented by the general formula:

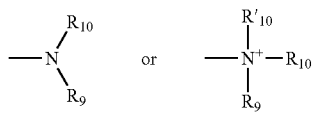

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In certain such embodiments, neither $R_9$ and $R_{10}$ is attached to N by a carbonyl, e.g., the amine is not an amide or imide, and the amine is preferably basic, e.g., its conjugate acid has a $pK_a$ above 7. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Preferred amino protecting groups are Boc, Fmoc and Cbz. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino" refers to an amino group substituted with one of the above amino-protecting groups.

The term "amido" is art-recognized as an amino-substituted carbonyl and includes a moiety that can be represented by the general formula:

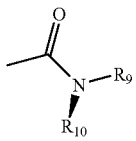

wherein $R_9$, $R_{10}$ are as defined above. Preferred embodiments of the amide will not include imides that may be unstable.

The term "amidine" denotes Hie group —C(NH)—NHR wherein R is H or alkyl or aralkyl. A preferred amidine is the group —C(NH)—$NH_2$. The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases, such as lithium hydroxide or NaOH, or reductive conditions employing highly activated metal hydrides such as $LiAlH_4$. (Such harsh removal conditions are also to be avoided when removing amino-protecting groups and hydroxy-protecting groups, discussed below.) Preferred carboxylic acid protecting groups are the alkyl (e.g. methyl, ethyl, t-butyl), allyl, benzyl and p-nitrobenzyl groups. Similar carboxy-protecting groups used in the cephalosporin, penicillin and peptide arts can also be used to protect a carboxy group substituents. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

The term "carbonyl" is art-recognized and includes such moieties as can be represented by the general formula:

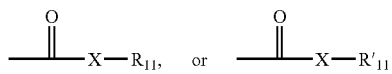

wherein X is a bond or represents an oxygen or a sulfur, and $R_{11}$ represents a hydrogen, an alkyl, an alkenyl, $-(CH_2)_m-R_8$ or a pharmaceutically acceptable salt, $R'_{11}$ represents a hydrogen, an alkyl, an alkenyl or $-(CH_2)_m-R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term guanidine" denotes the group $-NH-C(NH)-NHR$ wherein R is H or alkyl or aralkyl. A particular guanidine group is $-NH-C(NH)-NH_2$.

The term "heteroatom" as used herein means an atom of any element other than carbon or hydrogen. Preferred heteroatoms are boron, nitrogen, oxygen, phosphorus, sulfur and selenium.

The terms "heterocycle," "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

The term "hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g. TBS, TBDPS) groups. Further examples of these groups are found in T. W. Greene and P. G. M. Wuts, "Protective Groups in Organic Synthesis", $2^{nd}$ ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected hydroxy" refers to a hydroxy group substituted with one of the above hydroxy-protecting groups.

As used herein, the term "nitro" means $-NO_2$; the term "halogen" designates $-F$, $-Cl$, $-Br$ or $-I$; the term "sulfhydryl" means $-SH$; the term "hydroxyl" means $-OH$; and the term "sulfonyl" means $-SO_2-$.

A "phosphonamidite" can be represented in the general formula:

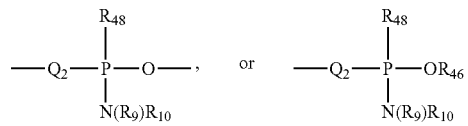

wherein $R_9$ and $R_{10}$ are as defined above, $Q_2$ represents O, S or N, and $R_{48}$ represents a lower alkyl or an aryl, $Q_2$ represents O, S or N.

A "phosphoramidite" can be represented in the general formula:

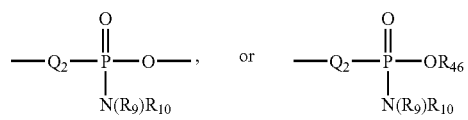

wherein $R_9$ and $R_{10}$ are as defined above, and $Q_2$ represents O, S or N.

A "phosphoryl" can in general be represented by the formula:

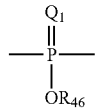

wherein $Q_1$ represented S or O, and $R_{46}$ represents hydrogen, a lower alkyl or an aryl. When used to substitute, for example, an alkyl, the phosphoryl group of the phosphorylalkyl can be represented by the general formula:

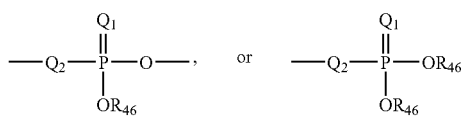 or 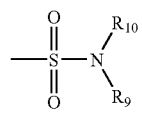

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

A "selenoalkyl" refers to an alkyl group having a substituted seleno group attached thereto. Exemplary "selenoethers" which may be substituted on the alkyl are selected from one of —Se-alkyl, —Se-alkenyl, Se-alkynyl and —Se—$(CH_2)_m$—$R_8$, m and $R_8$ being defined above.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation, such as by rearrangement, cyclization, elimination, etc.

The term "sulfamoyl" is art-recognized and includes a moiety that can be represented by the general formula:

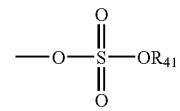

in which $R_9$ and $R_{10}$ are as defined above.

The term "sulfate" is art recognized and includes a moiety that can be represented by the general formula:

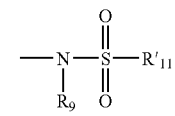

in which $R_{41}$ is as defined above.

The term "sulfonamido" is art recognized and includes a moiety that can be represented by the general formula:

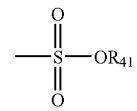

in which $R_9$ and $R'_{11}$ are as defined above.

The term "sulfonate" is art-recognized and includes a moiety that can be represented by the general formula:

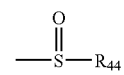

in which $R_{41}$ is an electron pair, hydrogen, alkyl, cycloalkyl, or aryl.

The terms "sulfoxido" or "sulfinyl", as used herein, refers to a moiety that can be represented by the general formula:

$$\overset{O}{\underset{}{\overset{\|}{-S}}}-R_{44}$$

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

Certain compounds of the present invention may exist in particular geometric or stereoisomers forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., the ability to inhibit hedgehog signaling), wherein one or more simple variations of substituents are made which do not adversely affect the efficacy of the compound. In general, the compounds of the present invention may be prepared by the methods illustrated in the general reaction schemes as, for example, described below, or by modifications thereof, rising readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

III. Exemplary Compounds of the Invention

As described in further detail below, it is contemplated, that the subject methods can be earned out using a variety of different small molecules which can be readily identified, for example, by such drug screening assays as described herein.

For example, compounds useful in the subject methods include compounds may be represented by general formula (I):

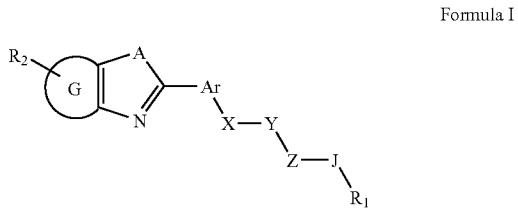

Formula I wherein, as valence and stability permit,

X and Z, independently, represent —N($R_7$)—, —O—, —S—, —($R_7$)N—N($R_7$)—, —ON($R_7$)—, or a direct bond, preferably —N($R_7$)—, —O—, —S—, or a direct bond;

Y represents —C(=O)—, —C(=S)—, —C(=N$R_7$)—, $SO_2$, or SO, preferably C(=O)—, $SO_2$, or —C(=S)—;

A represents O, S, or N$R_7$, preferably O or NH, and roost preferably NH;

G represents a cycloalkyl, heterocyclyl, aryl, or heteroaryl ring fused to the ring to which it is attached, preferably an aryl or heteroaryl ring.

Ar represents a substituted or unsubstituted aryl or heteroaryl ring, such as a substituted or unsubstituted phenyl ring;

$R_1$ represents a substituted or unsubstituted pyridine ring;

$R_2$ represents from 0-4 substituents on the ring to which it is attached, such as halogen, lower alkyl, lower alkenyl, aryl, heteroaryl, carbonyl group (e.g., ester, carboxyl, or formyl), thiocarbonyl (e.g., thioester, thiocarboxylate, or thioformate), ketone, aldehyde, amino, acylamino, amido, amidino, cyano, nitro, azido, sulfonyl, sulfoxide, sulfate, sulfonate, sulfamoyl, sulfonamide, phosphoryl, phosphonate, phosphinate, J-$R_8$, J-OH, J-lower alkyl, J-lower alkenyl, J-$R_8$, J-SH, J-$NH_2$, protected forms of the above, or any two $R_2$, when occurring more than once in a cyclic or polycyclic structure, can be taken together form a 4- to 8-membered cycloalkyl, aryl, or heteroaryl;

$R_7$, independently for each occurrence, represents H, lower alkyl (e.g., substituted or unsubstituted), J-cycloalkyl (e.g., substituted or unsubstituted), J-heterocyclyl (e.g., substituted or unsubstituted), J-aryl (e.g., substituted or unsubstituted), J-heteroaryl (e.g., substituted, or unsubstituted);

$R_8$, independently for each occurrence, represents H, lower alkyl (e.g., substituted or unsubstituted), cycloalkyl (e.g., substituted or unsubstituted), heterocyclyl (e.g., substituted or unsubstituted), aryl (e.g., substituted or unsubstituted), or heteroaryl (e.g., substituted or unsubstituted); and J represents, independently for each occurrence, a chain having from 0-8 (preferably from 0-4) units selected from $CK_2$, NK, O, and S, wherein K represents, independently for each occurrence, H or lower alkyl.

In certain embodiments, at least one of Z and X is not a direct bond. In certain embodiments, X—Y—Z includes an amide, urea, or sulfonamide. In certain embodiments, X is selected from —N($R_8$)—, —O—, —S—, and preferably represents NH.

In certain embodiments, $R_1$ is a pyridine ring, optionally substituted with from 1-5 substituents, such as nitro, halogen, cyano, lower alkyl (such as methyl or halogenated lower alkyl (such as trifluoromethyl)), alkenyl, alkynyl, aralkyl, amino, alkylamino, acylamino (e.g., $R_8$—C(=O)NH—), amido, hydroxyl, alkoxy, acyloxy (e.g., $R_8$—C(=O)—O—), carbonyl, phosphoryl, sulfamoyl, sulfate, sulfonamide, sulfonate, sulfoxido, sulfhydryl, sulfonyl, a substituted or unsubstituted cycloalkyl, heterocyclyl, aryl, or heteroaryl fused to the pyridine ring. In certain embodiments, $R_1$ is a pyridine ring, optionally substituted with from 1-5 substituents, such as nitro, cyano, lower alkyl (such as methyl or halogenated lower alkyl (such as trifluoromethyl)), alkenyl, alkynyl, aralkyl, amino, alkylamino, acylamino (e.g., $R_8$—C(=O)NH—), amido, hydroxyl, alkoxy, acyloxy (e.g., $R_8$—C(=O)—O—), carbonyl, phosphoryl, sulfamoyl, sulfate, sulfonamide, sulfonate, sulfoxide, sulfhydryl, or sulfonyl. In certain embodiments, one or more of the substituents on the pyridine ring is bound to a protecting group. In some embodiments, the pyridine ring is substituted with a methyl, trifluoromethyl, or both.

The pyridine ring of $R^1$ can be substituted at any position on the ring, for example ortho, meta or para to the nitrogen atom of the pyridine ring. In some embodiments, the pyridine ring is substituted with two substituents in addition to J (disubstituted). These two substituents can have any positional relationship with respect to one another allowed by the pyridine ring. For example, these substituents can be in a ortho relationship to each other (e.g., 2,3; 3,4; 4,5; or 5,6). They can have a meta relationship to each other (e.g., 2,4; 2,6; 3,5; or 4,6). Or they can have a para relationship (e.g., 2,5; or 3,6). In other embodiments, the pyridine ring is substituted with three substituents in addition to J (trisubstituted). These substituents also can have any positional relationship respect to one another allowed by the pyridine ring. In yet other embodiments, the pyridine ring is substituted with four substituents in addition to J (tetrasubstituted). These substituents also can have any positional relationship respect to one another allowed by the pyridine ring.

In certain embodiments the pyridine ring of $R_1$ can be substituted on a position orthro to the nitrogen atom. In further embodiments, the pyridine ring can be substituted at both positions ortho to the nitrogen atom. The pyridine ring can have either position ortho to the nitrogen atom substituted by a methyl or trifluoromethyl. In another embodiment, one position ortho to the nitrogen of the pyridine ring is substituted with methyl and the other position ortho to the nitrogen is substituted with trifluoromethyl.

The pyridine ring of $R_1$ can be connected to J at any position on the ring. For example, the pyridine ring can be connected to J ortho to the nitrogen atom of the pyridine ring (the C2 position, i.e., a 2-pyridyl ring), meta to the nitrogen atom of the pyridine ring (the C3 position, i.e., a 3-pyridyl ring), or para to the nitrogen atom of the pyridine ring (the C4 position, i.e., a 4-pyridyl ring). The different positions for connection to J can be contemplated with the diverse substitution possibilities disclosed above. For example, in one embodiment, the pyridine ring is connected to J meta to the nitrogen atom and the ring is substituted with two additional substituents (disubstituted), such as methyl and trifluoromethyl.

The nitrogen atom of the pyridine ring of $R_1$ may also be substituted with heteroatoms, such as oxygen (e.g., producing a nitrone or N-oxide). Substitution of the nitrogen atom of the pyridine ring may be in combination with additional substitution on the pyridine ring.

In certain embodiments, X and the ring comprising A are disposed on Ar in a meta (i.e., 1,3) relationship.

In certain embodiments, G represents a phenyl or piperidine ring.

In certain embodiments, J is absent.

In certain embodiments, $R_2$ represents from 1-4 substituents selected from halogen, cyano, nitro, alkoxy, amino, acylamino (e.g., $R_8$—C(=O)NH—), a substituted or unsubstituted cycloalkyl, heterocyclyl, aryl, or heteroaryl fused to G, and substituted or unsubstituted lower alkyl.

In certain embodiments, compounds useful in the present invention may be represented by general formula (II):

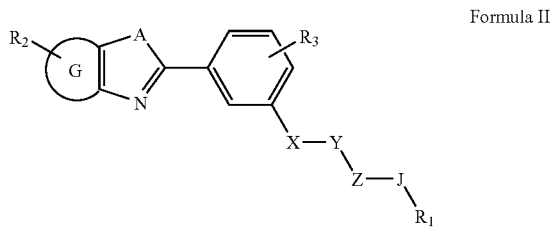

Formula II wherein, as valence and stability permit,

X and Z, independently, represent —N($R_7$)—, —O—, —S—, —($R_7$)N—N($R_7$)—, —ON($R_7$)—, or a direct bond, preferably —N($R_7$)—, —O—, —S—, or a direct bond;

Y represents —C(=O)—, —C(=S)—, —C(=N$R_7$)—, $SO_2$, or SO, preferably —C(=O)—, $SO_2$, or —C(=S)—;

A represents O, S, or N$R_7$, preferably O or NH, and most preferably NH;

G represents a cycloalkyl, heterocyclyl, aryl, or heteroaryl ring fused to the ring to which it is attached, preferably an aryl or heteroaryl ring.

$R_1$ represents a substituted or unsubstituted pyridine ring;

$R_2$ represents from 0-4 substituents on the ring to which it is attached, such as halogen, lower alkyl, lower alkenyl, aryl, heteroaryl, carbonyl group (e.g., ester, carboxyl, or formyl), thiocarbonyl (e.g., thioester, thiocarboxylate, or thioformate), ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, J-$R_8$, J-OH, J-lower alkyl, J-lower alkenyl, J-$R_8$, J-SH, J-$NH_2$, protected forms of the above, or any two $R_2$, when occurring more than once in a cyclic or polycyclic structure, can be taken together form a 4- to 8-membered cycloalkyl, aryl, or heteroaryl;

$R_3$ represents from 0-4 substituents on the ring to which it is attached, such as halogen, hydroxyl, alkoxy, amino, alkylamino, cyano, nitro, substituted or unsubstituted lower alkyl, and acyl, preferably halogen, lower alkoxy, or substituted or unsubstituted lower alkyl;

$R_7$, independently for each occurrence, represents H, lower alkyl (e.g., substituted or unsubstituted), J-cycloalkyl (e.g., substituted or unsubstituted), J-heterocyclyl (e.g., substituted or unsubstituted), J-aryl (e.g., substituted or unsubstituted), J-heteroaryl (e.g., substituted or unsubstituted);

$R_8$, independently for each occurrence, represents H, lower alkyl (e.g., substituted or unsubstituted), cycloalkyl (e.g., substituted or unsubstituted), heterocyclyl (e.g., substituted or unsubstituted), aryl (e.g., substituted or unsubstituted), or heteroaryl (e.g., substituted or unsubstituted); and J represents, independently for each occurrence, a chain having from 0-8 (preferably from 0-4) units selected from $CK_2$, NK, O, and S, wherein K represents, independently for each occurrence, H or lower alkyl.

In certain embodiments, at least one of Z and X is not a direct bond. In certain embodiments, X—Y—Z includes an amide, urea, or sulfonamide. In certain embodiments, X is selected from —N($R_8$)—, —O—, —S—, and preferably represents NH.

In certain embodiments, $R_1$ includes a pyridine ring, optionally substituted with from 1-5 substituents, such as nitro, halogen, cyano, lower alkyl, acylamino (e.g., $R_8$—C (=O)NH—), alkoxy, alkylamino, a substituted or unsubstituted cycloalkyl, heterocyclyl, aryl, or heteroaryl fused to the pyridine, ring. In some embodiments, the pyridine ring is connected to J at the C3 position (i.e., a 3-pyridyl ring). In some embodiments, the pyridine ring may be substituted at the C2 position, the C6 position, or both. In some embodiments, the pyridine ring is substituted with a methyl group or a trifluoromethyl group or both.

In certain embodiments, G represents a phenyl or piperidine ring.

In certain embodiments, J is absent.

In certain embodiments, $R_2$ represents from 1-4 substituents selected from halogen, cyano, nitro, alkoxy, amino, acylamino (e.g., $R_8$—C(=O)NH—), a substituted or unsubstituted cycloalkyl, heterocyclyl, aryl, or heteroaryl fused to G, and substituted or unsubstituted lower alkyl.

In certain embodiments, $R_3$ includes a substituent, such as a substituted or unsubstituted alkyl or a halogen, at a position para either to X or to the ring including A.

As described in further detail below, it is contemplated that the subject methods can be carried out using a variety of different small molecules which can be readily identified, for example, by such drug screening assays as described herein. For example, compounds useful in the subject methods include compounds may be represented by general formula (III):

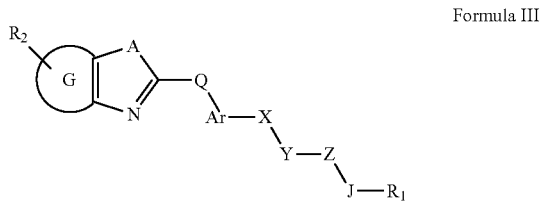

Formula III wherein, as valence and stability permit,

X and Z, independently, represent —N($R_7$)—, —O—, —S—, —($R_7$)N—N($R_7$)—, —ON($R_7$)—, or a direct bond, preferably —N($R_7$)—, —O—, —S—, or a direct bond;

Y represents —C(=O)—, —C(=S)—, —C(=N$R_7$)—, $SO_2$, or SO, preferably —C(=O), $SO_2$, or —C(=S)—;

A represents O, S, or N$R_7$, preferably O or NH, and most preferably NH;

G represents a cycloalkyl, heterocyclyl, aryl, or heteroaryl ring fused to the ring to which it is attached, preferably an aryl or heteroaryl ring;

Q is absent, or represents $CK_2$, NK, O, and S, wherein K represents, independently for each occurrence, H or lower alkyl;

Ar represents a substituted or unsubstituted aryl or heteroaryl ring, such as a substituted or unsubstituted phenyl ring;

$R_1$ represents a substituted or unsubstituted pyridine ring;

$R_2$ represents from 0-4 substituents on the ring to which it is attached, such as halogen, lower alkyl, lower alkenyl, aryl, heteroaryl, carbonyl group (e.g., ester, carboxyl, or formyl), thiocarbonyl (e.g., thioester, thiocarboxylate, or thioformate), ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, J-$R_8$, J-OH, J-lower alkyl, J-lower alkenyl, J-$R_8$, J-SH, J-$NH_2$, protected forms of the above, or any two $R_2$, when occurring more than once in a cyclic or polycyclic structure, can be taken together form a 4- to 8-membered cycloalkyl, aryl, or heteroaryl;

$R_7$, independently for each occurrence, represents H, lower alkyl (e.g., substituted or unsubstituted), J-cycloalkyl (e.g., substituted or unsubstituted), J-heterocyclyl (e.g., substituted or unsubstituted), J-aryl (e.g., substituted or unsubstituted), J-heteroaryl (e.g., substituted or unsubstituted);

$R_8$, independently for each occurrence, represents H, lower alkyl (e.g., substituted or unsubstituted), cycloalkyl (e.g., substituted or unsubstituted), heterocyclyl (e.g., substituted or unsubstituted), aryl (e.g., substituted or unsubstituted), or heteroaryl (e.g., substituted or unsubstituted); and J represents, independently for each occurrence, a chain having from 0-8 (preferably from 0-4) units selected from $CK_2$, NK, O, and S.

In certain embodiments, at least one of Z and X is not a direct bond. In certain embodiments, X—Y—Z includes an amide, urea, or sulfonamide. In certain embodiments, X is selected, from —N($R_8$)—, —O—, —S—, and preferably represents NH.

In certain embodiments, $R_1$ includes a pyridine ring, optionally substituted with from 1-5 substituents, such as nitro, halogen, cyano, lower alkyl, acylamino (e.g., $R_8$—C(=O)NH—), alkoxy, alkylamino, a substituted or unsubstituted cycloalkyl, heterocyclyl, aryl, or heteroaryl fused to the pyridine ring. In some embodiments, the pyridine ring is connected to J at the C3 position (i.e., a 3-pyridyl ring). In some embodiments, the pyridine ring may be further substituted at the C2 position or at the C6 position or both. In some embodiments the pyridine ring is substituted with a methyl group or a trifluoromethyl group or both.

In certain embodiments, X and the ring comprising A are disposed on Ar in a meta (i.e., 1,3) relationship.

In certain embodiments, G represents a phenyl or piperidine ring.

In certain embodiments, J is absent.

In certain embodiments, $R_2$ represents from 1-4 substituents selected from halogen, cyano, nitro, alkoxy, amino, acylamino (e.g., $R_8$—C(=O)NH—), a substituted or unsubstituted cycloalkyl, heterocyclyl, aryl, or heteroaryl fused to G, and substituted or unsubstituted lower alkyl.

In certain embodiments, compounds useful in the present invention may be represented by general formula (IV):

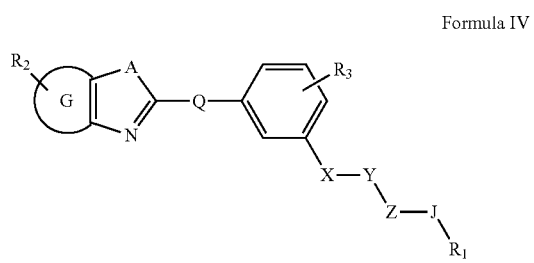

Formula IV wherein, as valence and stability permit,

X and Z, independently, represent —N($R_7$)—, —O—, —S—, —($R_7$)N—N($R_7$)—, —ON($R_7$)—, or a direct bond, preferably —N($R_7$)—, —O—, —S—, or a direct bond;

Y represents —C(=O)—, C(=S), —C(=N$R_7$)—, $SO_2$, or SO, preferably —C(=O)—, $SO_2$, or —C(=S)—;

A represents O, S, or N$R_7$, preferably O or NH, and most preferably NH;

G represents a cycloalkyl, heterocyclyl, aryl, or heteroaryl ring fused to the ring to which it is attached, preferably an aryl or heteroaryl ring.

Q is absent, or represents $CK_2$, NK, O, and S, wherein K represents, independently for each occurrence, H or lower alkyl;

$R_1$ represents a substituted or unsubstituted pyridine ring;

$R_2$ represents from 0-4 substituents on the ring to which it is attached, such as halogen, lower alkyl, lower alkenyl, aryl, heteroaryl, carbonyl group (e.g., ester, carboxyl, or formyl), thiocarbonyl (e.g., thioester, thiocarboxylate, or thioformate), ketone, aldehyde, amino, acylamino, amido, amidino, cyano, nitro, azido, sulfonyl, sulfoxido, sulfate, sulfonate, sulfamoyl, sulfonamide, phosphoryl, phosphonate, phosphinate, $J-R_8$, J-OH, J-lower alkyl, J-lower alkenyl, $J-R_8$, J-SH, $J-NH_2$, protected forms of the above, or any two $R_2$, when occurring more than once in a cyclic or polycyclic structure, can be taken together form a 4- to 8-membered cycloalkyl, aryl, or heteroaryl;

$R_3$ represents from 0-4 substituents on the ring to which, it is attached, such as halogen, hydroxyl, alkoxy, amino, alkylamino, cyano, nitro, substituted or unsubstituted lower alkyl, and acyl, preferably halogen, lower alkoxy, or substituted or unsubstituted lower alkyl;

$R_7$, independently for each occurrence, represents H, lower alkyl (e.g., substituted or unsubstituted), J-cycloalkyl (e.g., substituted or unsubstituted), J-heterocyclyl (e.g., substituted or unsubstituted), J-aryl (e.g., substituted or unsubstituted), J-heteroaryl (e.g., substituted or unsubstituted);

$R_8$, independently for each occurrence, represents H, lower alkyl (e.g., substituted or unsubstituted), cycloalkyl (e.g., substituted or unsubstituted), heterocyclyl (e.g., substituted or unsubstituted), aryl (e.g., substituted or unsubstituted), or heteroaryl (e.g., substituted or unsubstituted); and J represents, independently for each occurrence, a chain having from 0-8 (preferably from 0-4) units selected from $CK_2$, NK, O, and S.

In certain embodiments, at least one of Z and X is not a direct bond. In certain embodiments, X—Y—Z includes an amide, urea, or sulfonamide. In certain embodiments, X is selected from —N($R_8$)—, —O—, —S—, and preferably represents NH.

In certain embodiments, $R_1$ includes a pyridine ring, optionally substituted with from 1-5 substituents, such as nitro, halogen, cyano, lower alkyl, acylamino (e.g., $R_8$—C(=O)NH—), alkoxy, alkylamino, a substituted or unsubstituted cycloalkyl, heterocyclyl, aryl, or heteroaryl fused to the pyridine ring. In some embodiments, the pyridine ring is connected to J at the C3 position (i.e., a 3-pyridyl ring). In some embodiments the pyridine ring may be further substituted at the C2 position or at the C6 position or both. In some embodiments, the pyridine ring is substituted with a methyl group or a trifluoromethyl group or both.

In certain embodiments, G represents a phenyl or piperidine ring.

In certain embodiments, J is absent.

In certain embodiments, $R_2$ represents from 1-4 substituents selected from halogen, cyano, nitro, alkoxy, amino, acylamino (e.g., $R_8$—C(=O)NH—), a substituted or unsubstituted cycloalkyl, heterocyclyl, aryl, or heteroaryl fused to G, and substituted or unsubstituted lower alkyl.

In certain embodiments, $R_3$ includes a substituent, such as a substituted or unsubstituted alkyl or a halogen, at a position para either to X or to the ring including A.

In certain embodiments, the subject antagonists can be chosen on the basis of their selectively for the hedgehog pathway. This selectivity can be for the hedgehog pathway versus other pathways, or for selectivity between particular hedgehog pathways, e.g., ptc-1, ptc-2, etc.

In certain preferred embodiments, the subject inhibitors inhibit ptc loss-of-function, hedgehog gain-of-function, or smoothened gain-of-function mediated signal transduction with an $ED_{50}$ of 1 mM or less, more preferably of 1 µM or less, and even more preferably of 1 nM or less. Similarly, in certain preferred embodiments, the subject inhibitors inhibit activity of the hedgehog pathway with a $K_i$ less than 10 nM, preferably less than 1 nM, even more preferably less than 0.1 nM.

In particular embodiments, the small molecule is chosen for use because it is more selective for one patched isoform over the next, e.g., 10-fold, and more preferably at least 100- or even 1000-fold more selective for one patched pathway (ptc-1, ptc-2) over another.

In certain embodiments, a compound which is an antagonist of the hedgehog pathway is chosen to selectively antagonize hedgehog activity over protein kinases other than PKA, such as PKC, e.g., the compound modulates the activity of the hedgehog pathway at least an order of magnitude more strongly than it modulates the activity of another protein kinase, preferably at least two orders of magnitude more strongly, even more preferably at least three orders of magnitude more strongly. Thus, for example, a preferred inhibitor of the hedgehog pathway may inhibit hedgehog activity with a $K_i$ at least an order of magnitude lower than its $K_i$ for inhibition of PKC, preferably at least two orders of magnitude lower, even more preferably at least three orders of magnitude lower. In certain embodiments, the $K_i$ for PKA inhibition is less than 10 nM, preferably less than 1 nM, even more preferably less than 0.1 nM.

It is readily appreciated that any and all combinations of features presented in embodiments disclosed above are contemplated to be within the scope of the present invention.

IV. Exemplary Applications of Method and Compositions

Another aspect of the present invention relates to a method of modulating a differentiated state, survival, and/or proliferation of a cell having a ptc loss-of-function, hedgehog gain-of-function, or smoothened gain-of-function, by contacting the cells with a hedgehog antagonist according to the subject method and as the circumstances may warrant.

For instance, it is contemplated by the invention that, in light of the findings of an apparently broad involvement of hedgehog, ptc, and smoothened in the formation of ordered spatial arrangements of differentiated tissues in vertebrates, the subject method could be used as part of a process for generating and/or maintaining an array of different vertebrate tissue both in vitro and in vivo. The hedgehog antagonist, whether inductive or anti-inductive with respect proliferation or differentiation of a given tissue, can be, as appropriate, any of the preparations described above.

For example, the present method is applicable to cell culture techniques wherein, whether for genetic or biochemical reasons, the cells have a ptc loss-of-function, hedgehog gain-of-function, or smoothened gain-of-function phenotype. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNP). One use of the present method may be in cultures of neuronal stem cells, such as in the use of such cultures for the generation of new neurons and glia. In such embodiments of the subject method, the cultured cells can be contacted with a hedgehog antagonist of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motor-neurons. Such neuronal cultures can be used as convenient assay systems as well as sources of implantable cells for therapeutic treatments.

According to the present invention, large numbers of non-tumorigenic neural progenitor cells can be perpetuated in vitro and their rate of proliferation and/or differentiation can be affected by contact with hedgehog antagonists of the present invention. Generally, a method is provided comprising the steps of isolating neural progenitor cells from an animal, perpetuating these cells in vitro or in vivo, preferably in the presence of growth factors, and regulating the differentiation of these cells into particular neural phenotypes, e.g., neurons and glia, by contacting the cells with a hedgehog antagonist.

Progenitor cells are thought to be under a tonic inhibitory influence that maintains the progenitors in a suppressed state until their differentiation is required. However, recent techniques have been provided which permit these cells to be proliferated, and unlike neurons that are terminally differentiated and therefore non-dividing, they can be produced in unlimited number and are highly suitable for transplantation into heterologous and autologous hosts with neurodegenerative diseases.

By "progenitor" it is meant an oligopotent or multipotent stem cell that is able to divide without limit and, under specific conditions, can produce daughter cells that terminally differentiate such as into neurons and glia. These cells can be used for transplantation into a heterologous or autologous host. By heterologous is meant a host other than the animal from which the progenitor cells were originally derived. By autologous is meant the identical host from which the cells were originally derived.

Cells can be obtained from embryonic, post-natal, juvenile or adult neural tissue from any animal. By any animal is meant any multicellular animal that contains nervous tissue. More, particularly, is meant any fish, reptile, bird, amphibian or mammal and the like. The most preferable donors are mammals, especially mice and humans.

In the case of a heterologous donor animal, the animal may be euthanized, and the brain and specific area of interest removed using a sterile procedure. Brain areas of particular interest include any area from which progenitor cells can be obtained which will serve to restore function to a degenerated area of the host's brain. These regions include areas of the central nervous system (CNS) including the cerebral cortex, cerebellum, midbrain, brainstem, spinal cord and ventricular tissue, and areas of the peripheral nervous system (PNS) including the carotid body and the adrenal medulla. More particularly, these areas include regions in the basal ganglia, preferably the striatum which consists of the caudate and putamen, or various cell groups such as the globus pallidus, the subthalamic nucleus, the nucleus basalis which is found to be degenerated in Alzheimer's Disease patients, or the substantia nigra pars compacta which is found to be degenerated in Parkinson's Disease patients.

Human heterologous neural progenitor cells may be derived from fetal tissue obtained from elective abortion, or from a post-natal, juvenile or adult organ donor. Autologous neural tissue can be obtained by biopsy, or from patients undergoing neurosurgery in which neural tissue is removed, in particular during epilepsy surgery, and more particularly during temporal lobectomies and hippocampalectomies.

Cells can be obtained from donor tissue by dissociation of individual cells from the connecting extracellular matrix of the tissue. Dissociation can be obtained using any known procedure, including treatment with enzymes such as trypsin, collagenase and the like, or by using physical methods of dissociation such as with a blunt instrument or by mincing with a scalpel to a allow outgrowth of specific cell types from a tissue. Dissociation of fetal cells can be carried out in tissue culture medium, while a preferable medium for dissociation of juvenile and adult cells is artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2+}$ aCSF contains the same ingredients except for $MgCl_2$ at a concentration of 3.2 mM and $CaCl_2$ at a concentration of 0.1 mM.

Dissociated cells can be placed into any known culture medium capable of supporting cell growth, including MEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. A particularly preferable medium for cells is a mixture of DMEM and F-12.

Conditions for culturing should be close to physiological conditions. The pH of the culture media should be close to physiological pH, preferably between pH 6-8, more preferably close to pH 7, even more particularly about pH 7.4. Cells should be cultured at a temperature close to physiological temperature, preferably between 30° C.-40° C., more preferably between 32° C.-38° C., and most preferably between 35° C.-37° C.

Cells can be grown in suspension or on a fixed substrate, but proliferation of the progenitors is preferably done in suspension to generate large numbers of cells by formation of "neurospheres" (see, for example, Reynolds et al. (1992) Science 255:1070-1709; and PCT Publications WO93/01275, WO94/09119, WO94/10292, and WO94/16718). In the case of propagating (or splitting) suspension cells, flasks are shaken well and the neurospheres allowed to settle on the bottom corner of the flask. The spheres are then transferred to a 50 ml centrifuge tube and centrifuged at low speed. The medium is aspirated, the cells resuspended in a small amount of medium with growth factor, and the cells mechanically dissociated and resuspended in separate aliquots of media.

Cell suspensions in culture medium are supplemented with any growths, factor which allows for the proliferation of progenitor cells and seeded in any receptacle capable of sustaining cells, though as set out above, preferably in culture flasks or roller bottles. Cells typically proliferate within 3-4 days in a 37° C. incubator, and proliferation can be reinitiated at any time after that by dissociation of the cells and resuspension in fresh medium containing growth factors.

In the absence of substrate, cells lift off the floor of the flask and continue to proliferate in suspension forming a hollow sphere of undifferentiated cells. After approximately 3-10 days in vitro, the proliferating clusters (neurospheres) are fed every 2-7 days, and more particularly every 2-4 days by gentle centrifugation and resuspension in medium containing growth factor.

After 6-7 days in vitro, individual cells in the neurospheres can be separated by physical dissociation of the neurospheres with a blunt instrument, more particularly by triturating the neurospheres with a pipette. Single cells from the dissociated neurospheres are suspended in culture medium containing growth factors, and differentiation of the cells can be control in culture by plating (or resuspending) the cells in the presence of a hedgehog antagonist.

To further illustrate other uses of the subject hedgehog antagonists, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123:265-289; and Freund et al. (1985) *J Neurosci* 5:603-616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The subject method can be used to regulate the growth state in the culture, or where fetal tissue is used, especially neuronal stem cells, can be used to regulate the rate of differentiation of the stem cells.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of hedgehog antagonists employed in the present method to culture such stem cells can be to regulate differentiation of the uncommitted progenitor, or to regulate further restriction of the developmental fate of a committed progenitor cell towards becoming a terminally differentiated neuronal cell. For example, the present method can be used in vitro to regulate the differentiation of neural crest cells into glial cells, schwann cells, chromaffin cells, cholinergic sympathetic or parasympathetic neurons, as well as peptidergic and serotonergic neurons. The hedgehog antagonists can be used alone, or can be used in combination with other neurotrophic factors that act to more particularly enhance a particular differentiation fate of the neuronal progenitor cell.

In addition to the implantation of cells cultured in the presence of the subject hedgehog antagonists, yet another aspect of the present invention concerns the therapeutic application of a hedgehog antagonist to regulate the growth state of neurons and other neuronal cells in both the central nervous system and the peripheral nervous system. The ability of ptc, hedgehog, and smoothened to regulate neuronal differentiation during development of the nervous system and also presumably in the adult state indicates that, in certain instances, the subject hedgehog antagonists can be expected to facilitate control of adult neurons with regard to maintenance, functional performance, and aging of normal cells; repair and regeneration processes in chemically or mechanically lesioned cells; and treatment of degeneration in certain pathological conditions. In light of this understanding, the present invention, specifically contemplates applications of the subject method to the treatment protocol of (prevention and/or reduction of the severity of) neurological conditions deriving from: (i) acute, subacute, or chronic injury to the nervous system, including traumatic injury, chemical injury, vascular injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amyotrophic lateral sclerosis and the like, as well as spinocerebellar degenerations; and (iv) chronic immunological diseases of the nervous system or affecting the nervous system, including multiple sclerosis.

As appropriate, the subject method can also be used in generating nerve prostheses for the repair of central and peripheral nerve damage. In particular, where a crushed or severed axon is intubulated by use of a prosthetic device, hedgehog antagonists can be added to the prosthetic device to regulate the rate of growth, and regeneration of the dendridic processes. Exemplary nerve guidance channels are described in U.S. Pat. Nos. 5,092,871 and 4,955,892.

In another embodiment, the subject method can be used in the treatment of neoplastic or hyperplastic transformations such as may occur in the central nervous system. For instance, the hedgehog antagonists can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas.

In a preferred embodiment, the subject method can be used as part of a treatment regimen for malignant medulloblastoma and other primary CNS malignant neuroectodermal tumors.

In certain embodiments, the subject method is used as part of treatment program for medulloblastoma. Medulloblastoma, a primary brain tumor, is the roost common brain tumor in children. A medulloblastoma is a primitive neuroectodermal tumor arising in the posterior fossa. They account for approximately 25% of all pediatric brain tumors (Miller). Histologically, they are small round cell tumors commonly arranged in true rosettes, but may display some differentiation to astrocytes, ependymal cells or neurons (Rorke; Kleihues). PNET's may arise in other areas of the brain including the pineal gland (pineoblastoma) and cerebrum. Those arising in the supratentorial region generally fare worse than their PF counterparts.

Medulloblastoma/PNET's are known to recur anywhere in the CNS after resection, and can even metastasize to bone. Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other embodiments, the subject method is used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. In the CHOP series of 51 children reported with ependymomas, ¾ were histologically benign. Approximately ⅔ arose from the region of the 4th ventricle. One third presented in the supratentorial region. Age at presentation peaks between birth and 4 years, as demonstrated by SEER data as well as data from CHOP. The median age is about 5 years. Because so many children with this disease are babies, they often require multimodal therapy.

Yet another aspect of the present invention concerns the observation in the art that ptc, hedgehog, and/or smoothened are involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising hedgehog antagonists can also be utilized for both cell culture and therapeutic methods involving generation and maintenance of non-neuronal tissue.

In one embodiment, the present invention makes use of the discovery that ptc, hedgehog, and smoothened are apparently involved in controlling the development of stem cells responsible for formation of the digestive tract, liver, lungs, and other organs which derive from the primitive gut. Shh serves as an inductive signal from the endoderm to the mesoderm, which is critical to gut morphogenesis. Therefore, for example, hedgehog antagonists of the instant method can be employed for regulating the development and maintenance of an artificial liver that can have multiple metabolic functions of a normal liver. In an exemplary embodiment, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of hedgehog antagonists can be utilized in conjunction with transplantation of such artificial livers, as well as embryonic liver structures, to regulate uptake of intraperitoneal implantation, vascularization, and in vivo differentiation and maintenance of the engrafted liver tissue.

In yet another embodiment, the subject method can be employed therapeutically to regulate such organs after physical, chemical or pathological insult. For instance, therapeutic compositions comprising hedgehog antagonists can be utilized in liver repair subsequent to a partial hepatectomy.

The generation of the pancreas and small intestine from the embryonic gut depends on intercellular signalling between the endodermal and mesodermal cells of the gut. In particular, the differentiation of intestinal mesoderm into smooth muscle has been suggested to depend on signals from adjacent endodermal cells. One candidate mediator of endodermally derived signals in the embryonic hindgut is Sonic hedgehog. See, for example, Apelqvist et al. (1997) *Curr Biol* 7:801-4. The Shh gene is expressed throughout the embryonic gut endoderm with the exception of the pancreatic bud endoderm, which instead expresses high levels of the homeodomain protein Ipf1/Pdx1 (insulin promoter factor 1/pancreatic and duodenal homeobox 1), an essential regulator of early pancreatic development. Apelqvist et ah, supra, have examined whether the differential expression of Shh in the embryonic gut tube controls the differentiation of the surrounding mesoderm into specialised mesoderm derivatives of the small intestine and pancreas. To test this, they used the promoter of the Ipf1/Pdx1 gene to selectively express Shh in the developing pancreatic epithelium. In Ipf1/Pdx1-Shh transgenic mice, the pancreatic mesoderm developed into smooth muscle and interstitial cells of Cajal, characteristic of the intestine, rather than into pancreatic mesenchyme and spleen. Also, pancreatic explants exposed to Shh underwent a similar program of intestinal differentiation. These results provide evidence that the differential expression of endodermally derived Shh controls the fate of adjacent mesoderm at different regions of the gut tube.

In the context of the present invention, it is contemplated therefore that the subject hedgehog antagonists can be used to control or regulate the proliferation and/or differentiation of pancreatic tissue both in vivo and in vitro.

There are a wide variety of pathological cell proliferative and differentiative conditions for which the inhibitors of the present invention may provide therapeutic benefits, with the general strategy being, for example, the correction of aberrant insulin expression, or modulation of differentiation. More generally, however, the present invention relates to a method of inducing and/or maintaining a differentiated state, enhancing survival and/or affecting proliferation of pancreatic cells, by contacting the cells with the subject inhibitors. For instance, it is contemplated by the invention that, in light of the apparent involvement of ptc, hedgehog, and smoothened in the formation of ordered spatial arrangements of pancreatic tissues, the subject method could be used as part of a technique to generate and/or maintain such tissue both in vitro and in vivo. For instance, modulation of the function of hedgehog can be employed in both cell culture and therapeutic methods involving generation and maintenance β-cells and possibly also for non-pancreatic tissue, such as in controlling the development and maintenance of tissue from the digestive tract, spleen, lungs, urogenital organs (e.g., bladder), and other organs which derive from the primitive gut.

In an exemplary embodiment, tire present method can be used in the treatment of hyperplastic and neoplastic disorders effecting pancreatic tissue, particularly those characterized by aberrant proliferation of pancreatic cells. For instance, pancreatic cancers are marked by abnormal proliferation of pancreatic cells that can result in alterations of insulin secretory capacity of the pancreas. For instance, certain pancreatic hyperplasias, such as pancreatic carcinomas, can result in hypoinsulinemia due to dysfunction of β-cells or decreased islet cell mass. To the extent that aberrant ptc, hedgehog, and smoothened signaling may be indicated in disease progression, the subject inhibitors, can be used to enhance regeneration of the tissue after anti-tumor therapy.

Moreover, manipulation of hedgehog signaling properties at different points may be useful as part of a strategy for reshaping/repairing pancreatic tissue both in vivo and in vitro. In one embodiment, the present invention makes use of the apparent involvement of ptc, hedgehog, and smoothened in regulating the development of pancreatic tissue. In general, the subject method can be employed therapeutically to regulate the pancreas after physical, chemical or pathological insult. In yet another embodiment, the subject method can be applied to cell culture techniques, and in particular, may be employed to enhance the initial generation of prosthetic pancreatic tissue devices. Manipulation of proliferation and differentiation of pancreatic tissue, for example, by altering hedgehog activity, can provide a means for more carefully controlling the characteristics of a cultured tissue. In an exemplary embodiment, the subject method can be used to augment production of prosthetic devices which require β-islet cells, such as may be used in the encapsulation devices described in, for example, the Aebischer et al. U.S. Pat. No. 4,892,538, the Aebischer et al. U.S. Pat. No. 5,106,627, the Lim U.S. Pat. No. 4,391,909, and the Sefton U.S. Pat. No. 4,353,888. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearence of embryonal traits in mature β-cells can be observed. By utilizing the subject hedgehog antagonists, the differentiation path or proliferative index of the cells can be regulated.

Furthermore, manipulation of the differentiative state of pancreatic tissue can be utilized in conjunction with transplantation of artificial pancreas so as to promote implantation, vascularization, and in vivo differentiation and maintenance of the engrafted tissue. For instance, manipulation of hedgehog function to affect tissue differentiation can be utilized as a means of maintaining graft viability.

Bellusci et al. (1997) *Development* 124:53 report that Sonic hedgehog regulates lung mesenchymal cell proliferation in vivo. Accordingly, the present method can be used to regulate regeneration of lung tissue, e.g., in the treatment of emphysema and respiratory distress syndrome.

Fujita et al. (1997) *Biochem Biophys Res Commun* 238:658 reported that Sonic hedgehog is expressed in human lung squamous carcinoma, and adenocarcinoma cells. The expression of Sonic hedgehog was also detected in the human lung squamous carcinoma tissues, but not in the normal lung tissue of the same patient. They also observed that Sonic hedgehog stimulates the incorporation of BrdU into the carcinoma cells and stimulates their cell growth, while anti-Shh-N inhibited their cell growth. These results suggest that a ptc, hedgehog, and/or smoothened is involved in the cell growth of such transformed lung tissue and therefore indicates that the subject method can be used as part of a treatment of lung carcinoma and adenocarcinomas, and other proliferative disorders involving the lung epithelia.

Many other tumors may, based on evidence such as involvement of the hedgehog pathway in these tumors, or detected expression of hedgehog or its receptor in these tissues during development, be affected by treatment with the subject compounds. Such tumors include, but are by no means limited to, tumors related to Gorlin's syndrome (e.g., basal cell carcinoma, medulloblastoma, meningioma, etc.), tumors evidenced in pet knock-out mice (e.g., hemangioma, rhabdomyosarcoma, etc.), tumors resulting from gli-1 amplification (e.g., glioblastoma, sarcoma, etc.), tumors connected with TRC8, a ptc homolog (e.g., renal carcinoma, thyroid carcinoma, etc.), Ext-1-related tumors (e.g., bone cancer, etc.), Shh-induced tumors (e.g., lung cancer, chondrosarcomas, etc.), and other tumors (e.g., breast cancer, urogenital cancer (e.g., kidney, bladder, ureter, prostate, etc.), adrenal cancer, gastrointestinal cancer (e.g., stomach, intestine, etc.), etc.).

In still another embodiment of the present invention, compositions comprising hedgehog antagonists can be used in the in vitro generation of skeletal tissue, such as from skeletogenic stem cells, as well as the in vivo treatment of skeletal tissue deficiencies. The present invention particularly contemplates the use of hedgehog antagonists to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

For instance, the method of the present invention can be used as part of a regimen for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a laxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a hedgehog antagonist particularly an antagonist selective for Indian hedgehog signal transduction, to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In an illustrative embodiment, the subject method can be used as part of a therapeutic intervention in the treatment of cartilage of a diarthroidal joint, such as a knee, an ankle, an elbow, a hip, a wrist, a knuckle of either a finger or toe, or a tempomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. The subject antagonists may be administered as an injection into the joint with, for instance, an arthroscopic needle. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. However, problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair; anterior cruciate ligaments, the tissue undergoes a metaplasia to pure fibrous tissue. By regulating the rate of chondrogenesis, the subject method can be used to particularly address this problem, by helping to adaptively control the implanted cells in the new environment and effectively resemble hypertrophic chondrocytes of an earlier developmental stage of the tissue.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res* 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers that degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a hedgehog antagonist during certain stages of the culturing process in order to manage the rate of differentiation of chondrocytes and the formation of hypertrophic chrondrocytes in the culture.

In another embodiment, the implanted device is treated with a hedgehog antagonist in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis.

In still further embodiments, the subject method can be employed as part of a regimen for the generation of bone (osteogenesis) at a site in the animal where such skeletal tissue is deficient. Indian hedgehog is particularly associated with the hypertrophic chondrocytes that are ultimately replaced by osteoblasts. For instance, administration of a hedgehog antagonist of the present invention can be employed as part of a method for regulating the rate of bone loss in a subject. For example, preparations comprising hedgehog antagonists can be employed, for example, to control endochondral ossification in the formation of a "model" for ossification.

In yet another embodiment of the present invention, a hedgehog antagonist can be used to regulate spermatogenesis. The hedgehog proteins, particularly Dhh, have been shown to be involved in the differentiation and/or proliferation and maintenance of testicular germ cells. Dhh expression is initiated in Sertoli cell precursors shortly after the activation of Sry (testicular determining gene) and persists in the testis into the adult. Males are viable but infertile, owing to a complete absence of mature sperm. Examination of the developing testis in different genetic backgrounds suggests that Dhh regulates both early and late stages of spermatogenesis, Bitgood et al. (1996) *Curr Biol* 6:298. In a preferred embodiment, the hedgehog antagonist can be used as a contraceptive. In similar fashion, hedgehog antagonists of the subject method are potentially useful for modulating normal ovarian function.

The subject method also has wide applicability to the treatment or prophylaxis of disorders afflicting epithelial tissue, as well as in cosmetic uses. In general, the method can be characterized as including a step of administering to an animal an amount of a hedgehog antagonist effective to alter the growth state of a treated epithelial tissue. The mode of administration and dosage regimens will vary depending on the epithelial tissue(s) to be treated. For example, topical formulations will be preferred where the treated tissue is epidermal tissue, such as dermal or mucosal tissues.

A method that "promotes the healing of a wound" results in the wound healing more quickly as a result of the treatment than a similar wound heals in the absence of the treatment. "Promotion of wound healing" can also mean that the method regulates the proliferation and/or growth of, inter alia, keratinocytes, or that the wound heals with less scarring, less wound contraction, less collagen deposition and more superficial surface area. In certain instances, "promotion of wound healing" can also mean that certain methods of wound healing have improved success rates, (e.g., the take rates of skin grafts,) when used together with the method of the present invention.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the subject method, the rate of proliferation of epithelial cells in and proximal to the wound can be controlled in order to accelerate closure of the wound and/or minimize the formation of scar tissue.

The present treatment can also be effective as part of a therapeutic regimen for treating oral and paraoral ulcers, e.g. resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, dispose the body to potential secondary infection. Routine ingestion of food and water becomes a very painful event and, if the ulcers proliferate throughout the alimentary canal, diarrhea usually is evident with all its complicating factors. According to the present invention, a treatment for such ulcers which includes application of a hedgehog antagonist can reduce the abnormal proliferation and differentiation of the affected epithelium, helping to reduce the severity of subsequent inflammatory events.

The subject method and compositions can also be used to treat wounds resulting from dermatological diseases, such as lesions resulting from autoimmune disorders such as psoriasis. Atopic dermitits refers to skin trauma resulting from allergies associated with an immune response caused by allergens such as pollens, foods, dander, insect venoms and plant toxins.

In other embodiments, antiproliferative preparations of hedgehog antagonists can be used to inhibit lens epithelial cell proliferation to prevent post-operative complications of extracapsular cataract extraction. Cataract is an intractable eye disease and various studies on a treatment of cataract have been made. But at present, the treatment of cataract is attained by surgical operations. Cataract surgery has been applied for a long time and various operative methods have been examined. Extracapsular lens extraction has become the method of choice for removing cataracts. The major medical advantages of this technique over intracapsular extraction are lower incidence of aphakic cystoid macular edema and retinal detachment. Extracapsular extraction is also required for implantation of posterior chamber type intraocular lenses that are now considered to be the lenses of choice in most cases.

However, a disadvantage of extracapsular cataract extraction is the high incidence of posterior lens capsule opacification, often called after-cataract, which can occur in up to 50% of cases within three years after surgery. After-cataract is caused by proliferation of equatorial and anterior capsule lens epithelial cells that remain after extracapsular lens extraction. These cells proliferate to cause Sommerling rings, and along with fibroblasts that also deposit and occur on the posterior capsule, cause opacification of the posterior capsule, which interferes with vision. Prevention of after-cataract would be preferable to treatment. To inhibit secondary cataract formation, the subject method provides a means for inhibiting proliferation of the remaining lens epithelial cells. For example, such cells can be induced to remain quiescent by instilling a solution containing an hedgehog antagonist preparation into the anterior chamber of the eye after lens removal. Furthermore, the solution can be osmotically balanced to provide minimal effective dosage when instilled into the anterior chamber of the eye, thereby inhibiting subcapsular epithelial growth with some specificity.

The subject method can also be used in the treatment of corneopathies marked by corneal epithelial cell proliferation, as for example in ocular epithelial disorders such as epithelial downgrowth or squamous cell carcinomas of the ocular surface.

Levine et al. (1997) *J Neurosci* 17:6277 show that hedgehog proteins can regulate mitogenesis and photoreceptor differentiation in the vertebrate retina, and Ihh is a candidate factor from the pigmented epithelium to promote retinal progenitor proliferation and photoreceptor differentiation. Likewise, Jensen et al. (1997) *Development* 124:363 demonstrated that treatment of cultures of perinatal mouse retinal cells with the amino-terminal fragment of Sonic hedgehog protein results in an increase in the proportion of cells that incorporate bromodeoxuridine, in total cell numbers, and in rod photoreceptors, amacrine cells and Muller glial cells, suggesting that Sonic hedgehog promotes the proliferation of retinal precursor cells. Thus, the subject method can be used in the treatment of proliferative diseases of retinal cells and regulate photoreceptor differentiation.

Yet another aspect of the present invention relates to the use of the subject method to control hair growth. Hair is basically composed of keratin, a tough and insoluble protein; its chief strength lies in its disulphide bond of cystine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells.

In certain embodiments, the subject method can be employed as a way of reducing the growth of human hair as opposed to its conventional removal by cutting, shaving, or depilation. For instance, the present method can be used in the treatment of trichosis characterized by abnormally rapid or dense growth of hair, e.g. hypertrichosis. In an exemplary embodiment, hedgehog antagonists can be used to manage hirsutism, a disorder marked by abnormal hairiness. The subject method can also provide a process for extending the duration of depilation.

Moreover, because a hedgehog antagonist will often be cytostatic to epithelial cells, rather than cytotoxic, such agents can be used to protect hair follicle cells from cytotoxic agents that require progression into S-phase of the cell-cycle for efficacy, e.g. radiation-induced death. Treatment by the subject method can provide protection by causing the hair follicle cells to become quiescent, e.g., by inhibiting the cells from entering S phase, and thereby preventing the follicle cells from undergoing mitotic catastrophe or programmed cell death. For instance, hedgehog antagonists can be used for patients undergoing chemo- or radiation-therapies that ordinarily result in hair loss. By inhibiting cell-cycle progression during such therapies, the subject treatment can protect hair follicle cells from death that might otherwise result from activation of cell death programs. After the therapy has concluded, the instant method can also be removed with concomitant relief of the inhibition of follicle cell proliferation.

The subject method can also be used in the treatment of folliculitis, such as folliculitis decalvans, folliculitis ulerythematosa reticulata or keloid folliculitis. For example, a cosmetic prepration of an hedgehog antagonist can be applied topically in the treatment of pseudofolliculitis, a chronic disorder occurring most often in the submandibular region of the neck and associated with, shaving, the characteristic lesions of which are erythematous papules and pustules containing buried hairs.

In another aspect of the invention, the subject method can be used to induce differentiation and/or inhibit proliferation of epithelially derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical preparations of the invention are intended for the treatment of hyperplastic epidermal conditions, such as keratosis, as well as for the treatment of neoplastic epidermal conditions such as those characterized by a high proliferation rate for various skin cancers, as for example basal cell carcinoma or squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflammatory or non-inflammatory components. To illustrate, therapeutic preparations of a hedgehog antagonist, e.g., which promotes quiescense or differentiation can be used to treat varying forms of psoriasis, be they cutaneous, mucosal or ungual. Psoriasis, as described above, is typically characterized by epidermal keratinocytes that display marked proliferative activation and differentiation along a "regenerative" pathway. Treatment with an antiproliferative embodiment of the subject method can be used to reverse the pathological epidermal activiation and can provide a basis for sustained remission of the disease.

A variety of other keratotic lesions are also candidates for treatment with the subject method. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a hedgehog antagonist composition in amounts sufficient to inhibit hyperproliferation of epidermal/epidermoid cells of the lesion.

Acne represents yet another dermatologic ailment which may be treated by the subject method. Acne vulgaris, for instance, is a multifactorial disease most commonly occurring in teenagers and young adults, and is characterized by the appearance of inflammatory and noninflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by *Propinobacterium acnes* and *Staphylococcus epidermidis* bacteria and *Pitrosporum ovale*, a yeast. Treatment with an antiproliferative hedgehog antagonist, particularly topical preparations, may be useful for preventing the transitional features of the ducts, e.g. hypercornification, which lead to lesion formation. The subject treatment may further include, for example, antibiotics, retinoids and antiandrogens.

The present invention also provides a method for treating various forms of dermatitis. Dermatitis is a descriptive term referring to poorly demarcated lesions that are either pruritic, erythematous, scaley, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow crusted patches on various areas, especially the scalp, with exfoliation of an excessive amount of dry scales. The subject method can also be used in the treatment of stasis dermatitis, an often chronic, usually eczematous dermatitis. Actinic dermatitis is dermatitis that due to exposure to actinic radiation such as that from the sun, ultraviolet waves or x- or gamma-radiation. According to the present invention, the subject method can be used in the treatment and/or prevention of certain symptoms of dermatitis caused by unwanted proliferation of epithelial cells.

Such therapies for these various forms of dermatitis can also include topical and systemic corticosteroids, antipuritics, and antibiotics.

For example, it is contemplated that the subject method could be used to inhibit angiogenesis. Hedgehog is known to stimulate angiogenesis. Matrigel plugs impregnated with hedgehog protein and inserted into mice evince substantial neovascularization, whereas Matrigel plugs not carrying hedgehog show comparatively little vascularization. Hedgehog protein is also capable of increasing vascularization of the normally avascular mouse cornea. The ptc-1 gene is expressed in normal vascular tissues, including the endothelial cells of the aorta, vascular smooth muscle cells, adventitial fibroblasts of the aorta, the coronary vasculature and cardiomyocytes of the atria and ventricles. These tissues are also sensitive to hedgehog protein. Treatment with exogenous hedgehog causes upregulation of ptc-1 expression. In addition, hedgehog proteins stimulate proliferation of vascular smooth muscle cells in vivo. Hedgehog proteins also cause fibroblasts to increase expression of angiogenic growth factors such as VBGF, bFGF, Ang-1 and Ang-2. Lastly, hedgehog proteins are known to stimulate recovery from ischemic injury and stimulate formation of collateral vessels.

Given that hedgehog promotes angiogenesis, hedgehog antagonists are expected to act as angiogenesis inhibitors, particularly in situations where some level of hedgehog signaling is necessary for angiogenesis.

Angiogenesis is fundamental to many disorders. Persistent, unregulated angiogenesis occurs in a range of disease states, tumor metastases and abnormal growths by endothelial cells. The vasculature created as a result of angiogenic processes supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

Diseases caused by, supported by or associated with angiogenesis include ocular neovascular disease, age-related macular degeneration, diabetic retinopathy, retinopathy of prematurity, corneal graft rejection, neovascular glaucoma, retrolental fibroplasia, epidemic keratoconjunctivitis, Vitamin A deficiency, contact lens overwear, atopic keratitis, superior limbic keratitis, pterygium keratitis sicca, Sjogren's, acne rosacea, phylectenulosis, syphilis, *Mycobacteria* infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegeners sarcoidosis, Scleritis, Stevens Johnson disease, periphigoid radial keratotomy, corneal graph rejection, rheumatoid arthritis, osteoarthritis chronic inflammation (eg., ulcerative colitis or Crohn's disease), hemangioma, Osier-Weber-Rendu disease, and hereditary hemorrhagic telangiectasia.

In addition, angiogenesis plays a critical role in cancer. A tumor cannot expand without a blood supply to provide nutrients and remove cellular wastes. Tumors in which angiogenesis is important include solid tumors such as rhabdomyosarcomas, retinoblastoma, Ewing sarcoma, neuroblastoma, and osteosarcoma, and benign tumors such as acoustic neuroma, neurofibroma, trachoma and pyogenic granulomas. Angiogenic factors have been found associated with several solid tumors. Prevention of angiogenesis could halt the growth of these tumors and the resultant damage to the animal due to the presence of the tumor. Angiogenesis is also associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

In addition to tumor growth, angiogenesis is important in metastasis. Initially, angiogenesis is important is in the vascularization of the tumor which allows cancerous cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

It is anticipated that the invention will be useful for the treatment and/or prevention of respiratory distress syndrome or other disorders resulting from inappropriate lung surface tension. Respiratory distress syndrome results from insufficient surfactant in the alveolae of the lungs. The lungs of vertebrates contain surfactant, a complex mixture of lipids and protein that causes surface tension to rise during lung inflation and decrease during lung deflation. During lung deflation, surfactant decreases such that there are no surface forces that would otherwise promote alveolar collapse. Aerated alveoli that have not collapsed during expiration permit continuous oxygen and carbon dioxide transport between blood and alveolar gas and require much less force to inflate during the subsequent inspiration. During inflation, lung surfactant increases surface tension as the alveolar surface area increases. A rising surface tension in expanding alveoli opposes over-inflation in those airspaces and tends to divert inspired air to less well-aerated alveoli, thereby facilitating even lung aeration.

Respiratory distress syndrome is particularly prevalent among premature infants. Lung surfactant is normally synthesized at a very low rate until the last six weeks of fetal life. Human infants born more than six weeks before the normal term of a pregnancy have a high risk of being born with inadequate amounts of lung surfactant and inadequate rates of surfactant synthesis. The more prematurely an infant is born, the more severe the surfactant deficiency is likely to be. Severe surfactant deficiency can lead to respiratory failure within a few minutes or hours of birth. The surfactant deficiency produces progressive collapse of alveoli (atelectasis) because of the decreasing ability of the lung to expand despite maximum inspiratory effort. As a result, inadequate amounts of oxygen reach the infant's blood. RDS can occur in adults as well, typically as a consequence of failure in surfactant biosynthesis.

Lung tissue of premature infants shows high activity of the hedgehog signaling pathway. Inhibition of this pathway using hedgehog antagonists increases the formation of lamellar bodies and increases the expression of genes involved in surfactant biosynthesis. Lamellar bodies are subcellular structures associated with surfactant biosynthesis. For these reasons, treatment of premature infants with a hedgehog antagonist should stimulate surfactant biosynthesis and ameliorate RDS. In cases where adult RDS is associated with hedgehog pathway activation, treatment with hedgehog antagonists should also be effective.

It is further contemplated that the use of hedgehog antagonists may be specifically targeted to disorders where the affected tissue and/or cells evince high hedgehog pathway activation. Expression of gli genes is activated by the hedgehog signaling pathway, including gli-1, gli-2 and gli-3, gli-1 expression is most consistently correlated with hedgehog signaling activity across a wide range of tissues and disorders, while gli-3 is somewhat less so. The gli genes encode transcription factors that activate expression of many genes needed to elicit the full effects of hedgehog signaling. However, the Gli-3 transcription factor can also act as a repressor of hedgehog effector genes, and therefore, expression of gli-3 can cause a decreased effect of the hedgehog signaling pathway. Whether Gli-3 acts as a transcriptional activator or repressor depends on post-translational events, and therefore it is expected that methods for detecting the activating form (versus the repressing form) of Gli-3 protein would also be a reliable measure of hedgehog pathway activation. gli-2 gene expression is expected to provide a reliable marker for hedgehog pathway activation. The gli-1 gene is strongly expressed in a wide array of cancers, hyperplasias and immature lungs, and serves as a marker for the relative activation of the hedgehog pathway. In addition, tissues, such as immature lung, that have high gli gene expression are strongly affected by hedgehog inhibitors. Accordingly, it is contemplated that the detection of gli gene expression may be used as a powerful predictive tool to identify tissues and disorders that will particularly benefit from treatment with a hedgehog antagonist.

In preferred embodiments, gli-1 expression levels are detected, either by direct detection of the transcript or by detection of protein levels or activity. Transcripts may be detected using any of a wide range of techniques that depend primarily on hybridization of probes to the gli-1 transcripts or to cDNAs synthesized therefrom. Well known techniques include Northern blotting, reverse-transcriptase PCR and microarray analysis of transcript levels. Methods for detecting Gli protein levels include Western blotting, immunoprecipitation, two-dimensional polyacrylamide gel electrophoresis (2D SDS-PAGE) (preferably compared against a standard wherein the position of the Gli proteins has been determined), and mass spectroscopy. Mass spectroscopy may be coupled with a series of purification steps to allow high-throughput identification of many different protein levels in a particular sample. Mass spectroscopy and 2D SDS-PAGE can also be used to identify post-transcriptional modifications to proteins including proteolytic events, ubiquitination, phosphorylation, lipid modification etc. Gli activity may also be assessed by analyzing binding to substrate DNA or in vitro transcriptional activation of target promoters. Gel shift assays, DNA footprinting assays and DNA-protein crosslinking assays are all methods that may be used to assess the presence of a protein capable of binding to Gli binding sites on DNA.

In preferred embodiments, gli transcript levels are measured and diseased or disordered tissues showing abnormally high gli levels are treated with a hedgehog antagonist. Premature lung tissue, lung cancers (e.g., adenocarcinomas, broncho-alveolar adenocarcinomas, small cell carcinomas), breast cancers (e.g., inferior ductal carcinomas, inferior lobular carcinomas, tubular carcinomas), prostate cancers (e.g., adenocarcinomas), and benign prostatic hyperplasias all show strongly elevated gli-1 expression levels in certain cases. Accordingly, gli-1 expression levels are a powerful diagnostic device to determine which of these tissues should be treated with a hedgehog antagonist. In addition, there is substantial correlative evidence that cancers of urothelial cells (e.g., bladder cancer, other urogenital cancers) will also have elevated gli-1 levels in certain cases. For example, it is known that loss of heterozygosity on chromosome 9q22 is common in bladder cancers. The ptc-1 gene is located at this position and ptc-1 loss of function is probably a partial cause of hyperproliferation, as in many other cancer types. Accordingly, such cancers would also show high gli expression and would be particularly amenable to treatment with a hedgehog antagonist.

Expression of ptc-1 and ptc-2 is also activated by the hedgehog signaling pathway, but these genes are inferior to the gli genes as markers of hedgehog pathway activation. In certain tissues only one of ptc-1 or ptc-2 is expressed although the hedgehog pathway is highly active. For example, in testicular development, Indian hedgehog plays an important role and the hedgehog pathway is activated, but only ptc-2 is expressed. Accordingly, these genes are individually unreliable as markers for hedgehog pathway activation, although simultaneous measurement of both genes are contemplated as a useful indicator for tissues to be treated with a hedgehog antagonist.

Ailments which may be treated by the subject method are disorders specific to non-humans, such as mange.

In still another embodiment, the subject method can be used in the treatment of human cancers, particularly basal cell carcinomas and other tumors of epithelial tissues such as the skin. For example, hedgehog antagonists can be employed, in the subject method, as part of a treatment for basal cell nevus syndrome (BCNS), and other human carcinomas, adenocarcinomas, sarcomas and the like.

Compounds of the invention may be administered prior to, concomitantly with, or following administration of other anticancer treatments such as radiation therapy or chemotherapy. Suitable cytostatic chemotherapy compounds include, but are not limited to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphtheria toxin; (Vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporine, STI571 (CPG 57148B) or UCN-01 (7-hydroxystaurosporine); (x) miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists. In a particular embodiment, compounds of the present invention are coadministered, with a cytostatic compound selected from cisplatin, doxorubicin, taxol, taxotere and mitomycin C.

Another class of active compounds which can be used in the present invention are those which are able to sensitize for or induce apoptosis by binding to death receptors ("death receptor agonists"). Such agonists of death receptors include death receptor ligands such as tumor necrosis factor α (TNF-α), tumor necrosis factor β (TNF-β, lymphotoxin-α), LT-β (lymphotoxin-β), TRAIL (Apo2L, DR4 ligand), CD95 (Fas, APO-1) ligand, TRAMP (DR3, Apo-3) ligand, DR6 ligand as well as fragments and derivatives of any of said ligands. In a particular embodiment, the death receptor ligand is TNF-α. In another particular embodiment the death receptor ligand is Apo2L/TRAIL. Furthermore, death receptors agonists comprise agonistic antibodies to death receptors such as anti-CD95 antibody, anti-TRAIL-R1 (DR4) antibody, anti-TRAIL-R2 (DR5) antibody, anti-TRAIL-R3 antibody, anti-TRAIL-R4 antibody, anti-DR6 antibody, anti-TNF-R1 antibody and anti-TRAMP (DR3) antibody as well as fragments and derivatives of any of said antibodies.

For the purpose of sensitizing cells for apoptosis, the compounds of the present invention can also be used in combination with radiation therapy. The phrase "radiation therapy" refers to the use of electromagnetic or particulate radiation in the treatment of neoplasia. Radiation therapy is based on the principle that high-dose radiation delivered to a target area will result in the death of reproducing cells in both tumor and normal tissues. The radiation dosage regimen is generally defined in terms of radiation absorbed dose (rad), time and fractionation, and must be carefully defined by the oncologist. The amount of radiation a patient receives will depend on various consideration including the location of the tumor in relation to other organs of the body, and the extent to which the tumor has spread. Examples of radiotherapeutic agents are provided in, but not limited to, radiation therapy and is known in the art (Hellman, Principles of Radiation Therapy, Cancer, in Principles I and Practice of Oncology, 24875 (Devita et al., 4th ed., vol 1, 1993). Recent advances in radiation therapy include three-dimensional conformal external beam radiation, intensity modulated radiation therapy (IMRT), stereotactic radiosurgery and brachytherapy (interstitial radiation therapy), the latter placing the source of radiation directly into the tumor as implanted "seeds". These newer treatment modalities deliver greater doses of radiation to the tumor, which accounts for their increased effectiveness when compared to standard external beam radiation therapy.

Ionizing radiation with beta-emitting radionuclides is considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme; they deliver very high LET dosage, but have an extremely limited range and must, therefore, be in intimate contact with the cells of the tissue to be treated. In addition, alpha emitters are generally heavy metals, which limits the possible chemistry and presents hazards from leakage of radionuclide from the area to be treated. Depending on the tumor to be treated, all kinds of emitters are conceivable within the scope of the present invention. Furthermore, the present invention encompasses types of non-ionizing radiation, such as ultraviolet (UV) radiation, high energy visible light, microwave radiation (hyperthermia therapy), infrared (IR) radiation and lasers. In a particular embodiment of the present invention, UV radiation is applied.

In a preferred embodiment, the subject method is used as part of a treatment of prophylaxis regimen for treating (or preventing) basal cell carcinoma. The deregulation of the hedgehog signaling pathway may be a general feature of basal cell carcinomas caused by ptc mutations. Consistent overexpression of human ptc mRNA has been described in tumors of familial and sporadic BCCs, determined by in situ hybridization. Mutations that inactivate ptc may be expected to result in overexpression of mutant Ptc, because ptc displays negative autoregulation. Prior research demonstrates that overexpression of hedgehog proteins can also lead to tumorigenesis.

That sonic hedgehog (Shh) has a role in tumorigenesis in the mouse has been suggested by research in which transgenic mice overexpressing Shh in the skin developed features of BCNS, including multiple BCC-like epidermal proliferations over the entire skin surface, after only a few days of skin development. A mutation in the Shh human gene from a BCC was also described; it was suggested that Shh or other Hh genes in humans could act as dominant oncogenes in humans. Sporadic ptc mutations have also been observed in BCCs from otherwise normal individuals, some of which are UV-signature mutations. In one recent study of sporadic BCCs, five UV-signature type mutations, either CT or CCTT changes, were found out of fifteen tumors determined to contain ptc mutations. Another recent analysis of sporadic ptc mutations in BCCs and neuroectodermal tumors revealed one CT change in one of three ptc mutations found in the BCCs. See, for example, Goodrich et al. (1997) *Science* 277:1109-13; Xie et al. (1997) *Cancer Res* 57:2369-72; Oro et al. (1997) *Science* 276:817-21; Xie et al. (1997) *Genes Chromosomes Cancer* 18:305-9; Stone et al. (1996) *Nature* 384:129-34; and Johnson et al. (1996) *Science* 272:1668-71.

The subject method can also be used to treatment patients with BCNS, e.g., to prevent BCC or other effects of the disease which may be the result of ptc loss-of-function, hedgehog gain-of-function, or smoothened gain-of-function. Basal cell nevus syndrome is a rare autosomal dominant disorder characterized by multiple BCCs that appear at a young age. BCNS patients are very susceptible to the development of these tumors; in the second decade of life, large numbers appear, mainly on sun-exposed areas of the skin. This disease also causes a number of developmental abnormalities, including rib, head and face alterations, and sometimes polydactyly, syndactyly, and spina bifida. They also develop a number of tumor types in addition to BCCs: fibromas of the ovaries and heart, cysts off the skin and jaws, and in the central nervous system, medulloblastomas and meningiomas. The subject method can be used to prevent or treat such tumor types in BCNS and non-BCNS patients. Studies of BCNS patients show that they have both genomic and sporadic mutations in the ptc gene, suggesting that these mutations are the ultimate cause of this disease.

In another aspect, the present invention provides pharmaceutical preparations comprising hedgehog antagonists. The hedgehog antagonists for use in the subject method may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as array conventional media or agent is incompatible with the activity of the hedgehog antagonist, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Pharmaceutical formulations of the present invention can also include veterinary compositions, e.g., pharmaceutical preparations of the hedgehog antagonists suitable for veterinary uses, e.g., for the treatment of livestock or domestic animals, e.g., dogs.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a hedgehog antagonist at a particular target site.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to decrease hedgehog pathway signaling or else is the minimum amount necessary to cause reduction in size, volume or mass of a tumor that is responsive to hedgehog signaling, or a reduction in the increase in size, volume or mass of such a tumor relative to the increase in the absence of administering the compound of the invention. Alternatively "effective amount" of the compound means the amount necessary to reduce the number of malignant cells or the rate in increase of the number of malignant cells. Alternatively, "effective amount" is the amount of the compound of the invention required to increase survival of patients afflicted with an anti-hedgehog pathway sensitive tumor. Such amount may be below the amount that is toxic to normal cells, or the mammal as a whole. With respect to non-malignant indications, "effective amount" means the amount of compound of the invention required to decrease severity of the particular indication or symptoms thereof.

Generally, the initial pharmaceutically effective amount of the compound of the invention administered parenterally per dose will be in the range of about 0.01 to about 100 mg/kg, for example about 0.1 to about 20 mg/kg of patient body weight per day, for example about 0.3 to about 15 mg/kg/day. Oral unit dosage forms, such as tablets and capsules, may contain from about 25 to about 1000 mg of the compound of the invention.

The preparations of the invention may be given by any suitable means, including oral, topical, transdermal, parenteral, subcutaneous, rectal, intraperitoneal, intrapulmonary, and intranasal, and, if desired for local treatment, intralesional administration. They are of course given by forms suitable for each administration route. For example, they are administered in tablets or capsule form, by injection, inhalation, eye lotion, ointment, suppository, controlled release patch, etc. administration by injection, infusion or inhalation; topical by lotion or ointment; and rectal by suppositories. Oral and topical administrations are preferred. Parenteral infusions include intramuscular, intravenous, intraarterial, intraperitoneal, or subcutaneous administration. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example, 5-400 mg, of the invention in a suitable buffer solution, e.g., a phosphate buffer, adding a tonicifier, e.g., a salt such as sodium chloride, if desired. The solution is typically filtered, e.g., using a 0.2 micron filter, to remove impurities and contaminants. Topical formulations include ointments, creams, lotions, powders, solutions, pessaries, sprays, aerosols and capsules. Ointments and creams may be formulated with an aqueous or oily base with the addition of suitable thickening and/or gelling agents and/or solvents. Such bases may include water and/or an oil such a liquid paraffin or a vegetable oil such as arachis oil or castor oil or a solvent such as a polyethylene glycol. Thickening agents which may be used include soft paraffin, aluminum stearate, cetostearyl alcohol, polyethylene glycols, microcrystalline wax and beeswax. Lotions may be formulated with an aqueous or oily base and may contain one or more emulsifying agents, stabilizing agents, dispersing agents, suspending agents or thickening agents. Powders for external application may be formed with the aid of any suitable powder base, e.g., talc, lactose or starch. Drops may be formulated with an aqueous or non-aqueous base also comprising one or more dispersing agents, solubilizing agents or suspending agents.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, Intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically/, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular hedgehog antagonist employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable and/or sterile carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

V. Pharmaceutical Compositions

While it is possible for a compound of the present invention to be administered alone, it is preferable to administer the compound as a pharmaceutical formulation (composition). The hedgehog antagonists according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect by overcoming a ptc loss-of-function, hedgehog gain-of-function, or smoothened gain-of-function in at least a subpopulation of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present hedgehog antagonists may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Set* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

It is known that sterols, such as cholesterol, will form complexes with cyclodextrins. Thus, in preferred embodiments, where the inhibitor is a steroidal alkaloid, it may be formulated with cyclodextrins, such as $\alpha$-, $\beta$- and $\gamma$-cyclodextrin, dimethyl-$\beta$ cyclodextrin and 2-hydroxypropyl-$\beta$-cyclodextrin.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active hedgehog antagonist.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the hedgehog antagonists in the proper medium. Absorption enhancers can also be used to increase the flux of the hedgehog antagonists across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

VI. Synthetic Preparation and Identification of Active Antagonists

The subjects steroidal alkaloids, and congeners thereof, can be prepared readily by employing the cross-coupling technologies of Suzuki, Stille, and the like. These coupling reactions are carried out under relatively mild conditions and tolerate a wide range of "spectator" functionality.

a. Combinatorial Libraries

The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g. a variegated library of compounds represented above, can be screened rapidly in high throughput assays in order to identify potential hedgehog antagonist lead compounds, as well as to refine the specificity, toxicity, and/or cytotoxic-kinetic profile of a lead compound. For instance, ptc, hedgehog, or smoothened bioactivity assays, such as may be developed using cells with either a ptc loss-of-function, hedgehog gain-of-function, or smoothened gain-of-function, can be used to screen a library of the subject compounds for those having agonist activity toward ptc or antagonist activity towards hedgehog or smoothened.

Simply for illustration, a combinatorial library for the purposes of the present invention is a mixture of chemically related compounds that may be screened together for a desired property. The preparation of many related compounds in a single reaction greatly reduces and simplifies the number of screening processes that need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject hedgehog antagonists. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; the ArQule U.S. Pat. Nos. 5,736,412 and 5,712,171; Chen et al. (1994) JACS 116:2661: Kerr et al. (1993) JACS 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject hedgehog antagonists can be synthesized and screened for particular activity or property.

In an exemplary embodiment, a library of candidate hedgehog antagonists diversomers can be synthesized utilizing a scheme adapted to the techniques described in the Still et al. PCT publication WO 94/08051, e.g., being linked to a polymer bead by a hydrolyzable or photolyzable group, optionally located at one of the positions of the candidate antagonists or a substituent of a synthetic intermediate. According to the Still et al. technique, the library is synthesized on a set of beads, each bead including a set of tags identifying the particular diversomer on that bead. The bead library can then be "plated" with ptc loss-of-function, hedgehog gain-of-function, or smoothened gain-of-function cells for which an hedgehog antagonist is sought. The diversomers can be released from the bead, e.g. by hydrolysis.

The structures of the compounds useful in the present invention lend themselves readily to efficient synthesis. The nature of the structures, as generally described by formulas I to II, allows the combinatorial assembly of such compounds using some combination of Ar, $R_1$, X, Y, and Z moieties, as set forth above. For example, these subunits can be attached to the core ring through common acylation or alkylation reactions. The vast majority of such reactions are both extremely mild and extremely reliable, and are thus perfectly suited for combinatorial chemistry. Such combinatorial approaches may employ vacations on one of the routes disclosed below.

Many variations on the above and related pathways permit the synthesis of widely diverse libraries of compounds that may be tested as inhibitors of hedgehog function.

b. Screening Assays

There are a variety of assays available for determining the ability of a compound to agonize ptc function or antagonize smoothened or hedgehog function, many of which can be disposed in high-throughput formats. In many drug-screening programs that test libraries of compounds and natural extracts, high throughput assays are desirable in order to maximize the number of compounds surveyed in a given period of time. Thus, libraries of synthetic and natural products can be sampled for other compounds that are hedgehog antagonists.

In addition to cell-free assays, test compounds can also be tested in cell-based assays. In one embodiment, cell which have a ptc loss-of-function, hedgehog gain-of-function, or smoothened gain-of-function phenotype can be contacted with a test agent of interest, with the assay scoring for, e.g., inhibition of proliferation of the cell in the presence of the test agent.

A number of gene products have been implicated in patched-mediated signal transduction, including patched, transcription factors of the cubitus interruptus (ci) family, the serine/threonine kinase fused (fu) and the gene products of costal-2, smoothened and suppressor of fused.

The induction of cells by hedgehog proteins sets in motion a cascade involving the activation and inhibition of downstream effectors, the ultimate consequence of which is, in some instances, a detectable change in the transcription or translation of a gene. Potential transcriptional targets of hedgehog-mediated signaling axe the patched gene (Hidalgo and Ingham, 1990 *Development* 110, 291-301; Marigo et al., 1996) and the vertebrate homologs of the *drosophila* cubitus interruptus gene, the GLI genes (Hui et al. (1994) *Dev Biol* 162:402-413). Patched gene expression has been shown to be induced in cells of the limb bud and the neural plate that are responsive to Shh. (Marigo et al. (1996) *PNAS* 93:9346-51; Marigo et al. (1996) *Development* 122:1225-1233). The Gli genes encode putative transcription factors having zinc finger DNA binding domains (Orenic et al. (1990) *Genes & Dev* 4:1053-1067; Kinzler et al. (1990) *Mol Cell Biol* 10:634-642). Transcription of the Gli gene has been reported to be upregulated in response to hedgehog in limb buds, while transcription of the Gli3 gene is downregulated in response to hedgehog induction (Marigo et al. (1996) *Development* 122: 1225-1233). By selecting transcriptional regulatory sequences from such target genes, e.g., from patched or Gli genes, that are responsible for the up- or down-regulation of these genes in response to hedgehog signalling, and operatively linking such promoters to a reporter gene, one can derive a transcription based assay which is sensitive to the ability of a specific test compound to modify hedgehog-mediated signalling pathways. Expression of the reporter gene, thus, provides a valuable screening tool for the development of compounds that act as antagonists of hedgehog.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on ptc loss-of-function, hedgehog gain-of-function, smoothened gam-of-function, or stimulation by SHH itself. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic biological activity. The amount of expression from the reporter gene is then compared to the amount of expression in either the same cell in the absence of the test compound or it may be compared with the amount of transcription in a substantially identical cell that lacks the target receptor protein. Any statistically or otherwise significant decrease in the amount of transcription indicates that the test compound has in some manner agonized the normal ptc signal (or antagonized the gain-of-function hedgehog or smoothened signal), e.g., the test compound is a potential hedgehog antagonist c. Exemplified Compounds Table 1 contains some of the compounds that exemplify Formulas I, II, II, and IV. The examples in Table 1 are in no way meant to be limiting.

TABLE 1

| Example | Compound |
|---------|----------|
| 1 | 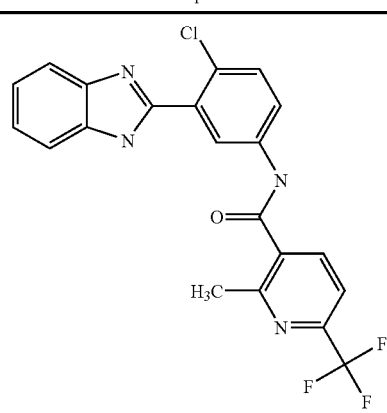 |

TABLE 1-continued

| Example | Compound |
|---|---|
| 2 | (structure) |
| 3 | (structure) |
| 4 | (structure) |
| 5 | (structure) |
| 6 | (structure) |
| 7 | (structure) |
| 8 | (structure) |

TABLE 1-continued

| Example | Compound |
|---|---|
| 9 | (structure) |
| 10 | (structure) |
| 11 | (structure) |
| 12 | (structure) |
| 13 | (structure) |
| 14 | (structure) |
| 15 | (structure) |

TABLE 1-continued
| Example | Compound |
|---|---|
| 16 |  |
| 17 | |
| 18 | |
| 19 | |
| 20 | 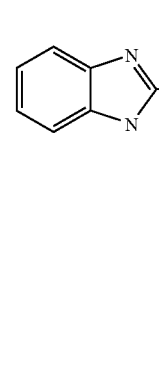 |
| 21 | |
| 22 | 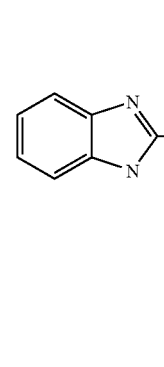 |

TABLE 1-continued

| Example | Compound |
|---|---|
| 23 | (structure) |
| 24 | (structure) |
| 25 | (structure) |
| 26 | (structure) |
| 27 | (structure) |
| 28 | (structure) |
| 29 | (structure) |
| 30 | (structure) |

TABLE 1-continued

| Example | Compound |
|---|---|
| 31 | (structure) |
| 32 | (structure) |
| 33 | (structure) |
| 34 | (structure) |
| 35 | (structure) |
| 36 | (structure) |
| 37 | (structure) |
| 38 | (structure) |

VII. Business Methods

One aspect of the present invention relates to a kit comprising a hedgehog antagonist, e.g., as described herein, for treating or preventing basal cell carcinoma in a patient preferably a human, and in association with instructions (written and/or pictorial) describing the use of the formulation for treatment or prevention of basal cell carcinoma, and, optionally, warnings of possible side effects and drug-drug or drug-food interactions.

Another aspect of the present invention relates to a kit comprising a hedgehog antagonist, e.g., as described herein, wherein the hedgehog antagonist is administered as part of a therapeutic or cosmetic application, such as those described above (e.g., regulation of neural tissues, bone and cartilage formation and repair, regulation of spermatogenesis, regulation of smooth muscle, regulation of lung, liver and other organs arising from the primative gut, regulation of hematopoietic function, and regulation of skin and hair growth), to a patient, preferably a human, in association with instructions (written and/or pictorial) describing the therapeutic or cosmetic application, and optionally, warnings of possible side effects and drug-drug or drug-food interactions.

The invention further contemplates a method for conducting a pharmaceutical business, comprising: (a) manufacturing a pharmaceutical preparation comprising a sterile pharmaceutical excipient and a hedgehog antagonist; and (b) marketing (e.g., providing promotional and/or informative presentations (such as displays, telemarketing, and lectures), products (such as trial samples of the preparation), and/or documentation (including leaflets, pamphlets, websites, posters, etc.)) to healthcare providers, such as doctors, hospitals, clinics, etc., a benefit of using the pharmaceutical preparation for treating or preventing basal cell carcinoma.

Another aspect of the present invention relates to a method for conducting a pharmaceutical business, comprising: (a) manufacturing a pharmaceutical preparation comprising a sterile pharmaceutical excipient and a hedgehog antagonist; and (b) marketing (e.g., providing promotional and/or informative presentations (such as displays, demonstrations, telemarketing, and lectures), products (such as trial samples of the preparation), and/or documentation (including leaflets, pamphlets, websites, posters, etc.)) to healthcare providers, such as doctors, hospitals, clinics, etc., a benefit of using the pharmaceutical preparation as part of a therapeutic or cosmetic application, such as regulation of neural tissues, bone and cartilage formation and repair, regulation of spermatogenesis, regulation of smooth muscle, regulation of lung, liver and other organs arising from the primative gut, regulation of hematopoietic function, and regulation of skin and hair growth.

Another aspect of the invention provides for a method for conducting a pharmaceutical business, comprising: (a) providing a distribution network for selling the pharmaceutical composition comprising a sterile pharmaceutical excipient and a hedgehog antagonist; and (b) providing instruction material to patients or physicians for using the pharmaceutical composition for treating or preventing basal cell carcinoma.

Another aspect of the invention provides for a method for conducting a pharmaceutical business, comprising: (a) providing a distribution network for selling the pharmaceutical composition comprising a sterile pharmaceutical excipient and a hedgehog antagonist; and (b) providing instruction material to patients or physicians for using the pharmaceutical composition as part of a therapeutic or cosmetic application, such as those described above (e.g., regulation of neural tissues, bone and cartilage formation and repair, regulation of spermatogenesis, regulation of smooth muscle, regulation of lung, liver and other organs arising from the primative gut, regulation of hematopoietic function, and regulation of skin and hair growth).

Another aspect of the invention provides for a method for conducting a pharmaceutical business, comprising: (a) determining an appropriate pharmaceutical preparation and dosage of a hedgehog antagonist for treatment or prevention of basal cell carcinoma; (b) conducting therapeutic profiling of the pharmaceutical composition for efficacy and toxicity in animals; (c) providing a distribution network for selling a pharmaceutical composition having an acceptable therapeutic profile; and, optionally, (d) providing a sales group for marketing the preparation to healthcare providers.

Another aspect of the invention provides for a method for conducting a pharmaceutical business, comprising: (a) determining an appropriate pharmaceutical preparation and dosage of a hedgehog antagonist for treatment or prevention of a medical or cosmetic condition described above; (b) conducting therapeutic profiling of the pharmaceutical composition for efficacy and toxicity in animals in treating or preventing the condition; (c) providing a distribution network for selling a pharmaceutical composition having an acceptable therapeutic profile for treating or preventing the condition; and, optionally, (d) providing a sales group for marketing the preparation to healthcare providers for the treatment or prevention of the condition.

Yet another aspect of the invention provides a method for conducting a pharmaceutical business, comprising: (a) determining an appropriate pharmaceutical composition and dosage of a hedgehog antagonist for treatment or prevention of basal cell carcinoma; and (b) licensing, to a third party, rights for further development and sale of the pharmaceutical composition.

Yet another aspect of the invention provides a method for conducting a pharmaceutical business, comprising: (a) determining an appropriate pharmaceutical composition and dosage of a hedgehog antagonist for treatment or prevention of a medical or cosmetic condition as described above; and (b) licensing, to a third party, rights for further development and sale of the pharmaceutical composition for the treatment or prevention of the condition.

EXEMPLIFICATION

The invention now being generally described, it will be more readily understood by reference to the following examples, which are included merely for purposes of illustration of certain aspects and embodiments of the present invention, and are not intended to limit the invention.

EXPERIMENTAL

Synthesis of Exemplary Inhibitors

Route 1

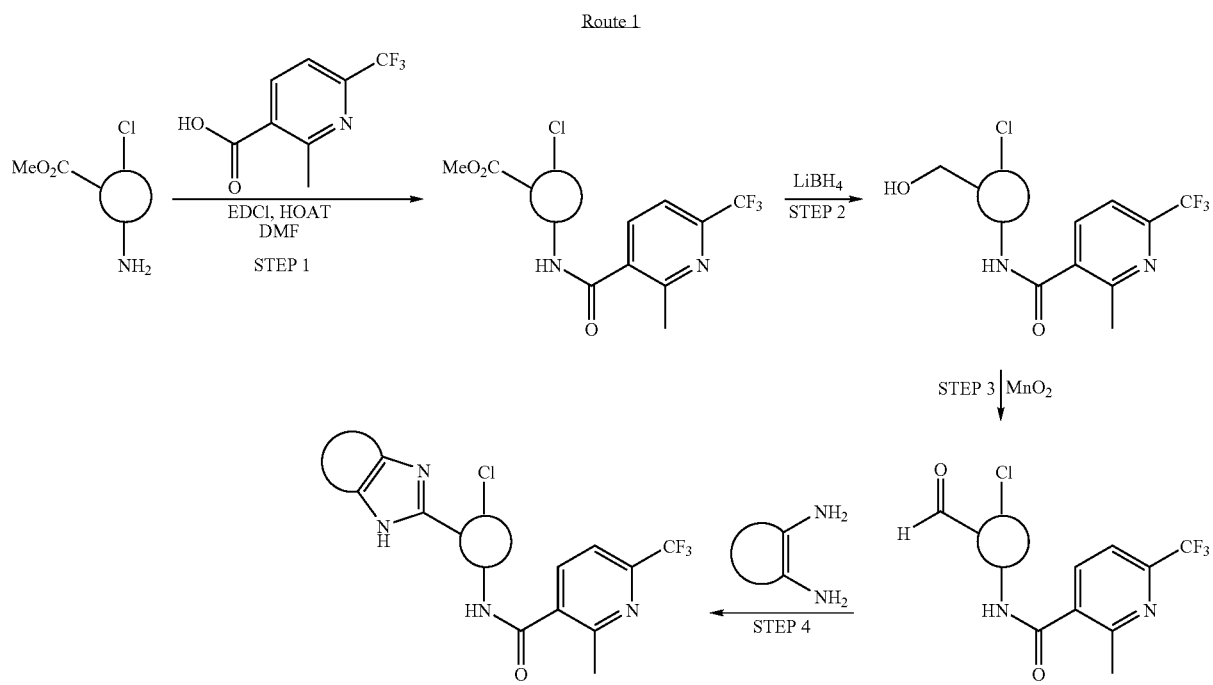

Exemplified for Compound 24

Compound 24

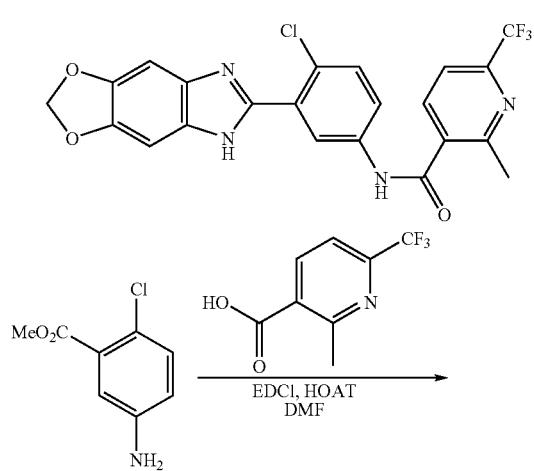

To a solution of 2-methyl-6-trifluoromethylnicotinic acid (4.77 g; 23 mmol) in dimethyl formamide (100 ml) was added 1-(3-dimethylaminopropyl)-3-ethylcarbodiimide hydrochloride (4.46 g; 23 mmol) and 1-hydroxy-7-azabenzotriazole (3.17 g; 23 mmol) and the resulting solution was stirred at room temperature for 30 minutes. To this was added a solution of methyl 5-amino-2-chlorobenzoate (3.6 g; 19 mmol) in dimethyl formamide (25 ml) and the resulting solution stirred at room temperature for 18 hours. Water (200 ml) was added to the reaction mixture and this was extracted with ethyl acetate (3×200 ml). The combined organic layers were washed with saturated sodium bicarbonate solution (2×300 ml). The organic layer was dried (magnesium sulphate), filtered and evaporated to give 2-chloro-5-[(2-methyl-6-trifluoromethyl-pyridine-3-carbonyl)-amino]-benzoic acid methyl ester (6.6 g, 94%).

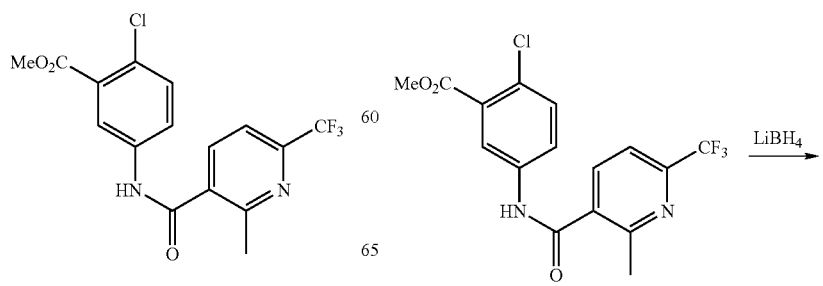

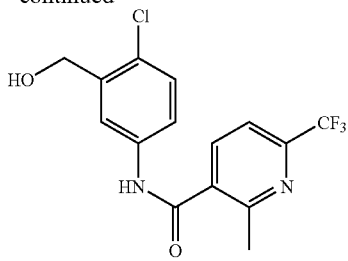

A solution of 2-chloro-5-[(2-methyl-6-trifluoromethyl-pyridine-3-carbonyl)-amino]-benzoic acid methyl ester (6.68 g; 18 mmol) in tetrahydrofuran (100 ml) was cooled to 0° C. Lithium borohydride (0.98 g; 45 mmol) was added portionwise and the reaction mixture allowed to warm to room temperature, followed by heating at 45° C. for 4 hours. The reaction was allowed to cool to room temperature and saturated sodium bicarbonate solution (100 ml) was added. This was extracted with ethyl acetate (3×50 ml). The organic layers were dried (magnesium sulphate), filtered and evaporated. The residue was purified by column chromatography (50% ethyl acetate in heptane) to give N-(4-chloro-3-hydroxymethyl-phenyl)-2-methyl-6-trifluoromethyl-nicotinamide (3.29 g, 54%).

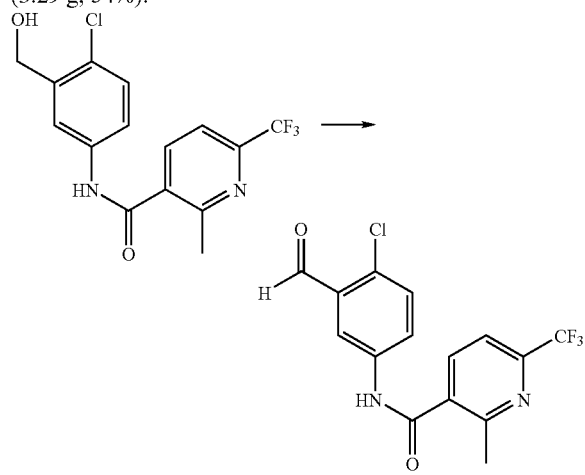

To a suspension of N-(4-chloro-3-hydroxymethyl-phenyl)-2-methyl-6-trifluoromethyl-nicotinamide (3.29 g; 9.56 mmol) in dichloromethane (300 ml) was added manganese dioxide (8.31 g; 95.6 mmol) and the resulting mixture stirred at room temperature for 30 minutes. Analysis after this time showed a 60% conversion to product. Further manganese dioxide (8 g; 92 mmol) was added in three portions over the next 90 minutes. The reaction mixture was then filtered through celite and the filtrate evaporated to give N-(4-chloro-3-formyl-phenyl)-2-methyl-6-trifluoromethyl-nicotinamide (3.2 g, 97%).

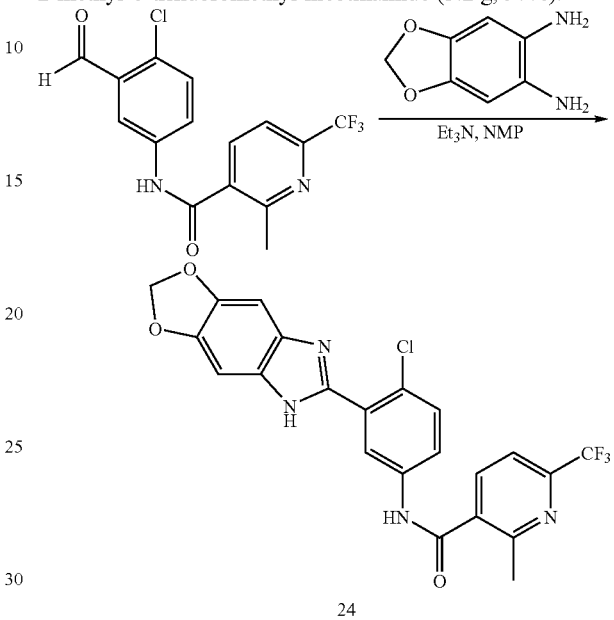

24

To a solution of N-(4-chloro-3-formyl-phenyl)-2-methyl-6-trifluoromethyl nicotinamide (152 mg; 0.44 mmol) and benzo[1,3]dioxole-5,6-diamine (100 mg; 0.44 mmol) in N-methylpyrrolidone (3 ml) was added triethylamine (0.12 ml; 0.88 mmol). The resulting solution was heated to 100° C. for 1 hour. Water (10 ml) was added to the cooled reaction mixture and this was extracted with ethyl acetate (3×10 ml). The organic layer was dried (magnesium sulphate), filtered and evaporated to give the crude residue. This was purified by column chromatography (30% ethyl acetate in heptane) to give compound 24 (146 mg, 70%): $^1$H NMR (400 MHz, MeOD) δ 8.45 (s, 1H), 8.0 (d, 1H), 7.65-7.75 (m, 3H), 7.2 (s, 2H), 6.1 (s, 2H>, 2.65 (s, 3H); MS (ES$^+$); 475 ($^{35}$Cl), 477 ($^{37}$Cl) [M$^+$+1].

Route 2

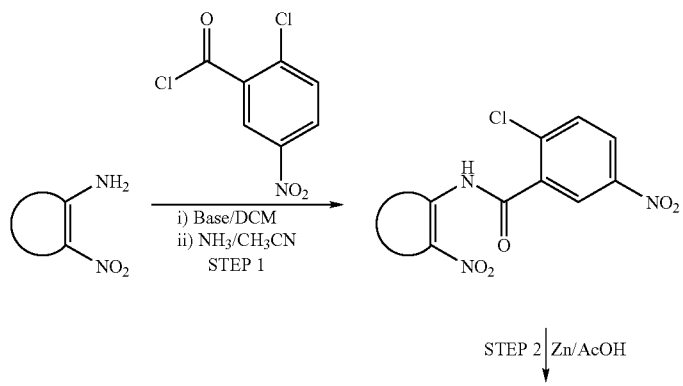

STEP 2 | Zn/AcOH

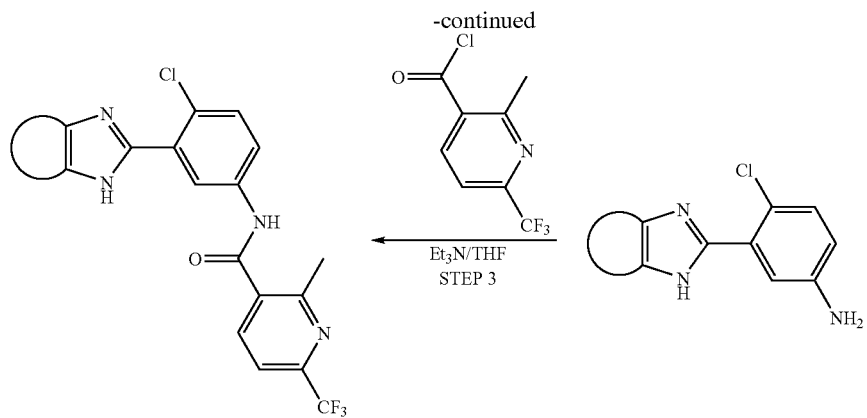

Exemplified for Compound 5

Compound 5

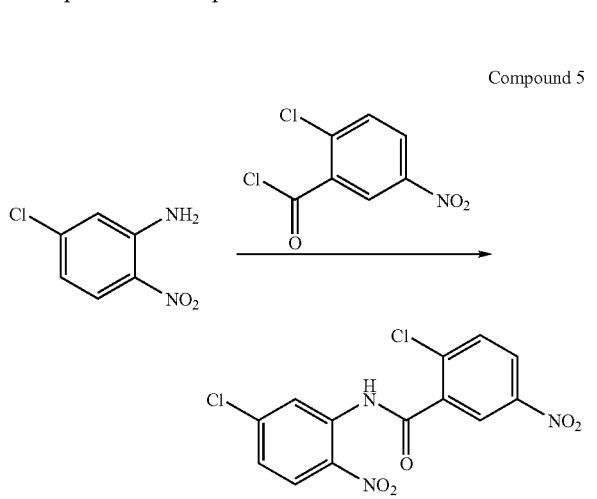

5-Chloro-2-nitroaniline (1 g; 5.8 mmol) and pyridine (0.64 ml; 8.1 mmol) were dissolved in dichloromethane (10 ml) and cooled to 0° C. This was added drop wise over 5 minutes to a solution of 2-chloro-5-nitrobenzoyl chloride (1.34 g; 6.1 mmol) in dichloromethane (5 ml). The reaction was stirred at room temperature for 72 hours before adding further acid chloride (1.34 g) and pyridine (0.64 ml). After 30 minutes, the solvent was evaporated and the bisacylated residue treated with 1:1 concentrated ammonia/acetonitrile (10 ml). All the solvent was removed after 5 minutes and the residue crystallised from 1:1 chloroform/heptane (30 ml) to give 2-chloro-N-(5-chloro-2-nitro-phenyl)-5-nitro-benzamide (1.78 g, 86%)

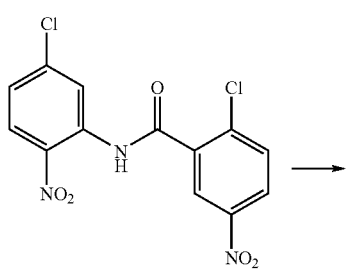

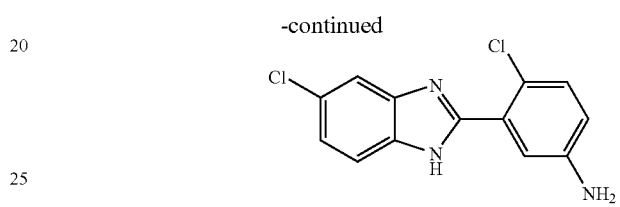

2-Chloro-N-(5-chloro-2-nitro-phenyl)-5-nitro-benzamide (1.78 g; 5 mmol) was dissolved in glacial acetic acid (30 ml) and heated to 70° C. Zinc powder (3.3 g; 50 mmol) was added portionwise. After 2 hours, the reaction was filtered and the solid washed with acetonitrile. The solvents were evaporated and the residue loaded onto a silica gel chromatography column using dichloromethane/triethylamine. Elution with 20% ethyl acetate in heptane gave 4-chloro-3-(5-chloro-1H-benzoimidazol-2-yl)-phenylamine as an orange powder (0.22 g, 16%).

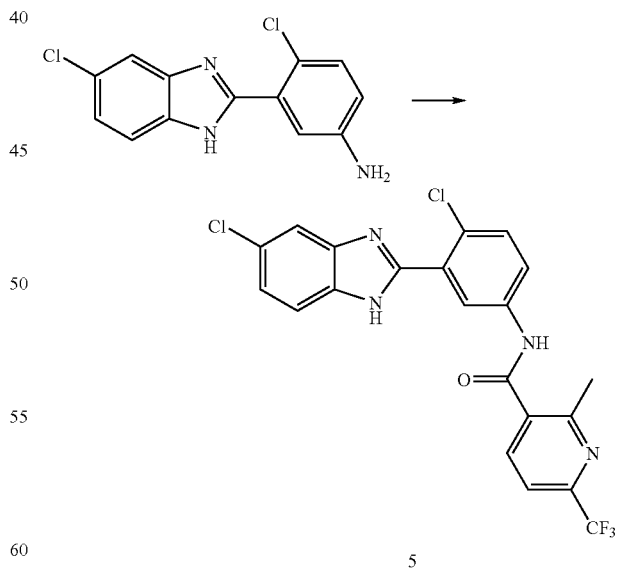

4-Chloro-3-(5-chloro-1H-benzoimidazol-2-yl)-phenylamine (80 mg; 0.29 mmol) and triethylamine (23 μl; 0.32 mmol) were dissolved in tetrahydrofuran (2 ml). A solution of 2-methyl-6-trifluoromethylnicotinoyl chloride (58 mg; 0.26 mmol) in tetrahydrofuran (1 ml) was added over 5 minutes.

After stirring for 6 hours at room temperature, the solvent was evaporated and the residue loaded onto a silica gel chromatography using a dichloromethane/methanol mixture. Elution with 10% methanol in dichloromethane gave compound 5 as the free base. This was dissolved in methanol (1 ml) and concentrated hydrochloric acid (2 drops) added. Evaporation provided the hydrochloride salt (56 mg, 43%); $^1$H NMR (400 MHz, d$_6$ DMSO) δ11.1 (s, 1H), 8.45 (s, 1H), 8.25 (d, 1H), 7.9 (m, 2H), 7.85 (s, 1H), 7.75 (m, 2H), 7.45 (d, 1H), 2.65 (s, 3H); MS (ES$^+$): 465 ($^{35}$Cl), 467 ($^{37}$Cl) [M$^+$+1], Compound 2

Compound 2 was prepared from 5-dimethylamino-2-nitroaniline using route 2: $^1$H NMR (400 MHz, d$_6$ DMSO) δ 11.35 (brs, 1H), 8.6 (s, 1H), 8.4 (d, 1H), 8.1 (m, 3H), 7.95 (d, 1H), 7.6-7.7 (brm, 1H), 3.3 (s, 6H), 2.85 (s, 3H); MS (ES$^+$): 474 ($^{35}$Cl), 476 ($^{37}$Cl) [M$^+$+1].

Compound 3

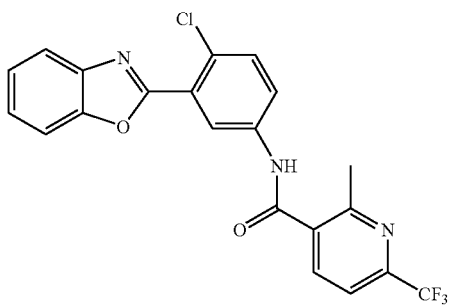

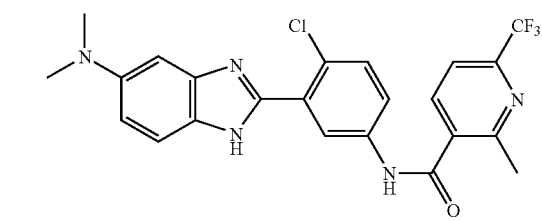

5-Chloro-2-nitroaniline (50 g; 0.29 mol) was added to a 5 L bomb followed by ethanol (1.1 L) at 0-5° C. Dimethylamine hydrochloride (130 g; 1.59 mmol) was added in one portion followed by triethylamine (260 ml) and the bomb quickly sealed. The bomb was heated to 130° C. with stirring at 4 bar for 20 hours. The reaction mixture was then allowed to cool to room temperature and the ethanol was removed under vacuum. 2 M sodium hydroxide solution (1 L) was added to the crude residue and this was extracted with ethyl acetate (1×1.3 L then 2×500 ml). The combined organic layers were washed with brine (150 ml), dried (magnesium sulphate), filtered and evaporated to give the 5-dimethylamino-2-nitroaniline (50.1 g, 96%).

2-Aminophenol (300 mg; 2.75 mmol) and 2-chloro-5-nitrobenzoyl chloride (606 mg; 2.75 mmol) were dissolved in N-methylpyrrolidone (6 ml) and heated at 100° C. for 24 hours. The reaction was cooled to room temperature, partitioned between ethyl acetate and saturated sodium bicarbonate, and the organic layer dried (sodium sulphate). After filtration and evaporation, the product was purified by column chromatography on silica gel. 2-(2-Chloro-5-nitro-phenyl)-benzooxazole eluted with 40% ethyl acetate in heptane (320 mg, 42%)

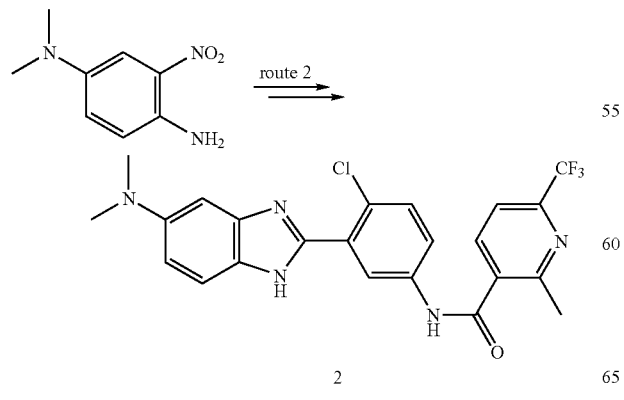

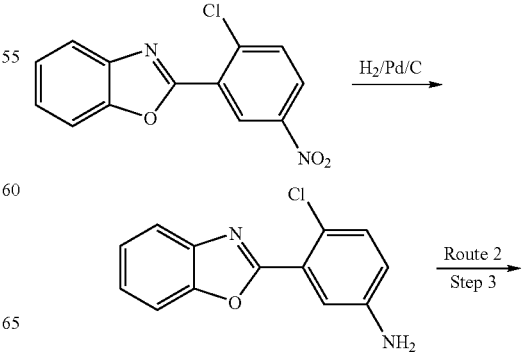

-continued

3

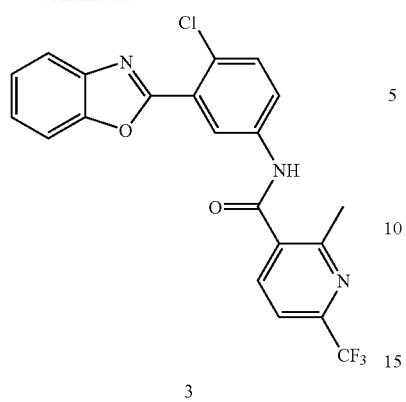

2-(2-Chloro-5-nitro-phenyl)-benzooxazole was reduced to the aniline as described for compound 16 and the aniline converted to compound 3 as in route 2 step 3. $^1$H NMR (400 MHz, d$_6$ DMSO) δ11.25 (s, 1H), 8.95 (s, 1H), 8.55 (d, 1H), 8.1-8.2 (m, 4H), 8.0 (d, 1H), 7.7-7.8 (m, 2H), 2.95 (s, 3H); MS (ES$^+$): 432 ($^{35}$Cl), 434 ($^{37}$Cl) [M$^+$+1].

Compound 6

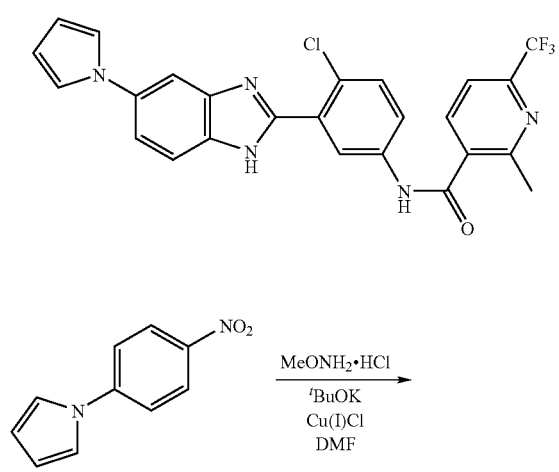

2-Nitro-5-(1-pyrrolo)aniline was prepared using the procedure described for compound 11.

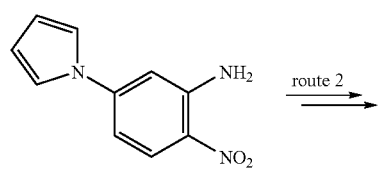

-continued

6

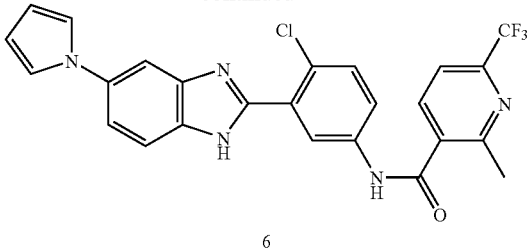

Compound 6 was prepared from 2-nitro-5-(1-pyrrolo)aniline using route 2: $^1$H NMR (400 MHz, MeOD) δ 8.55 (s, 1H), 8.05 (d, 1H), 7.85 (dd, 2H), 7.75 (d, 2H), 7.7 (dd, 2H), 7.25 (s, 2H), 6.25 (s, 2H), 2.65 (s, 3H); MS (ES$^+$): 496 ($^{35}$Cl), 498 ($^{37}$Cl) [M$^+$+1].

Compound 7

7

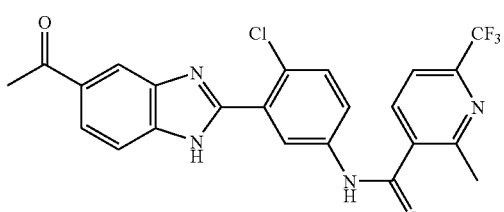

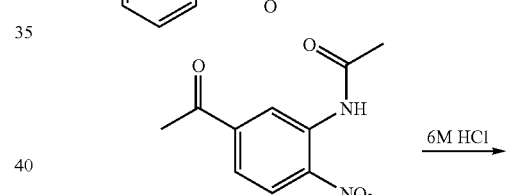

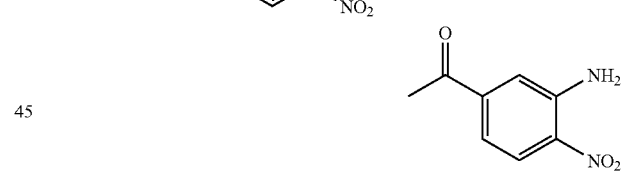

Fuming white nitric acid (3.6 g) was added dropwise to acetic anhydride (12 ml) at 0° C. and stirred for 15 minutes. The N-(3-acetyl-phenyl)-acetamide (2 g; 11.3 mmol) was then added portionwise and the reaction mixture allowed to warm to room temperature. After stirring at room temperature for 15 minutes, the reaction mixture was poured onto ice (200 ml). Dichloromethane (200 ml) was added and the organic layer was separated, dried (magnesium sulphate), filtered and evaporated to give the crude residue. This was purified by column chromatography to give N-(5-acetyl-2-nitro-phenyl)-acetamide (515 mg), which was directly hydrolysed by heating in 6M hydrochloric acid (15 ml) at 80° C. for 2 hours. The cooled reaction mixture was basified using saturated sodium bicarbonate solution and then extracted into ethyl acetate (6×30 ml). The organic layers were dried (magnesium sulphate), filtered and evaporated to give the crude residue. This was purified by column chromatography (50% ethyl acetate in heptane) to give 3-amino-4-nitroacetophenone (226 mg, 11%).

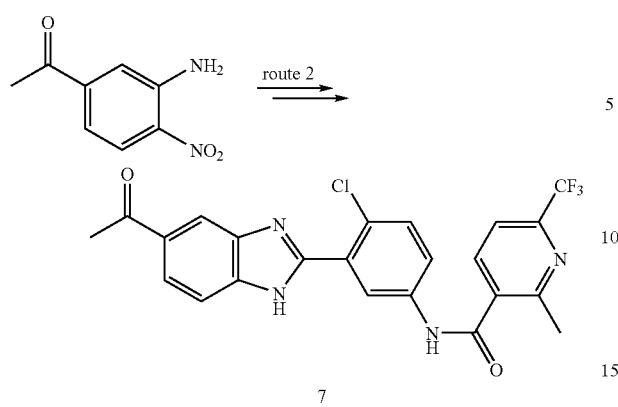

7

Compound 7 was prepared from 3-amino-4-nitroacetophenone using route 2: $^1$H NMR (400 MHz, MeOD) δ 8.2 8.3 (bis, 1H), 8.15 (s, 1H), 8.05 (d, 1H), 7.95 (d, 1H), 7.85 (d, 1H), 7.7 (d, 1H), 7.65 (brs, 1H), 7.55 (d, 1H), 2.65 (s, 3H), 2.60 (s, 3H); MS (ES$^+$): 473 ($^{35}$Cl), 475 ($^{37}$Cl) [M$^+$+1].

Compound 8

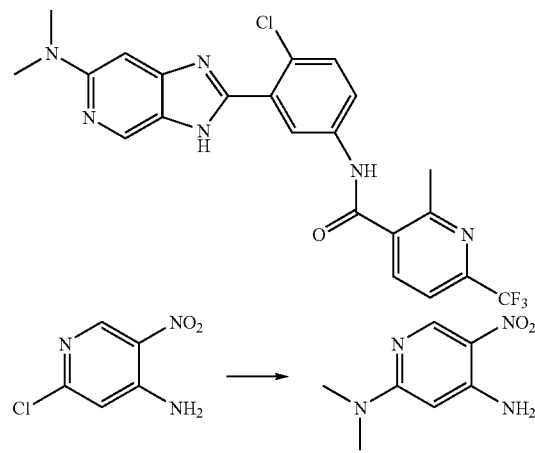

In a microwave tube, a solution of 4-amino-2-chloro-5-nitropyridine (prepared as described for compound 9) (200 mg; 1.16 mmol) in ethanol (2 ml) was treated sequentially with dimethylamine hydrochloride (471 mg; 5.78 mmol) and triethylamine (781 μl; 6.96 mmol). The tube was quickly sealed and irradiated in the microwave (CEM Discover, 150 W, 85° C., 10 min). The ethanol was evaporated, dichloromethane (15 ml) was added to dissolve the products, and the solution washed with 1M sodium hydroxide solution (2×10 ml). The organic layer was dried (sodium sulphate), the mixture filtered and the filtrate evaporated to dryness to afford N$^2$,N$^2$-dimethyl-5-nitro-pyridine-2,4-diamine (240 mg, 114%).

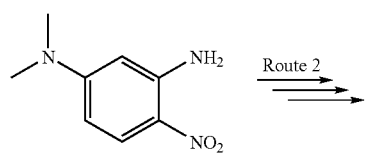

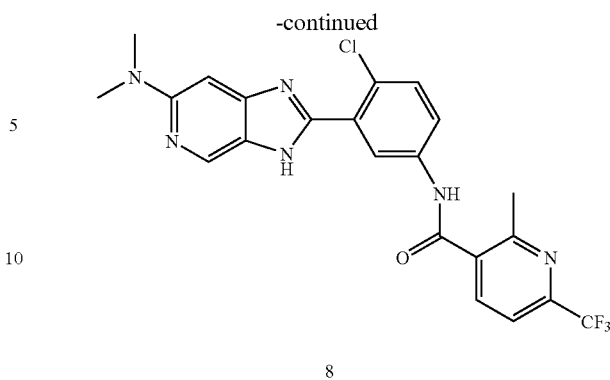

8

N$^2$,N$^2$-dimethyl-5-nitro-pyridine-2,4-diamine was converted into compound 8 using the method described in route 2: $^1$H NMR (400 MHz, MeOD) δ 8.44 (s, 1H), 8-8.13 (s, 1H), 8.00 (d, 1H), 7.78 (d, 1H), 7.64 (d, 1H), 7.52 (d, 1H), 6.55 (bs, 1H), 3.04 (s, 6H) and 2.58 (s, 3H); MS (ES$^+$): 475 ($^{35}$Cl), 477 ($^{37}$Cl) [M$^+$+1].

Compound 9

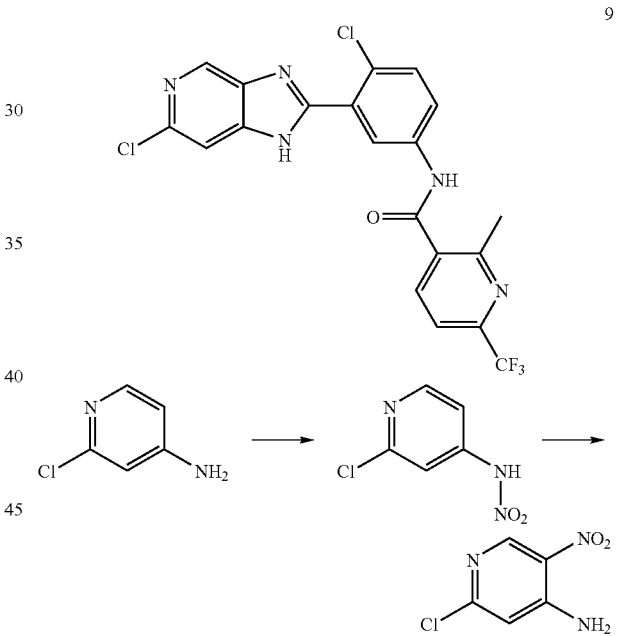

To stirred concentrated sulphuric acid (100 ml) at 4° C. was added 2-chloro-4-aminopyridine (35.0 g; 0.273 mol) in portions. White fuming nitric acid (26 ml) was added dropwise over 20 minutes and the mixture stirred at 4° C. for 1 hour before being poured onto ice (1 L). The resultant mixture was taken to pH 2 with 6 M NaOH at which point a thick precipitate formed. This was filtered, washed with water and dried in air to afford the nitramine intermediate which was used in the next step without further purification.

A solution of the nitramine (42 g) in concentrated sulphuric acid (100 ml) was heated at 85° C. for 2 hours, then at 110° C. for a further 1 hour. The mixture was cooled, poured into ice (1 L) and basified with concentrated ammonia solution to pH 9. The resultant suspension was filtered and the solid washed with water. The solid was then extracted with hot toluene (3×250 ml), and the combined extracts evaporated and chromatographed (heptane: ethyl acetate 9:2) to afford 2-chloro-4-amino-5-nitropyridine as a white solid (4.57 g, 10%); ¹H NMR (400 MHz, DMSO) δ 8.85 (1H, d), 7.90-8.22 (2H, bs) and 6.90 (1H, d).

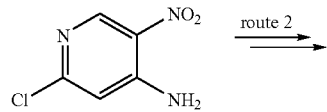

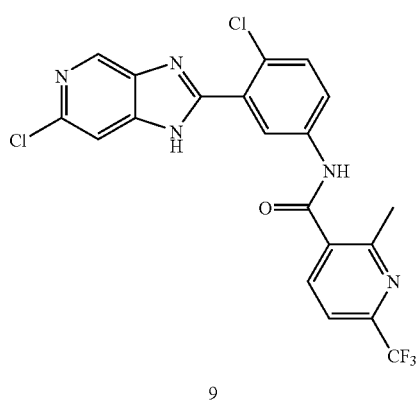

4-Amino-2-chloro-5-nitropyridine was converted into compound 9 using route 2: ¹H NMR (400 MHz, MeOD) δ 8.64 (s, 1H), 8.21 (s, 1H), 8.03 (d, 1H), 7.82 (d, 1H), 7.65 (d, 1H), 7.58-7.56 (m, 2H) and 2.60 (s, 3H); MS (ES⁺): 466 (³⁵Cl, ³⁵Cl), 468 (³⁵Cl, ³⁷Cl), 470 (³⁷Cl, ³⁷Cl) [M⁺+1].

Compound 10

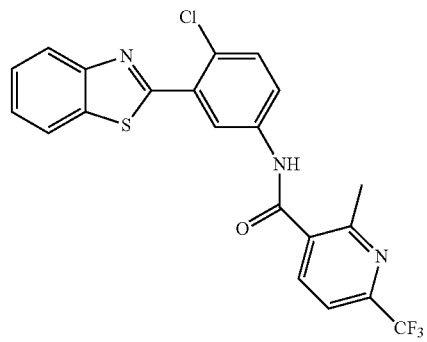

Compound 10 was prepared from 2-aminothiophenol using the method described in route 1 step 4: ¹H NMR (400 MHz, MeOD) δ 8.45 (s, 1H), 8-8.05 (m, 3H), 7.8 (d, 1H), 7.65 (d, 1H), 7.5-7.55 (m, 2H), 7.4 (dd, 1H), 2.65 (s, 3H); MS (ES⁺): 448 (³⁵Cl), 450 (³⁷Cl) [M⁺+1].

Compound 11

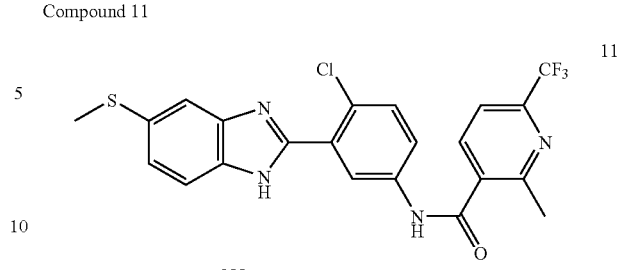

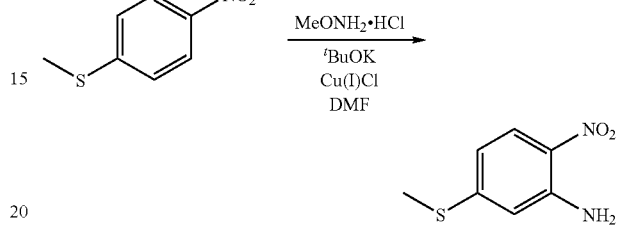

To a solution of potassium tert-butoxide (865 mg; 7.08 mmol) and copper (I) chloride (23 mg; 0.24 mmol) in dimethyl formamide (4 ml) was added a solution of 4-methylthionitrobenzene (400 mg; 2.36 mmol) and methoxyamine hydrochloride (247 mg; 2.96 mmol) in dimethyl formamide (4 ml) under nitrogen. The resulting solution was heated to 40° C. for 1.5 hours. The reaction mixture was then added to saturated ammonium chloride solution (10 ml) and extracted into dichloromethane (3×10 ml). The combined organic layers were dried (magnesium sulphate), filtered and evaporated to give the crude residue, which was purified by column chromatography (30% ethyl acetate in heptane) to give 5-methylthio-2-nitroaniline (190 mg, 44%).

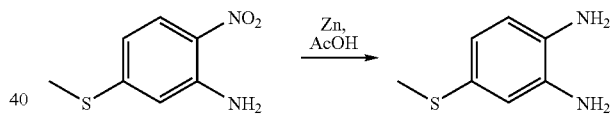

A solution of 5-methylthio-2-nitroaniline (50 mg; 0.27 mmol) in acetic acid (2 ml) was heated to 85° C. Zinc powder (71 mg; 1.09 mmol) was then added portionwise over 15 minutes and the resulting solution was maintained at 85° C. for 2 hours. The hot reaction mixture was then filtered through celite and the filter cake washed with hot acetic acid (10 ml). The filtrate was evaporated to dryness to give crude 4-methylthio-1,2-phenylenediamine (42 mg, 100%). This was used directly in the next step without purification.

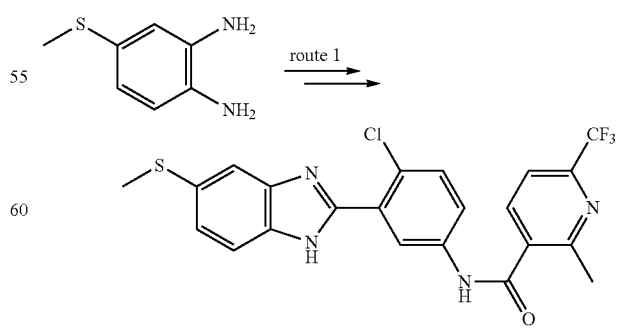

Compound 11 was prepared from 4-methylthio-1,2-phenylenediamine using route 1: $^1$H NMR (400 MHz, MeOD) δ 8.55 (s, 1H), 8.05 (d, 1H), 7.65-7.75 (m, 4H), 7.6 (s, 1H), 7.5 (d, 1H), 2.65 (s, 3H), 2.55 (s, 3H); MS (ES$^+$): 477 ($^{35}$Cl), 479 ($^{37}$Cl) [M$^+$+1].

Compound 12

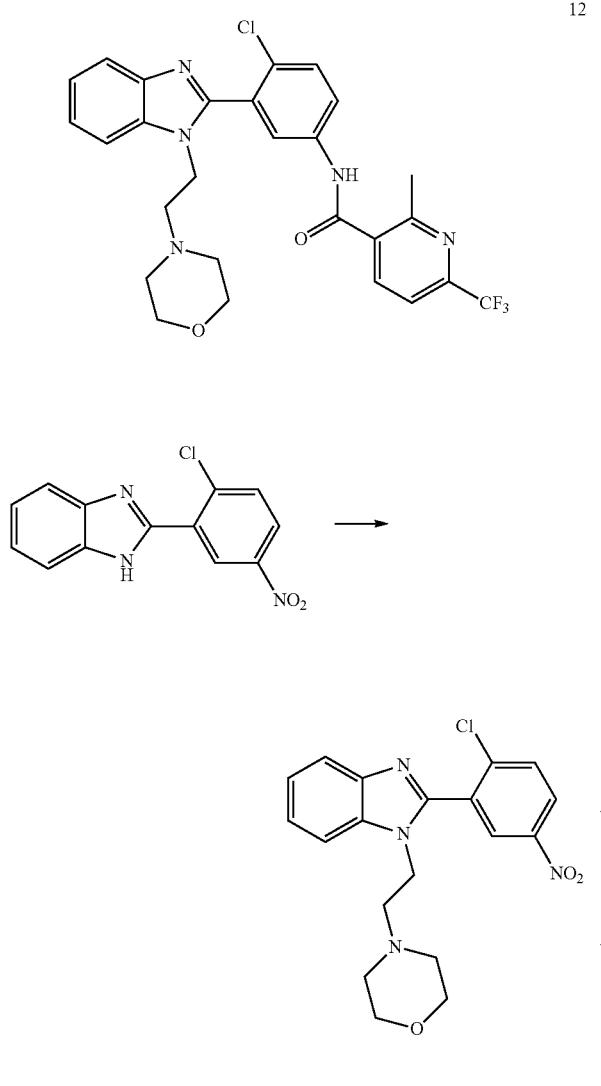

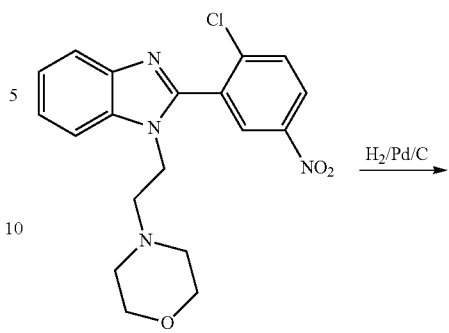

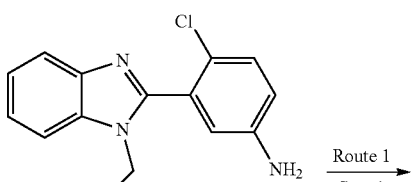

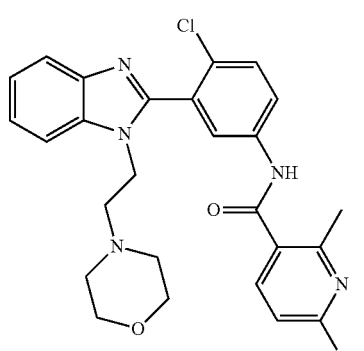

2-(2-Chloro-5-nitrophenyl)benzimidazole (100 mg; 0.37 mmol) was dissolved in dimethyl formamide (1 ml) and 60% sodium hydride in oil (19 mg; 0.85 mmol) added. This was heated at 40° C. for 20 minutes while 4-(2-chloroethyl)morpholine hydrochloride (136 mg; 0.73 mmol) was free-based by suspending in dimethyl formamide (1 ml) and adding 60% sodium hydride in oil (19 mg; 0.85 mmol). After 20 minutes the solutions were combined and heated at 45° C. for 75 minutes and 85° C. for 1.5 hours. The bulk of the solvent was then removed and the residue partitioned between ethyl acetate and water. The organic phase was dried (sodium sulphate), filtered and evaporated. The residue was chromatographed on silica gel and 2-(2-chloro-5-nitro-phenyl)-1-(2-morpholin-4-yl-ethyl)-1H-benzoimidazole eluted with 40% ethyl acetate in heptane (83 mg, 58%).

The nitro group was hydrogenated using the method described for compound 16 and this was then capped to give compound 12 as in route 1 step 1: $^1$H NMR (400 MHz, MeOD) δ 8.15 (s, 1H), 8.1 (d, 1H), 7.85 (d, 1H), 7.75 (d, 1H), 7.7 (d, 1H), 7.65 (m, 2H), 7.3-7.4 (m, 2H), 4.25-4.35 (brs, 2H), 3.45-3.5 (brm, 4H), 2.7 (s, 3H), 2.6-2.7 (brm, 2H), 2.2-2.25 (brm, 4H); MS (ES$^+$): 544 ($^{35}$Cl), 546 ($^{37}$Cl) [M$^+$+1].

Compound 13

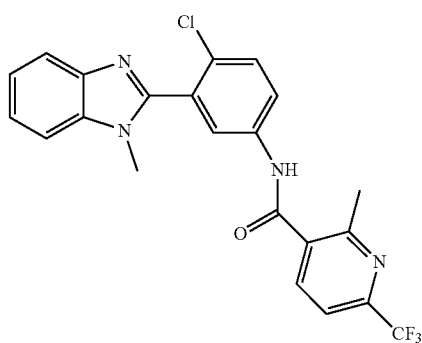

Compound 1 (50 mg; 0.12 mmol) was suspended in acetone (2 ml). 2 M methyl iodide in t-butyl methyl ether (70/d; 0.14 mmol) was added followed by 1 M sodium hydroxide in water (0.1 ml). The reaction was stirred at room temperature for 1.5 hours then more base was added and stirring continued for another 2 hours. Water (3 ml) was added and the mixture extracted with ethyl acetate (2×3 ml). The combined organic phases were washed with water (2×2 ml), dried (sodium sulphate), filtered and evaporated. The residue was chromatographed on silica gel and compound 13 eluted with 25% ethyl acetate in heptane (21 mg, 41%).

This was converted into the HCl salt as described in route 2 step 3: $^1$H NMR (400 MHz, MeOD) δ 8.4 (s, 1H), 8.1 (d, 1H), 7.95 (d, 1H), 7.9 (d, 1H), 7.85 (d, 1H), 7.75 (d, 1H), 7.73 (d, 1H), 7.65-7.7 (m, 2H), 3.95 (s, 3H), 2.65 (s, 3H); MS (ES$^+$): 445 ($^{35}$Cl), 447 ($^{37}$Cl) [M$^+$+1].

Compound 14

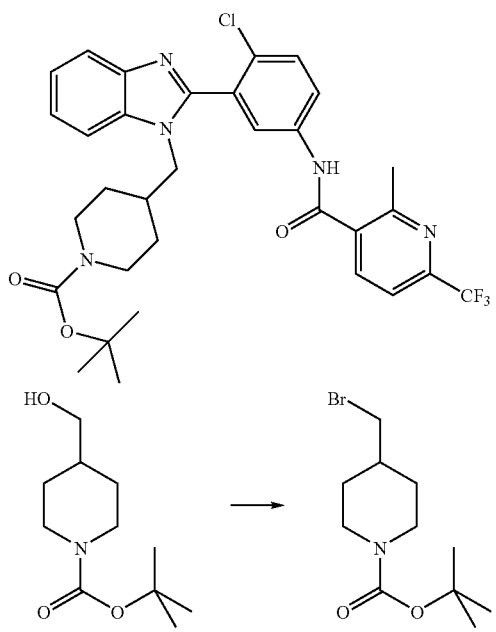

N-BOC piperidine-4-methanol (1 g; 46.5 mmol) and carbon tetrabromide (1.7 g; 51.3 mmol) were dissolved in dichloromethane (20 ml) and cooled to 0° C. Triphenyl phosphine (0.98 g; 37.3 mmol) was added and the reaction stirred at room temperature for 16 hours. Further triphenyl phosphine: (0.4 g; 15.7 mmol) and carbon tetrabromide (0.24 g; 7.2 mmol) were added and stirring continued for 6 hours. The solvent was evaporated and the residue chromatographed on silica. N-BOC piperidine-4 methyl bromide was eluted with 20% ethyl acetate in heptane (1.22 g, 94%).

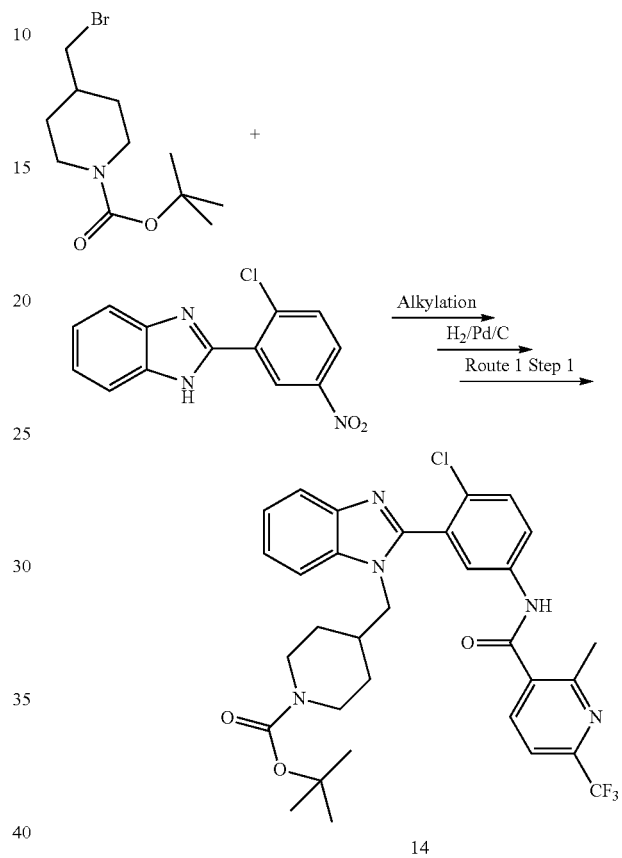

N-BOC piperidine-4 methyl bromide was converted into compound 14 using the method described for compound 12: $^1$H NMR (400 MHz, MeOD) δ 8.2 (d, 1H), 8.1 (s, 1H), 7.95 (d, 1H), 7.8 (d, 1H), 7.75 (d, 1H), 7.7-7.75 (m, 2H), 7.35-7.45 (m, 2H), 4.1-4.2 (brm, 2H), 4.0 (brd, 2H), 2.75 (s, 3H), 2.6-2.7 (brm, 4H), 2.0-2.15 (brm, 1H), 1.45 (s, 9H), 1-1.15 (brm, 4H); MS (ES$^+$): 628 ($^{35}$Cl), 630 ($^{37}$Cl) [M$^+$+1].

Compound 15

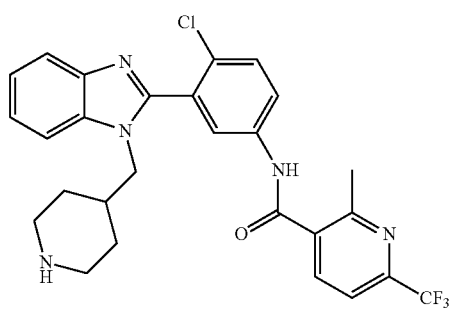

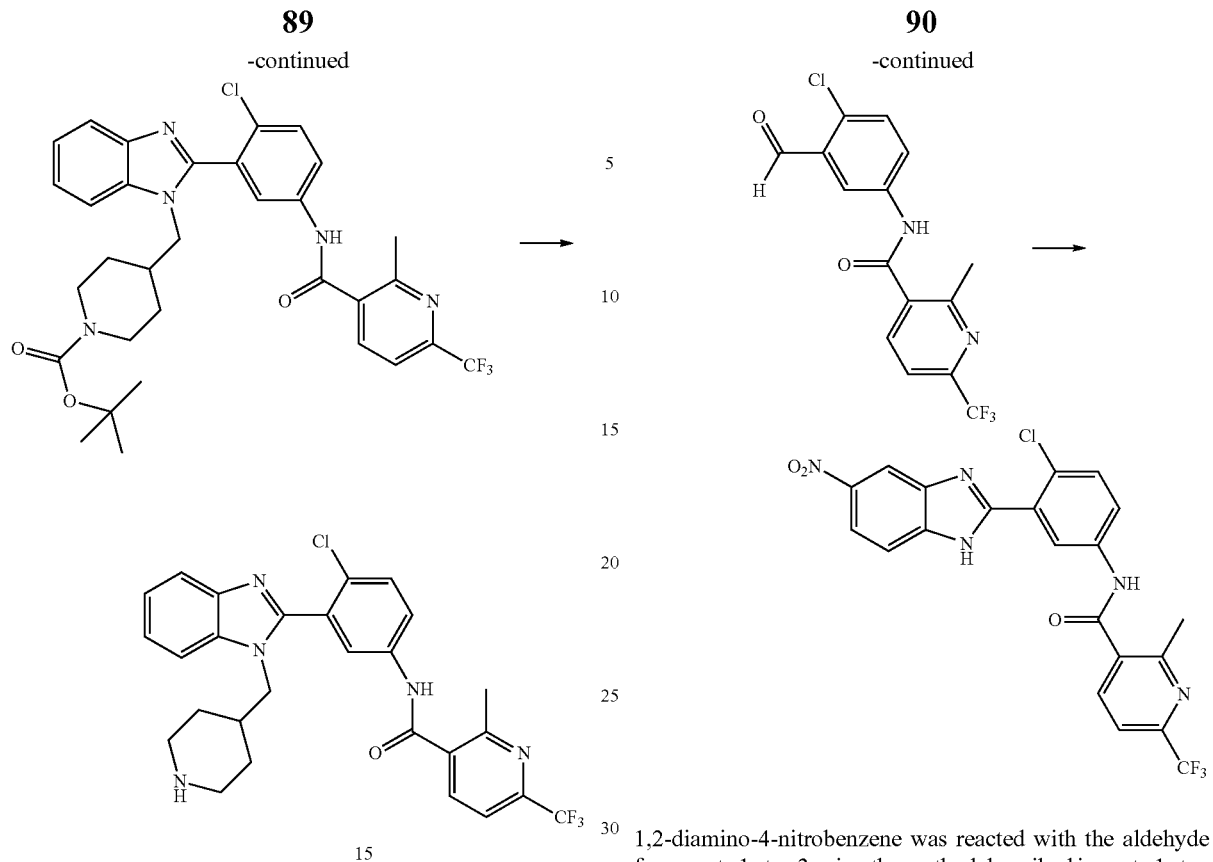

Compound 14 (26 mg; 0.041 mmol) was dissolved in ethanol (1 ml) and concentrated hydrochloric acid (0.5 ml) added. After 2.5 hours stirring at room temperature, the solvent was evaporated to give compound 15 as the dihydrochloride salt (16 mg, 73%): $^1$H NMR (400 MHz, MeOD) δ 8.05 (d, 1H), 7.95 (s, 1H), 7.8 (d, 1H), 7.67 (d, 1H), 7.62 (d, 1H), 7.55 (m, 2H), 7.25-7.35 (m, 2H), 3.95-4.05 (brm, 2H), 2.85 (brd, 2H), 2.65 (s, 3H), 2.35 (brt, 2H), 1.9 (brm, 1H), 1.3-1.4 (brm, 2H), 0.95-1.05 (brm, 2H); MS (ES$^+$): 528 ($^{35}$Cl), 530 ($^{37}$Cl) [M$^+$+1].

Compound 16

1,2-diamino-4-nitrobenzene was reacted with the aldehyde from route 1 step 3 using the method described in route 1 step 4 to give N-[4-chloro-3-(5-nitro-1H-benzoimidazol-2-yl)-phenyl]-2-methyl-6-trifluoromethyl-nicotinamide.

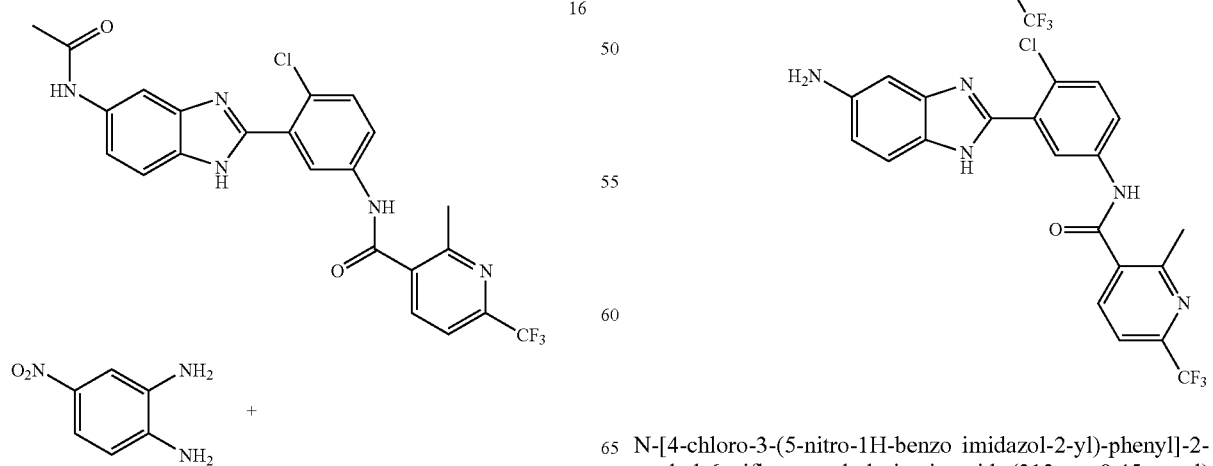

N-[4-chloro-3-(5-nitro-1H-benzo imidazol-2-yl)-phenyl]-2-methyl-6-trifluoromethyl-nicotinamide (212 mg; 0.45 mmol) was dissolved in ethanol (4 ml) with 2 drops of concentrated hydrochloric acid. This was added to 5% palladium on charcoal (42 mg; 20 wt %) and the reaction stirred under an atmosphere of hydrogen for 3 hours. The catalyst was removed by filtering through celite and then the solvent by evaporation to leave N-[3-(5-amino-1H-benzoimidazol-2-yl)-4-chloro-phenyl]-2-methyl-6-trifluoromethyl-nicotinamide (198 mg, 100%).

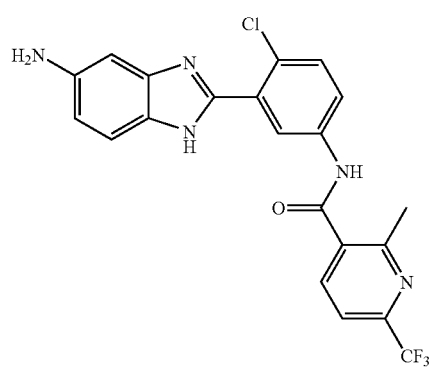

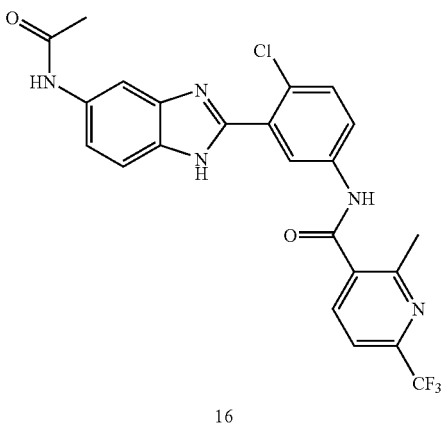

N-[3-(5-amino-1H-benzoimidazol-2-yl)-4-chloro-phenyl]-2-methyl-6-trifluoromethyl-nicotinamide (198 mg; 0.45 mmol) was dissolved in tetrahydrofuran (2 ml) and cooled to 0° C. 60% Sodium hydride in oil (80 mg; 2.0 mmol) was added and, after 30 minutes, acetyl chloride (156 mg; 2.0 mmol). The reaction was stirred at room temperature for 48 hours, 1.2M hydrochloric acid (4 ml) was added and stirring continued for 4.5 hours. The mixture was basified with saturated sodium bicarbonate solution, extracted with ethyl acetate, dried (sodium sulphate), filtered and evaporated. Chromatography on silica gel eluting with 100% ethyl acetate gave compound 16 (46 mg, 21%); $^1$H NMR (400 MHz, MeOD) δ 8.43 (m, 1H), 8.39 (s, 1H), 8.04 (d, 1H), 7.74 (d, 1H), 7.65 (m, 3H), 7.45 (d, 1H), 2.61 (s, 3H) and 2.10 (s, 3H); MS (ES$^+$): 488 ($^{35}$Cl), 490 ($^{37}$Cl) [M$^+$+1].

Compound 17

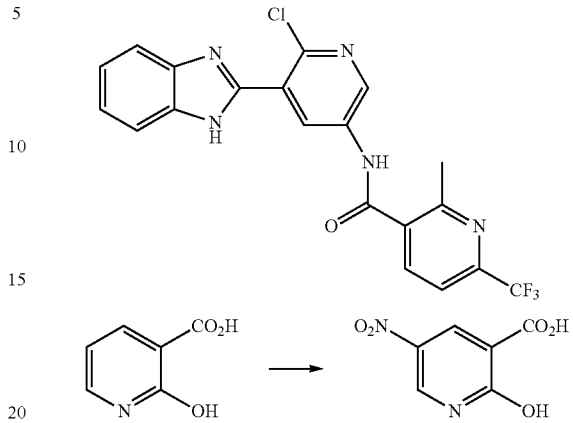

Concentrated sulphuric acid (73 ml) was cooled to 0° C. before adding 2-hydroxynicotinic acid (25 g; 0.18 moles) portionwise. Fuming nitric acid (17.5 ml) was added dropwise, also at 0° C., and the reaction then heated at 50° C. for 4 hours. The mixture was cooled to room temperature then poured over ice/water. The resulting precipitate of 2-hydroxy-5-nitronicotinic acid was filtered, washed with water and dried (29 g, 88%).

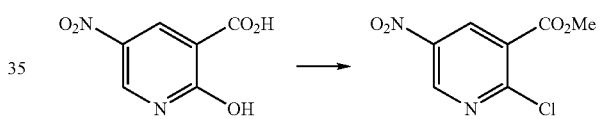

2-Hydroxy-5-nitronicotinic acid (29 g; 0.16 moles) was added portionwise to phosphorus oxychloride (90 ml) with stirring. The temperature was raised to 100° C. and heating continued for 3 hours before cooling to room temperature. The bulk of the solvent was removed before adding to ice-cold methanol (100 ml). The mixture was basified to pH 9 with saturated sodium bicarbonate solution and extracted with dichloromethane. The organic phase was dried (sodium sulphate), filtered and evaporated before purification by dry flash chromatography on silica gel. Methyl 2-chloro-5-nitronicotinate was eluted with 67% ethyl acetate in heptane (31 g, 90%).

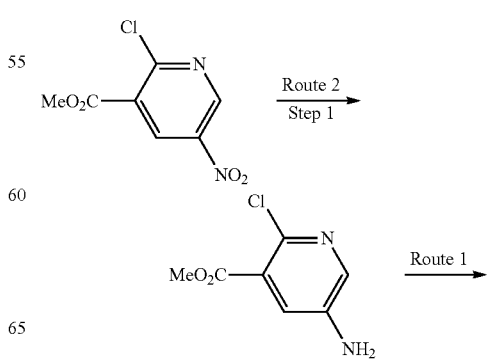

-continued

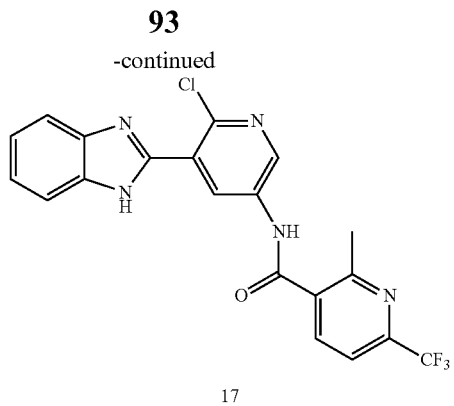

17

Methyl 2-chloro-5-nitronicotinate was reduced to the amine using the conditions described in route 2 step 2 and the methyl 5-amino-2-chloronicotinate taken through to compound 17 using the methods described in route 1: $^1$H NMR (400 MHz, MeOD) δ 9.02 (s, 1H), 8.73 (s, 1H), 8.08 (d, 1H), 7.86 (m, 2H), 7.69 (d, 1H), 7.62 (d, 2H) and 2.60 (s, 3H); MS (ES$^+$): 432 ($^{35}$Cl), 434 ($^{37}$Cl) [M$^+$+1], Compound 18

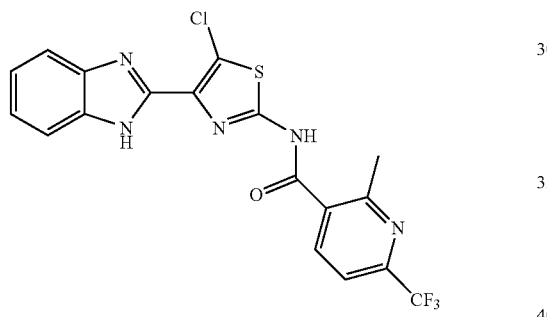

18

Ethyl 2-aminothiazole-4-carboxylate was chlorinated as described in Tet. Lett. 2002, 43 (39), 7051-7053 (J. F. Okonya and F. Al-Obeidi). This was then converted to compound 18 using route 1: $^1$H NMR (400 MHz, MeOD) δ 8.14 (d, 1H), 7.60 (d, 1H), 7.55 (m, 2H), 7.20 (m, 2H) and 2.65 (s, 3H); MS (ES$^+$): 438 ($^{35}$Cl), 440 ($^{37}$Cl) [M$^+$+1].

Compound 19

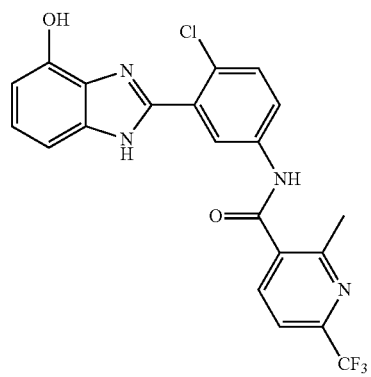

19

-continued

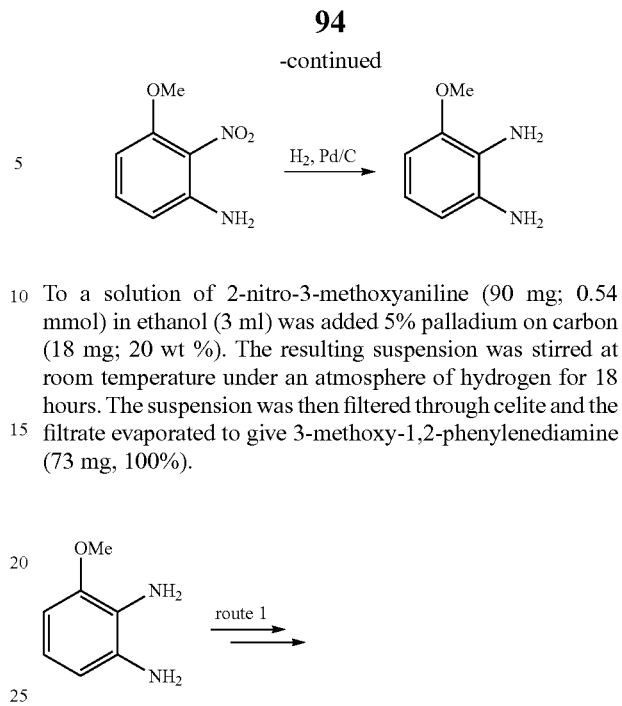

To a solution of 2-nitro-3-methoxyaniline (90 mg; 0.54 mmol) in ethanol (3 ml) was added 5% palladium on carbon (18 mg; 20 wt %). The resulting suspension was stirred at room temperature under an atmosphere of hydrogen for 18 hours. The suspension was then filtered through celite and the filtrate evaporated to give 3-methoxy-1,2-phenylenediamine (73 mg, 100%).

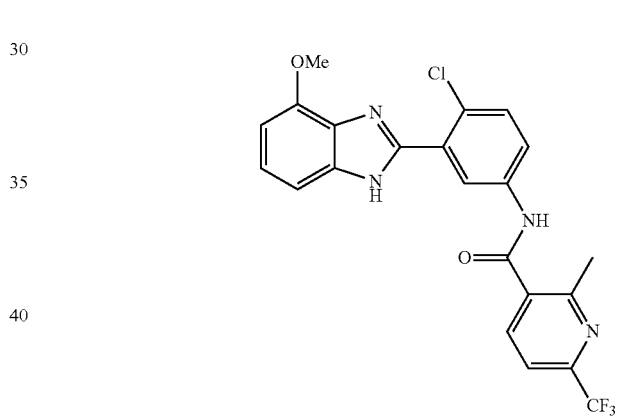

3-Methoxy-1,2-phenylenediamine was converted to N-[4-chloro-3-(7-methoxy-1H-benzoimidazol-2-yl)-phenyl]-2-methyl-6-trifluoromethyl-nicotinamide using route 1.

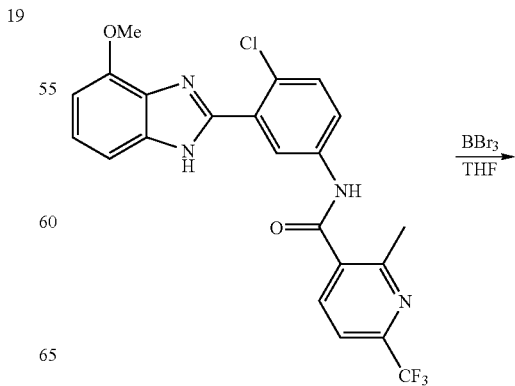

-continued

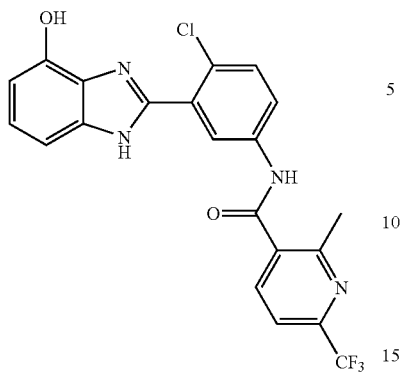

A solution of N-[4-chloro-3-(7-methoxy-1H-benzoimidazol-2-yl)-phenyl]-2-methyl-6-trifluoromethyl-nicotinamide (80 mg; 0.18 mmol) in ethanol (5 ml) was cooled to −78° C. and boron tribromide (130 mg; 0.52 mmol) was added dropwise. The reaction was allowed to warm to room temperature and stirred for 18 hours. Water (5 ml) was added and the reaction mixture was basified using saturated sodium bicarbonate solution. This was then extracted with dichloromethane (3×5 ml), the combined organic layers were dried (magnesium sulphate), filtered and evaporated to give the crude residue. This was recrystallised from hot acetonitrile to give compound 19 (10 mg, 14%): $^1$H NMR (400 MHz, MeOD) δ 8.15 (m, 2H), 7.95 (dd, 1H), 7.75 (d, 1H), 7.65 (d, 1H), 7.15 (m, 2H), 6.7 (dd, 1H), 2.75 (s, 3H); MS (ES$^+$): 447 ($^{35}$Cl), 449 ($^{37}$Cl) [M$^+$+1].

Compound 20

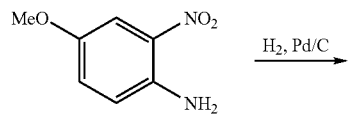

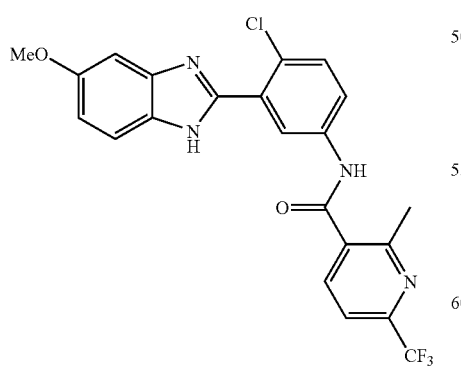

-continued

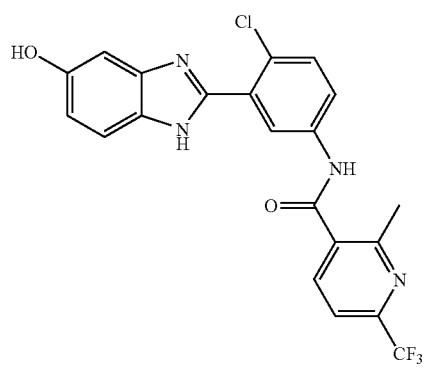

Compound 20 was prepared from 4-methoxy-2-nitroaniline following the procedures described for compound 19: $^1$H NMR (400 MHz, MeOD) δ 8.15 (m, 2H), 7.9 (d, 1H), 7.75 (d, 1H), 7.6 (d, 1H), 7.45 (brs, 1H), 7.90 (brs, 1H), 6.85 (d, 1H), 2.75 (s, 3H); MS (ES$^+$): 447 ($^{35}$Cl), 4-49 ($^{37}$Cl) [M$^+$+1].

Compound 25

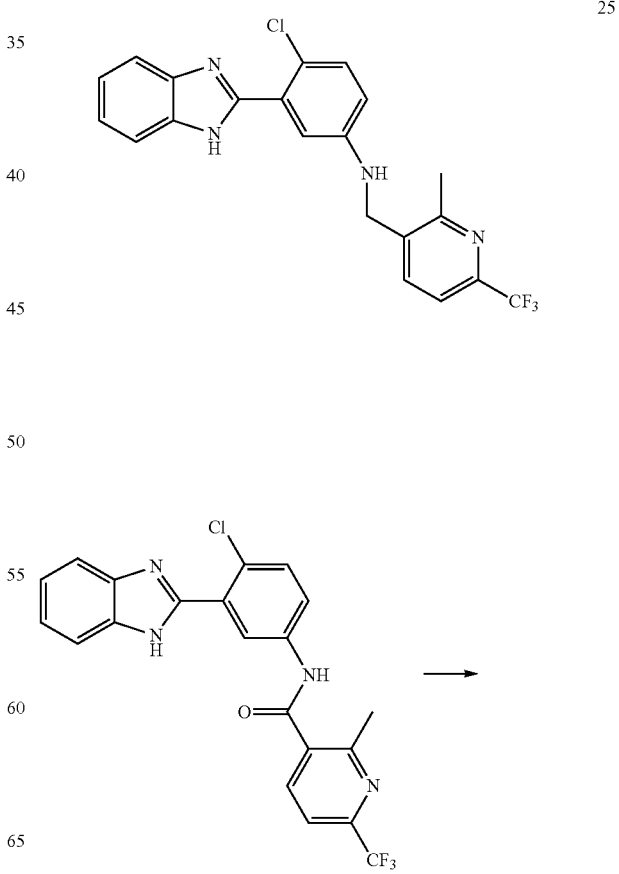

-continued

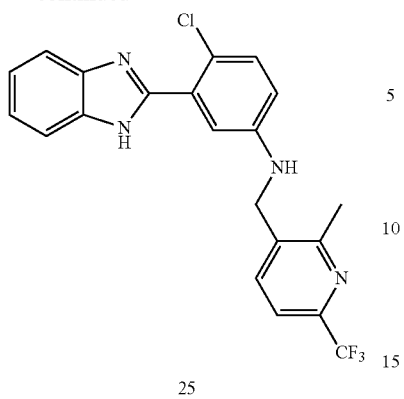
25

Lithium aluminium hydride (43 mg; 1.14 mmol) was dissolved in tetrahydrofuran (5 ml) and cooled to −78° C. Compound 1 (490 mg; 1.14 mmol) was also dissolved in tetrahydrofuran (5 ml) and added dropwise to the first solution. The reaction was stirred at room temperature then 1 M lithium aluminium hydride in t-butyl methyl ether (2.3 ml) was added in two portions and the reaction heated at 50° C. for 16 hours. The reaction was quenched with water (0.13 ml), 15% sodium hydroxide solution (0.13 ml) and water (0.39 ml) then filtered and the solid washed with ethyl acetate. Evaporation gave compound 25 (237 mg, 50%): $^1$H NMR (400 MHz, MeOD) δ 7.8-7.9 (m, 3H), 7.65-7.7 (M, 2H), 7.6 (d, 1H), 7.45 (d, 1H), 7.05 (s, 1H), 6.95 (d, 1H) 4.5 (s, 2H), 2.65 (s, 3H); MS (ES$^+$): 417 ($^{35}$Cl), 419 ($^{37}$Cl) [M$^+$+1].

Compound 30

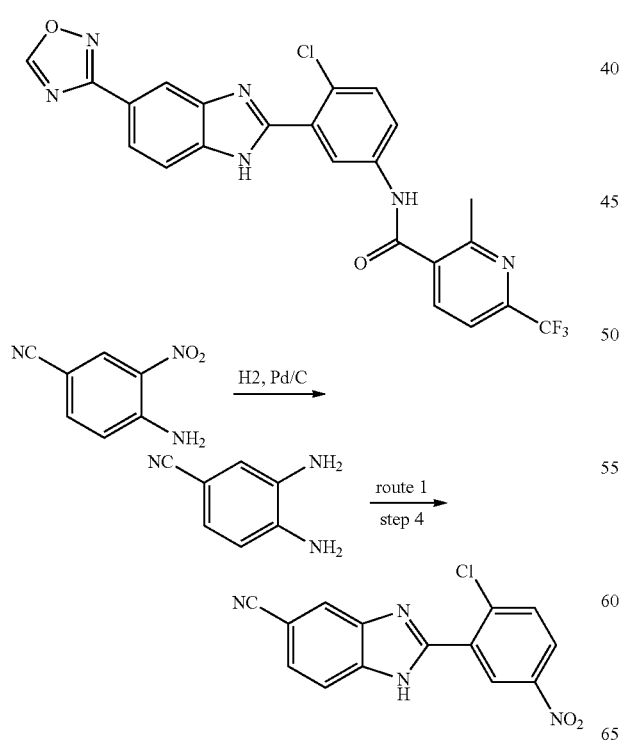

4-Amino-3-nitrobenzonitrile was reduced to 4-cyano-1,2-phenylenediamine as for compound 19. This was reacted with 2-chloro-5-nitrobenzaldehyde as described in route 1 step 4 to give 2-(2-chloro-5-nitro-phenyl)-1H-benzoimidazole-5-carbonitrile.

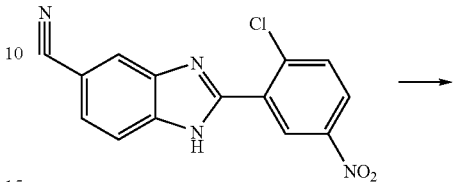

To a stirred solution of 2-(2-chloro-5-nitro-phenyl)-1H-benzoimidazole-5-carbonitrile (2.00 g; 6.70 mmol) in ethanol (20 ml) in a sealable tube was added triethylamine (1.90 ml; 13.4 mmol). A solution of hydroxylamine hydrochloride (933 mg; 13.4 mmol) in water (4 ml) was added, the tube sealed and the mixture stirred at 75° C. for 2 hours. After cooling to room temperature, water (100 ml) was added, the precipitate filtered and washed with more water to leave 2-(2-chloro-5-nitro-phenyl)-N-hydroxy-1H-benzoimidazole-5-carboxamidine (1.76 g, 82%).

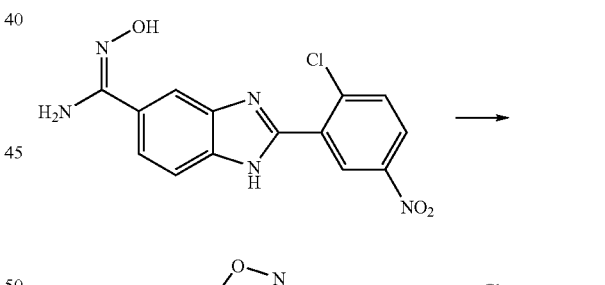

A stirred solution of 2-(2-chloro-5-nitro-phenyl)-N-hydroxy-1H-benzoimidazole-5-carboxamidine (5.29 g; 16.0 mmol) in triethyl orthoformate (50 ml) was heated to 80° C. Concentrated hydrochloric acid (3 drops) was added and heating continued for a further two hours. After cooling to room temperature, heptane (50 ml) was added which caused a precipitate to form. The solid was filtered off and washed with more heptane to afford 2-(2-chloro-5-nitro-phenyl)-5-[1,2,4]oxadiazol-3-yl-1H-benzoimidazole (3.30 g, 62%)

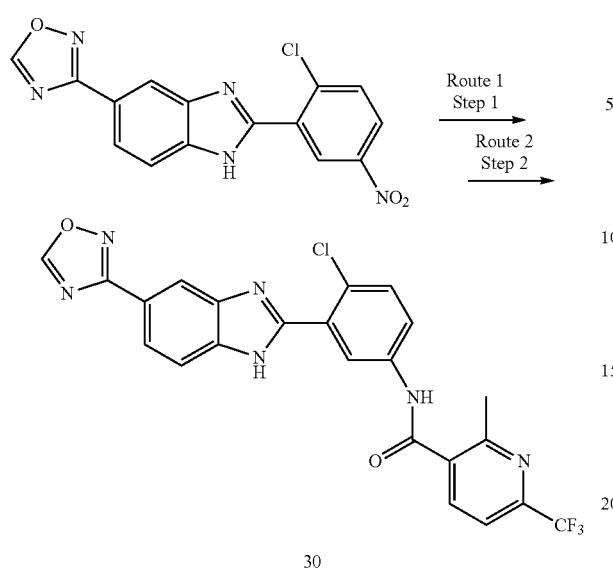

2-(2-Chloro-5-nitro-phenyl)-5-[1,2,4]oxadiazol-3-yl-1H-benzoimidazole was converted into compound 30 using route 2 step 2 then route 1 step 1: $^1$H NMR (400 MHz, MeOD) δ 9.4 (s, 1H), 8.65 (d, 1H), 8.6 (s, 1H), 8.45 (d, 1H), 8.15 (d, 1H), 8.05 (d, 1H), 7.75-7.85 (m, 3H), 2.75 (s, 3H); MS (ES$^+$): 499 ($^{35}$Cl), 501 ($^{37}$Cl) [M$^+$+1].

Compound 34

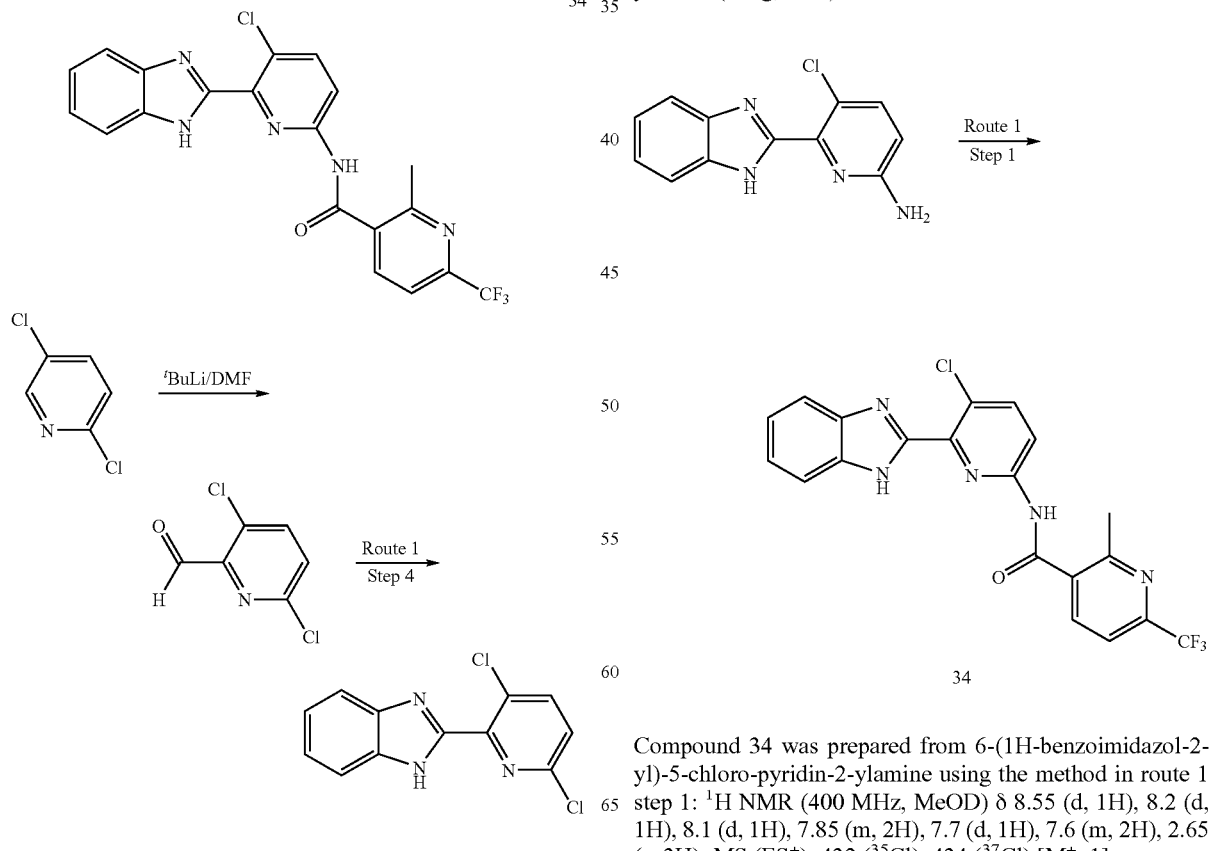

3,6-Dichloropyridine-2-carboxaldehyde was prepared from 2,5-dichloropyridine using the procedure described in Eur. J. Org. Chem. 2001, 1371-1376 (E. Marzi, A. Bigi, M. Schlosser) and converted to 2-(3,6-dichloro-pyridin-2-yl)-1H-benzoimidazole using the method in route 1 step 4.

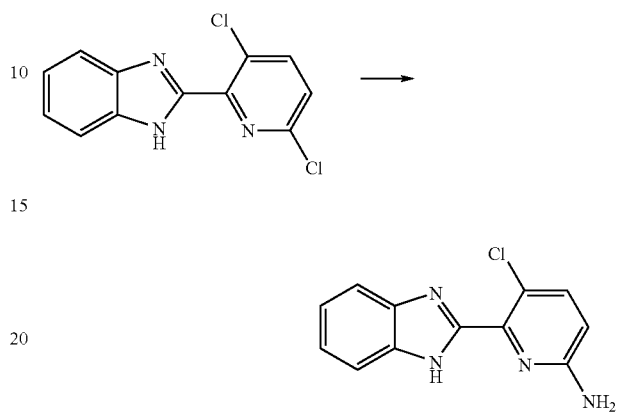

2-(3,6-Dichloro-pyridin-2-yl)-1H-benzoimidazole (20 mg; 0.076 mmol) was dissolved in ethanol (1.5 ml) and concentrated ammonia (2 ml) in a pressure tube. After 1000 minutes in a microwave at 140° C. and 200 psi, the solvents were removed and the residue dissolved in isopropyl alcohol (1 ml) and concentrated ammonia (1 ml) before microwaving as before. The solvents were evaporated and the residue chromatographed on silica gel with 80% ethyl acetate in heptane to give 6-(1H-benzoimidazol-2-yl)-5-chloro-pyridin-2-ylamine (4 mg, 21%).

Compound 34 was prepared from 6-(1H-benzoimidazol-2-yl)-5-chloro-pyridin-2-ylamine using the method in route 1 step 1: $^1$H NMR (400 MHz, MeOD) δ 8.55 (d, 1H), 8.2 (d, 1H), 8.1 (d, 1H), 7.85 (m, 2H), 7.7 (d, 1H), 7.6 (m, 2H), 2.65 (s, 3H); MS (ES$^+$): 432 ($^{35}$Cl), 434 ($^{37}$Cl) [M$^+$+1].

Compound 38

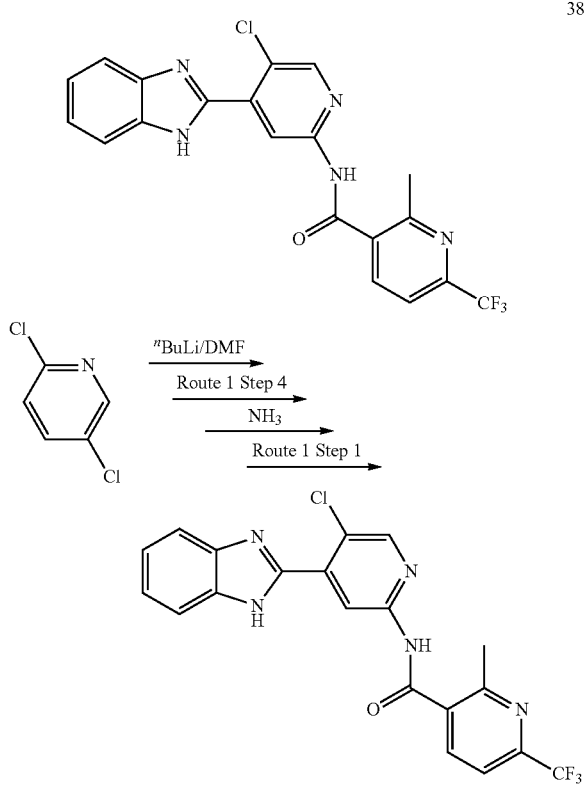

2,5-Dichloropyridine-4-carboxaldehyde was prepared from 2,5-dichloropyridine using the procedure described in Eur. J. Org. Chem. 2001, 1371-1376 (E. Marzi, A. Bigi, M. Schlosser) and converted to 2-(2,5-dichloro-pyridin-3-yl)-1H-benzoimidazole using the method in route 1 step 4. This was animated, as described for compound 34 and the aminopyridine converted to compound 38 using the method in route 1 step 1: $^1$H NMR (400 MHz, MeOD) δ 8.75 (s, 1H), 8.45 (s, 1H), 8.05 (d, 1H), 7.5-7.75 (brm, 3H), 7.2-7.3 (brm, 2H), 2.65 (s, 3H); MS (ES$^+$): 432 ($^{35}$Cl), 434 ($^{37}$Cl) [M$^+$+1].

Biological Assays

Lead Compound Discovery/High-Throughput Screening Assay

Compounds to be tested are dissolved in DMSO to a concentration of 10 mM, and stored at −20° C. To activate the Hedgehog pathway in the assay cells, an octylated (lipid-modified) form of the N-terminal fragment of the Sonic Hedgehog protein (OCT-SHH) is used. This N-terminal SHH fragment is produced bacterially. See, for example, Taylor F R, et al, *Biochemistry* 2001, 40, 4359-71.

Compounds may be tested in the "Gli-Luc" assay below, using the cell line 10T1/2(s12), wherein the cells contain a Hedgehog-responsive reporter construct utilizing Luciferase as the reporter gene. In this way, Hedgehog pathway signaling activity can be measured via the Gli-Luc response.

10t1/2(s12) cells are plated in a 96-well micro-titer plate (MTP) at 20,000 cells/well in full medium [DMEM with 10% FBS]. Then plates are placed in the incubator for incubation overnight (O/N), at 37° C. and 5% CO$_2$. After 24 h, the medium is replaced with Luciferase-assay medium (DMEM with 0.5% FBS). Compounds are thawed and diluted in assay medium at 3:1000 (about 300-fold) resulting in a starting concentration of about 0.0003 μM to 30 μM.

Subsequently, 150 μl of each sample is added to the first wells (in triplicate). The MTP samples are then diluted at 3-fold dilutions to a total of seven wells, ultimately resulting in a regiment of seven dilutions in triplicate, for each compound. Next, the protein ligand OCT-SHH is diluted in Luciferase-assay medium and added to each well at a final concentration of 0.3 μg/ml. Plates are then returned to the incubator for further incubation O/N, at 37° C. and 5% CO$_2$. After about 24 h, plates are removed from the incubator and the medium is aspirated/discarded. Wells are washed once with assay buffer [PBS+1 mM Mg$^{2+}$ and 1 mM Ca$^{2+}$]. Then 50 μl of assay buffer is added to each well. The Luciferase assay reagent is prepared as described by the vendor (LucLite kit from Packard), and 50 μl is added to each well. Plates are incubated at room temperature (RT) for about 30 minutes after which the signals are read, again at RT, on a Topcount (Packard).

Similar assays were performed using human cell lines (specifically, human embryonic palatal mesenchyme cells, modified with the Gli-Luc construct as described above) in a growth medium of MEM/Sodium Pyruvate w/ 10% FBS, and an assay medium of MEM/Sodium Pyruvate w/ 0.5% FBS. OCT-SHH was added to reach a final concentration of 1 μg/ml.

Compounds identified in the above assays are depicted in Table 1.

All of the references cited above are hereby incorporated by reference herein.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for inhibiting activation of a hedgehog pathway in a cell, comprising contacting the cell with a compound of formula (I) in a sufficient amount to inhibit hedgehog signalling;

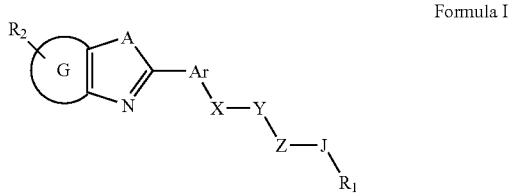

Formula I wherein, as valence and stability permit,
X is —NH—;
Z is a direct bond;
Y represents —C(=O)—;
A represents O, S, or NR$_7$;
G represents cyclohexane, pyridine, phenyl or phenyl fused with 1,3-dioxolane;
Ar represents phenyl, pyridine, 1,3-thiazole or thiophene, optionally substituted by halogen, lower alkoxy, lower alkyl or halogenated lower alkyl;
R$_1$ represents a disubstituted pyridine ring wherein the substitutents are selected from nitro, cyano, lower alkyl, halogenated lower alkyl, alkenyl, alkynyl, phenylalkyl, amino, alkylamino, acylamino, amido, hydroxyl, alkoxy, acyloxy, carbonyl, phosphoryl, sulfamoyl, sulfate, sulfonamide, sulfonate, sulfoxido, sulfhydryl, and sulfonyl;

$R_2$ represents from 0-4 substituents on the ring to which it is attached wherein the substitutents are selected from halogen, lower alkyl, halogenated lower alkyl, lower alkenyl, 5, 6 or 7-membered single ring aryl, 5, 6 or 7-membered single ring heteroaryl with 1-4 heteroatoms, 3 to 7-membered heterocyclyl with 1-4 heteroatoms, ester, carboxyl, formyl, thioester, thiocarboxylate, thioformate, ketone, aldehyde, amino optionally substituted by alkyl, acylamino, amido, amidino, cyano, nitro, azido, alkylthio, sulfonyl, sulfoxido, sulfate, sulfonate, sulfamoyl, sulfonamido, phosphoryl, phosphonate, phosphinate, —OH, —SH, —NH$_2$, or any two $R_2$, when occurring more than once in a cyclic or polycyclic structure, can be taken together form a 4- to 8-membered cycloalkyl, aryl, or heteroaryl;

$R_7$ represents H, lower alkyl, or lower alkyl substituted by —CONH$_2$, morpholine, piperidine or piperidine N-substituted by —COO-tert-butyl; and J is absent.

2. The method of claim 1, wherein the cell has a phenotype of patched (ptc) loss-of-function, hedgehog gain-of-function, or smoothened gain-of-function.

3. The method of claim 1, wherein the compound inhibits patched (ptc) loss-of-function, hedgehog gain-of-function, or smoothened gain-of-function mediated signal transduction with an ED$_{50}$ of 1 µM or less.

4. The method of claim 1, wherein the compound inhibits patched (ptc) loss-of-function, hedgehog gain-of-function, or smoothened gain-of-function mediated signal transduction with an ED$_{50}$ of 1 nM or less.

5. The method of claim 1, wherein the cell is contacted with the compound of formula (I) in vitro.

6. The method of claim 1, wherein the cell is contacted with the compound of formula (I) in vivo.

7. A method for treating basal cell carcinoma, comprising administering a pharmaceutical preparation comprising a sterile pharmaceutical excipient and a compound of Formula (I) to a patient in an amount sufficient to inhibit progression of basal cell carcinoma;

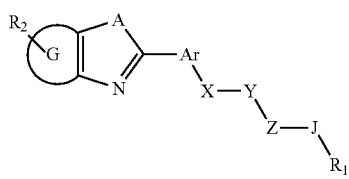

Formula (I)

wherein, as valence and stability permit,

X is —NH—;
Z is a direct bond;
Y represents —C(=O)—
A represents O, S, or NR$_7$;
G represents cyclohexane, pyridine, phenyl, or phenyl fused with 1,3-dioxolane;
Ar represents phenyl, pyridine, 1,3-thiazole or thiophene, optionally substituted by halogen, lower alkoxy, lower alkyl, or halogenated lower alkyl;

$R_1$ represents a disubstituted pyridine ring wherein the substituents are selected from nitro, cyano, lower alkyl, halogenated lower alkyl, alkenyl, alkynyl, phenylalkyl, amino, alkylamino, acylamino, amido, hydroxyl, alkoxy, acyloxy, carbonyl, phosphoryl, sulfamoyl, sulfate, sulfonamide, sulfonate, sulfoxido, sulfhydryl, and sulfonyl;

$R_2$ represents from 0-4 substituents on the ring to which it is attached wherein the substituents are selected from halogen, lower alkyl, halogenated lower alkyl, lower alkenyl, 5, 6, or 7-membered single ring aryl, 5, 6, or 7-membered single ring heteroaryl with 1-4 heteroatoms, 3 to 7 membered heterocyclyl with 1-4 heteroatoms, ester, carboxyl, formyl, thioester, thiocarboxylate, thioformate, ketone, aldehyde, amino optionally substituted with alkyl, acylamino, amido, amidino, cyano, nitro, azido, alkylthio, sulfonyl, sulfoxido, sulfate, sulfonate, sulfamoyl, sulfonamido, phosphoryl, phosphonate, phosphinate, —OH, —SH, —NH$_2$, or any two $R_2$, when occurring more than once in a cyclic or polycyclic structure, can be taken together to form a 4- to 8-membered cycloalkyl, aryl, or heteroaryl;

$R_7$ represents H, lower alkyl, or lower alkyl substituted by —CONH$_2$, morpholine, piperidine, or piperidine N-substituted by —COO-tert-butyl; and J is absent.

8. The method of claim 1, wherein in Formula (I) $R_1$ represents a disubstituted pyridine ring.

9. The method of claim 1, wherein in Formula (I) the pyridine ring of $R_1$ is attached to J at a position meta to the nitrogen atom of the pyridine ring.

10. The method of claim 1, wherein in formula (I), $R_1$ is substituted with a methyl or trifluoromethyl group.

11. The method of claim 1, wherein in formula (I), $R_1$ is 6-(trifluoromethyl)-2-methylpyridin-3-yl.

12. The method of claim 1, wherein in formula (I), X and the ring comprising A are disposed on Ar in a meta relationship.

13. The method of claim 1, wherein in formula (I), $R_2$ represents from 1-4 substituents selected from halogen, lower alkyl, lower alkenyl, aryl, heteroaryl, carbonyl group, thiocarbonyl, ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, J-R$_8$, J-OH, J-lower alkyl, J-lower alkenyl, J-R$_8$, J-SH, J-NH$_2$, protected forms of the above, or any two $R_2$, when occurring more than once in a cyclic or polycyclic structure, can be taken together form a 4- to 8-membered cycloalkyl, aryl, or heteroaryl.

14. The method of claim 1, wherein in formula (I), $R_2$ represents from 1-4 substituents selected from halogen, cyano, nitro, alkoxy, amino, acylamino (e.g., R$_8$—C(=O) NH—), a substituted or unsubstituted cycloalkyl, heterocyclyl, aryl, or heteroaryl fused to G, and substituted or unsubstituted lower alkyl.

* * * * *